United States Patent
Jaiswal et al.

(10) Patent No.: US 9,765,143 B2
(45) Date of Patent: *Sep. 19, 2017

(54) METHODS FOR MANIPULATING PHAGOCYTOSIS MEDIATED BY CD47

(71) Applicant: The Board of Trustees of the Leland Stanford Junior University, Stanford, CA (US)

(72) Inventors: Siddhartha Jaiswal, San Francisco, CA (US); Irving L. Weissman, Stanford, CA (US); Ravindra Majeti, Palo Alto, CA (US); Mark P. Chao, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/456,109

(22) Filed: Mar. 10, 2017

(65) Prior Publication Data

US 2017/0190776 A1    Jul. 6, 2017

Related U.S. Application Data

(63) Continuation of application No. 15/054,891, filed on Feb. 26, 2016, now Pat. No. 9,624,305, which is a continuation of application No. 14/800,474, filed on Jul. 15, 2015, now Pat. No. 9,399,682, which is a continuation of application No. 13/941,276, filed on Jul. 12, 2013, now abandoned, which is a continuation of application No. 12/837,409, filed on Jul. 15, 2010, now Pat. No. 8,562,997, which is a continuation-in-part of application No. PCT/US2009/000319, filed on Jan. 15, 2009.

(60) Provisional application No. 61/011,324, filed on Jan. 15, 2008, provisional application No. 61/189,786, filed on Aug. 22, 2008.

(51) Int. Cl.
| | |
|---|---|
| *A61K 39/395* | (2006.01) |
| *C07K 16/28* | (2006.01) |
| *C07K 16/30* | (2006.01) |
| *A61K 39/00* | (2006.01) |

(52) U.S. Cl.
CPC .......... *C07K 16/2803* (2013.01); *C07K 16/30* (2013.01); *C07K 16/3053* (2013.01); *C07K 16/3061* (2013.01); *C07K 16/3069* (2013.01); *A61K 2039/505* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,867,973 A | 9/1989 | Goers et al. |
| 6,465,247 B1 | 10/2002 | Weissman et al. |
| 6,491,917 B1 | 12/2002 | Thomas et al. |
| 6,733,743 B2 | 5/2004 | Jordan |
| 7,008,773 B1 | 3/2006 | Freyberg et al. |
| 8,361,736 B2 | 1/2013 | Majeti et al. |
| 8,562,997 B2 | 10/2013 | Jaiswal et al. |
| 8,758,750 B2 | 6/2014 | Weissman et al. |
| 9,352,037 B2 | 5/2016 | van den Berg |
| 9,399,682 B2 | 7/2016 | Jaiswal et al. |
| 2004/0213792 A1 | 10/2004 | Clemmons et al. |
| 2005/0118164 A1 | 6/2005 | Hermon |
| 2005/0142539 A1 | 6/2005 | Herman |
| 2006/0135749 A1 | 6/2006 | Takashi et al. |
| 2006/0239910 A1 | 10/2006 | Nicolaides et al. |
| 2007/0111238 A1 | 5/2007 | Catriona et al. |
| 2007/0113297 A1 | 5/2007 | Yang et al. |
| 2007/0287163 A1 | 12/2007 | Geuijen et al. |
| 2008/0131431 A1 | 6/2008 | Smith et al. |
| 2008/0187950 A1 | 8/2008 | Weissman et al. |
| 2010/0255575 A1 | 10/2010 | Weissman et al. |

FOREIGN PATENT DOCUMENTS

| | | |
|---|---|---|
| EP | 1693385 A1 | 8/2006 |
| EP | 2111869 A1 | 10/2009 |
| JP | 2001/503253 A | 3/2001 |
| JP | 2003/518514 A | 6/2003 |
| JP | 2004/504408 A | 2/2004 |
| JP | 2005/333993 A | 12/2005 |
| WO | 99/10478 A1 | 3/1999 |
| WO | 99/40940 A1 | 8/1999 |
| WO | 03/074567 A2 | 9/2003 |

(Continued)

OTHER PUBLICATIONS

Majeti et al. "CD47 is an adverse prognostic factor and therapeutic antibody target on human acute myeloid leukemia stem cells", Developmental Cell (Jul. 2009), 138(2):286-299.

(Continued)

*Primary Examiner* — Karen Canella

(74) *Attorney, Agent, or Firm* — Pamela J. Sherwood; Boziceviz, Field & Francis LLP

(57) ABSTRACT

Methods are provided to manipulate phagocytosis of cells, including hematopoietic cells, e.g. circulating hematopoietic cells, bone marrow cells, acute leukemia cells, etc.; and solid tumor cells. In some embodiments of the invention the circulating cells are hematopoietic stem cells, or hematopoietic progenitor cells, particularly in a transplantation context, where protection from phagocytosis is desirable. In other embodiments the circulating cells are leukemia cells, particularly acute myeloid leukemia (AML), where increased phagocytosis is desirable.

10 Claims, 49 Drawing Sheets

(56) References Cited

FOREIGN PATENT DOCUMENTS

| WO | 2004/096133 A2 | 11/2004 |
|---|---|---|
| WO | 2005/044857 A1 | 5/2005 |
| WO | 2006/089133 A2 | 8/2006 |
| WO | 2007/121465 A2 | 10/2007 |
| WO | 2007/133811 A2 | 11/2007 |
| WO | 2009/046541 A1 | 4/2009 |
| WO | 2009/091547 A1 | 7/2009 |
| WO | 2009/091601 A1 | 7/2009 |
| WO | 2009/131453 A1 | 10/2009 |
| WO | 2010/017332 A2 | 2/2010 |
| WO | 2010/130053 A1 | 11/2010 |
| WO | 2011/034969 A1 | 3/2011 |

OTHER PUBLICATIONS

Majeti et al. "CD47 Is an Independent Prognostic Factor and Theraputic Antibody Target on Human Acute Myeloid Leukemia Stem Cells", Blood (Jul. 2008), 138(2):286-299.

Manna et al., "The mechanism of CD4 7-dependent killing ofT cells: heterotrimeric Gi-dependent inhibition of protein kinase A", J Immunol (2003). 170(7):3544-53.

Manna et al. "CD47 mediates killing of breast tumor cells via Gi-dependent inhibition of protein kinase A", Cancer Research (Feb. 2004), 64(3):1026-1036.

Mawby et al., "Isolation and characterization of CD47 glycoprotein: a multispanning membrane protein which is the same as integrin-associated protein (IAP) and the ovarian tumour marker OA3", Biochem. J., Dec. 1, 1994, pp. 525-530, 304(2), The Biochemical Society, London, United Kingdom.

McDonald et al. "Cholesterol-independent interactions with CD47 enhance alphavbeta3 avidity", J Biol Chem (Apr. 2004), 279(17):17301-17311.

Motegi et al., "Role of the CD47-SHP5-1 system in regulation of cell migration", EMBO, Jun. 1, 2003, pp. 2634-2644, vol. 22, Issue 11.

Musolino et al., Immunoglobulin G Fragment C Receptor Polymorphisms and Clinical Efficacy of Trastuzumab-Based Therapy in Patients With HER-2/neu-Positive Metastatic Breast Cancer, Journal of Clinical Oncology, Apr. 10, 2008, pp. 1789-1796, vol. 26, No. 11, American Society of Clinical Oncology, Alexandria, VA.

NCBI protein database—SIRP alpha. Jun. 6, 2006, pp. 1-3.

Okazawa et al., "Negative Regulation of Phagocytosis in Macrophages by the CD47-SHPS-1 System", The Journal of Immunology, 2005, pp. 2004-2011, 174, The American Association of Immunologists, Inc., Bethesda, MD.

Oldenborg et al., "CD47-Signal Regulatory Protein a (SIRPa) Regulates Fcγ and Complement Receptor-mediated Phagocytosis", J. Exp. Med., Apr. 2, 2001, pp. 855-861, vol. 193, No. 7, The Rockefeller University Press, New York, NY.

Oldenborg et al., "Role of CD47 as a Marker of Self on Red Blood Cells", Science, Jun. 16, 2000, pp. 2051-2054, vol. 288, No. 5473, American Association for the Advancement of Science, Washington, D.C.

Ouban et al., "Expression and Distribution of Insulin-Like Growth Factor-1 Receptor in Human Carcinomas", Human Pathology, Aug. 2003, pp. 803-808, vol. 34, No. 8, Elsevier Inc., Amsterdam, Netherlands.

Ozols, "Challenges for chemotherapy in ovarian cancer", Annals of Oncology, May 2006, pp. v181-v187, vol. 17, Supplement 5, European Society for Medical Oncology, Lugano, Switzerland.

Passegue et al. "JunB deficiency leads to a myeloproliferative disorder arising from hematopoietic stem cells", Cell (Oct. 2004), 119:431-443.

Pettersen et al. "CD47 signals T cell death", J Immunol {Jun. 1999), 162(12):7031-7040.

Samani et al., The Role of the IGF System in Cancer Growth and Mestastasis: Overview and Recent Insights, Endocrine Reviews 28(1 ):30-47, Feb. 2007.

Schlom, "Monoclonal Antibodies: They're More and Less Than You Think", In: Molecular Foundations of Oncology, 1991, pp. 95-134, Williams & Wilkins, Baltimore, MD.

Shahan et al., "Identification of CD47/Integrin-associated Protein and $\alpha v\beta 3$ as Two Receptors for the $\alpha 3$(IV) Chain of Type IV Collagen on Tumor Cells", Cancer Research, Sep. 1999, pp. 4584-4590, vol. 59, Issue 18.

Subramanian et al. "Species- and cell type-specific interactions between CD47 and human SIRPalpha", Blood (Mar. 2006), 107(6):2548-2556.

Sutherland et al. "Characterization of a hierarchy in human acute myeloid leukemia progenitor cells", Blood (Jun. 1996), 87(11):4754-4761.

Tibes et al., "Activity of Alemtuzumab in Patients with CD52-Positive Acute Leukemia", Cancer, Jun. 15, 2006, pp. 2645-2651, vol. 106, No. 12, American Cancer Society, Atlanta, GA.

Veillette et al., "High Expression of Inhibitory Receptor SHPS-1 and Its Association with Protein-tyrosine Phosphatase SHP-1 in Macrophages", The Journal of Biological Chemistry, Aug. 28, 1998, pp. 22719-22728, vol. 273, No. 35, The American Society for Biochemistry and Molecular Biology, Inc., Rockville, MD.

Weisenthal, "Synergy analysis of "classic" and newer drug combinations", Human Tumor Assay Journal, on-line at http://weisenthal.org/synergy1.htm, Mar. 14, 2012, p. 1.

White et al., "Monoclonal antibodies inhibit prion replication and delay the development of prion disease", Nature, Mar. 6, 2003, pp. 80-83, vol. 422.

Willingham et al. "The CD47-signal regulatory protein alpha (SIRa) interaction is a therapeutic target for human solid tumors", PNAS (Apr. 2012), 109(17):6662-6667.

Younes et al., "A Pilot Study of Rixuximab in Patents with Recurrent, Classic Hodgkin Disease", Cancer, 2003, pp. 310-314, vol. 98, American Cancer Society, Atlanta, GA.

Zengers et al., "Studies on FD Fragments of Human Immunoglobulins", Scand. J. Immunol., 1975, pp. 161-169, 4, Blackwell Scientific Publications, Oxford, United Kingdom.

Zhao et al., "CD47-signal regulatory protein-a {SIRPa) interactions form a barrier for antibody-mediated tumor cell destruction", Proc Natl Acad Sci USA (2011), 108{45):18342-18347.

Zhao et al., "Is targeting of CD47-SIRPa enough for treating hematopoietic malignancy?", Blood (2012), 119(18):4333-4334.

Zheng et al., "Gene expression profiling of CD34ρ cells identifies a molecular signature of chronic myeloid leukemia blast crisis", Leukemia, Apr. 13, 2006, pp. 1028-1034, 20, Nature Publishing Group, London, United Kingdom.

Akashi et al. "A clonogenic common myeloid progenitor that gives rise to all myeloid lineages", Nature (Mar. 2000), 404:193-197.

Alinari et al.,"Alemtuzumab (Campath-1H) in the treatment of chronic lymphocytic leukemia", Oncogene, 2007, pp. 3644-3653, 26, Nature Publishing Group, London, United Kingdom.

Arsenijevic et al., "Phagocytic Activity of Monocytes in Patients with Breast Cancer at Different Clinical Stages", Breast Cancer Research, Jun. 2001, pp. S1-S24, Abstract "A4" vol. 3 Suppl 1, 23rd Congress of the International Association for Breast Cancer Research, Düsseldorf, Germany.

Baxter et al. "Acquired mutation of the tyrosine kinase JAK2 in human myeloproliferative disorders", The Lancet (Mar. 2005), 365:1054-1061.

Berenbaum, "Synergy, additivism and antagonism in immunosuppression a critical review", Clin exp Immunol, Apr. 1997, pp. 1-18, 28, National Center for Biotechnology Information, Bethesda MD.

Bookman et al., "Evaluation of Monoclonal Humanized Anti-HER2 Antibody, Trastuzumab, in Patients With Recurrent or Refractory Ovarian or Primary Peritoneal Carcinoma With Over expression of HER2: A Phase II Trial of the Gynecologic Oncology Group", Journal of Clinical Oncology, Jan. 15, 2003, pp. 283-290, vol. 21, American Society of Clinical Oncology, Alexandria, VA.

Brooke et al. "Human Lymphocytes Interact Directly with CD47 Through a Novel Member of the Signal Regulatory Protein (SIRP) Family", The Journal of Immunology (Aug. 2004), 173:2562-2570.

(56) References Cited

OTHER PUBLICATIONS

Burger et al., "Phase II Trial of Bevacizumab in Persistent or Recurrent Epithelial Ovarian Cancer or Primary Peritoneal Cancer: A Gynecologic Oncology Group Study", Journal of Clinical Oncology, Nov. 20, 2007, pp. 5165-5172, vol. 25, No. 33, American Society of Clinical Oncology, Alexandria, VA.
Chan; et al. "Identification, molecular characterization, clinical prognosis, and therapeutic targeting of human bladder tumor-initiating cells", PNAS (Aug. 2009), 106(33):14016-14021.
Chao et al., "Therapeutic antibody targeting of CD47 eliminates human acute lymphoblastic leukemia", Cancer Res (2011), 71{4}:1374-1384.
Clarke; et al. "Cancer stem cells—perspectives on current status and future directions: AACR Workshop on cancer stem cells", Cancer Research (Oct. 2006), 66(19):9339-9344.
Clynes et al., "Inhibitory Fc receptors modulate in vivo cytoxicity against tumor targets", Nature Medicine, Apr. 2000, pp. 443-446, vol. 6, No. 4, Nature Publishing Group, London, United Kingdom.
Coiffier, Bertrand, State of the Art Therapeutics: Diffuse Large B-Cell Lymphome, Journal of Clinical Oncology, vol. 23, No. 26, pp. 6387-6393, Sep. 10, 2005.
Conrad; et al. "Inflammatory cytokines predominate in cases of tumor regression after hematopoietic stem cell transplantation for solid cancer", Biology of Blood and Marrow Transplantation (Mar. 2006), 12:345-354.
Curriculum Vitae Randolph Wall, Ph.D., Filed: Aug. 5, 2016, 9 pages.
De Vries Maaike J., Rituximab in three children with relapsed/refractory B-cell acute lymphoblastic leukaemia/Burkitt non-Hodgkin's lymphoma, British Journal of Haematology, vol. 125, pp. 405-417, 2004.
Declaration of Randolph Wall, Ph.D., Filed: Aug. 5, 2016, 107 Pages.
Demeure et al. "CD47 Engagement inhibits cytokine production and maturation of human dendritic cells", The Journal of Immunology (Feb. 2000), 164:2193-2199.
Durando et al. "High-dose BCNU followed by autologous hematopoietic stem cell transplantation in supratentorial15 3 high-grade malignant gliomas: a retrospective analysis of 114 patients", Bone Marrow Transplantation (Apr. 2003), 31(7):559-564.
Eichler et al."CD97 isoform expression in leukocytes", J Leukoc Bioi {Oct. 2000), 68(4):561-567.
Fey et al. "ESMO Minimum Clinical Recommendations for diagnosis, treatment and follow-up of acute myeloblastic leukaemia (AML) in adult patients", Annals of Oncology (Aug. 2003), 14(8):1161-1162.
Forty Seven, Inc., Petition for Inter Partes Review of U.S. Pat. No. 9,352,037, Filed: Aug. 5, 2016, Case No. IPR2016-01529, 74 Pages.
Forty Seven, Inc., Petition for Inter Partes Review of U.S. Pat. No. 9,352,037, Filed: Aug. 8, 2016, Case No. IPR2016-01530, 76 Pages.
Fuchs et al. "Cutting edge: CD96 (tactile) promotes NK cell-target cell adhesion by interacting with the poliovirus receptor (CD155)", J Immonul (Apr. 2004), 172(7):3994-3998.
Gibson et al., Clin Lymphoma, "Phase III Trial of a Humanized Anti-CD33 Antibody (HuM195) in Patients with Relapsed or Refractory Acute Myeloid Leukemia", Jun. 2002, pp. 18-19, 3(1), Elsevier Inc., Amsterdam, Netherlands.
Giles, "The Vascular Endothelial Growth Factor (VEGF) Signaling PAthway: A Therapeutic Target in Patients withHematologic Malignancies", The Oncologist, (2001), pp. 32-39, 1; 6(suppl 5), AlphaMed Press, Durham, NC.
Gleason et al "TIM-3 is an inducible human natural killer cell receptor that enhances interferon production in response to galectin-9", Blood {Feb. 2012), 1-42.
Gokbuget et al., "Novel Antibody-Based Therapy for Acute Lymphoblastic Leukaemia", Best Practice & Research Clinical Haematology, 2006, pp. 701-713, vol. 19, Elsevier Ltd., Atlanta, GA.

Harmsen et al., "Properties, production, and applications of camelid single-domain antibody fragments", Appl Microbial Biotechnol, 2007, pp. 13-22, 77, Springer, Berlin, Germany.
Heibeis; et al. "Vav proteins are required forB-lymphocyte responses to LPS", Blood (Jul. 2005), 106(2):635-640.
Hosen; et al. "CD96 is a leukemic stem cell-specific marker in human acute myeloid leukemia", PNAS (Jun. 2007). 104 (26):11008-11013.
Imai et al., "Comparing antibody and small-molecule therapies for cancer", Nature Reviews/Cancer, Sep. 2006, pp. 714-727, vol. 6, Nature Publishing Group, London, United Kingdom.
Imayoshi; et al. "Expression of CD180, a toll-like receptor homologue, is up-regulated in children with Kawasaki disease", Jo Mol Med (Feb. 2006), 84(2):168-174.
Imbert; et al. "CD99 expressed on human mobilized peripheral blood CD34+ cells is involved in transendothelial migration", Blood (Oct. 2006), 108(8):2578-2586.
Jaattela, "Multiple cell death pathways as regulators of tumour inititation and progression", Oncogene, (2004) pp. 2746-2756, 23, Nature Publishing Group, London, United Kingdom.
Jaiswal et al., "Macrophages as mediators of tumor immunosurveillance", Trends Immunol {2010), 31(6):212-219.
James; et al. "A unique clonal JAK2 mutation leading to constitutive signaling causes polycythaemia vera", Nature (Jun.-Jul. 2005), 434:1144-1148.
Jamieson et al., "Increased Ecpression of CD47 is a Constant Marker in Mouse and Human Myelodi Leukemias" Blood (ASH Annual Meeting Abstracts) 2005, pp. 1-2, 106, Abstract 3260, American Society of Hematology, Washington, DC.
Jamieson et al. "Chronic versus acute myelogenous leukemia: A question of self-renewal", Cancer Cell (Dec. 2004), 6(6):531-533.
Jamieson et al. "Granulocyte-macrophage progenitors as candidate leukemic stem cells in blast-crisis CML", New England Journal of Medicine (Aug. 2004), 351(7):657-667.
Jan et al., "Prospective separation of normal and leukemic stem cells based on differential expression of TIM3, a human acute myeloid leukemia stem cell marker", PNAS (Mar. 2011 ). 108(12):5009-5014.
Jin et al. "Targeting of CD44 eradicates human acute myeloid leukemic stem cells", Nat Med (Oct. 2006), 12(10)1167-1174.
Kaiser et al., Expression of insulin-like growth factor receptors I and II in normal human lung and in lunch cancer, J Cancer Res Clin Oneal, 119:665-668, Feb. 19, 1993.
Karp et al., "Targeting Vascular Endothelial Growth Factor for Relapsed and Refractory Adult Scute Myelogenous Leukemias: Therapy with Sequential 1-fJ-D-Arabinofuranosylcytosine, Mitoxantrone, and Bevacizumab", Clinical Cancer Research, Jun. 1, 2004, pp. 3577-3585, vol. 10, American Association for Cancer Research, Philadelphia, PA.
Kikuhige et al. "TIM-3 Is a Promising Target to Selectively Kill Acute Myeloid Leukemia Stem Cells", Cell Stem Cell, (Dec. 2010), 7(6):708-717.
Kim et al., "Antibody Engineering for the Development of Therapeutic Antibodies", Molecules and Cells, Aug. 18, 2005, pp. 17-29, vol. 20, No. 1, Korean Society for Molecular and Cellular Biology, Seoul, Korea.
Kovacsovics-Bankowski et al., "Efficient major histocompatibility complex class I presentation of exogenous antigen upon phagocytosis by macrophages", Proc. Natl. Acad. Sci., 1993, pp. 4942-4946, vol. 90, PNAS, Washington, DC.
Kravolics et al. "A gain-of-function mutation of JAK2 in myeloproliferative disorders", New England Journal of Medicine (2005), 352(17)1779-1790.
Levine et al. "Activating mutation in the tyrosine kinase JAK2 in polycythemia vera, essential thrombocythemia, and myeloid metaplasia with myelofibrosis", Cancer Cell (2005), 7:387-397.
Liu et al. "Signal Regulatory Protein (SIRalpha), a Cellular Ligand for CD47, Regulates Neutrophil Transmigration", Journal of Biological Chemistry (Mar. 2002), 227 ( 12): 10028-10036.
Tioma Therapeutics, Inc., Notice of Opposition to European Patent EP2242512, Jan. 20, 2017, pp. 1-10.
Blink Biomedical SAS, Notice of Opposition to European Patent EP2242512, Jan. 26, 2017, pp. 1-42.

(56) References Cited

OTHER PUBLICATIONS

Bristol-Myers Squibb Company, Notice of Opposition to to European Patent European Patent EP2242512, Jan. 26, 2017, pp. 1-29.
Avidity IP Limited, Notice of Opposition to European Patent EP2242512, Jan. 26, 2017, pp. 1-36.
Wilding, Notice of Opposition to European Patent EP2242512, Jan. 26, 2017, pp. 1-52.
Surface Oncology, Inc., Notice of Opposition to European Patent EP2242512, Jan. 27, 2017, pp. 1-45.
Strawman Limited, Notice of Opposition to European Patent EP2242512, Jan. 27, 2017, pp. 1-36.

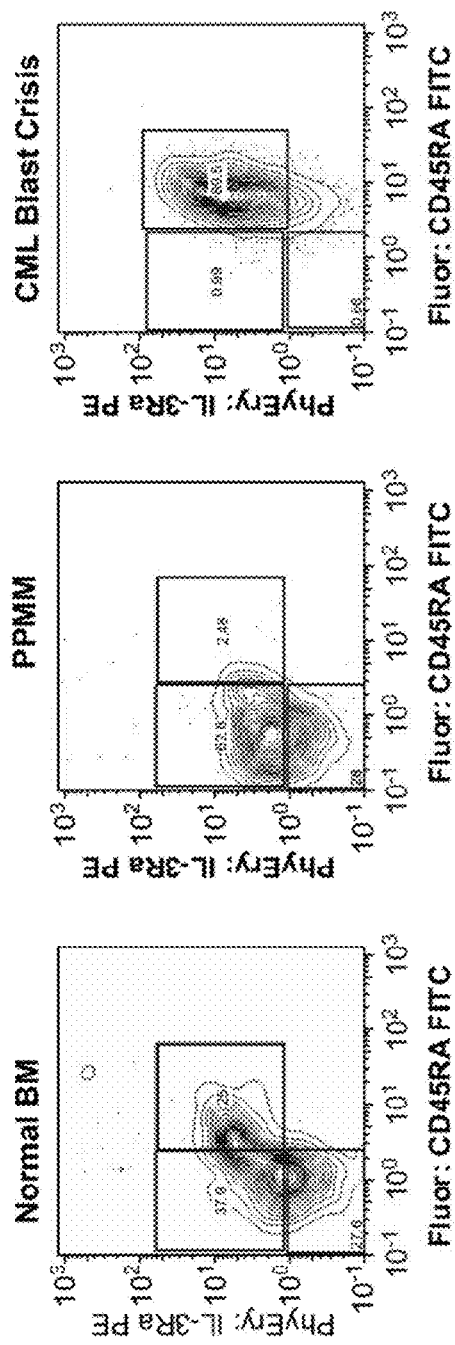
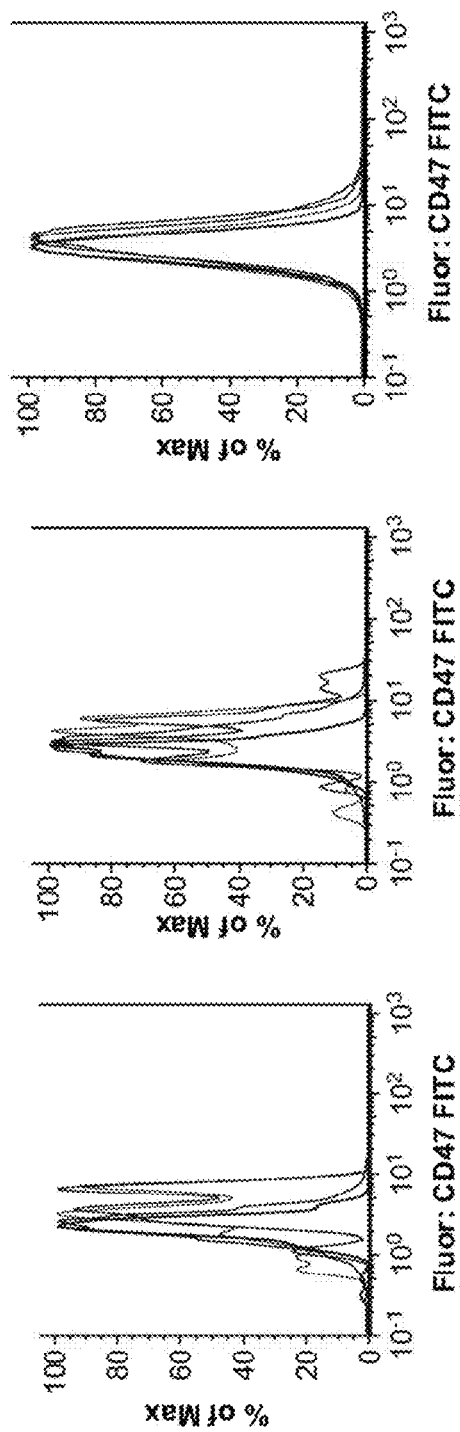
FIG. 3A
FIG. 3B

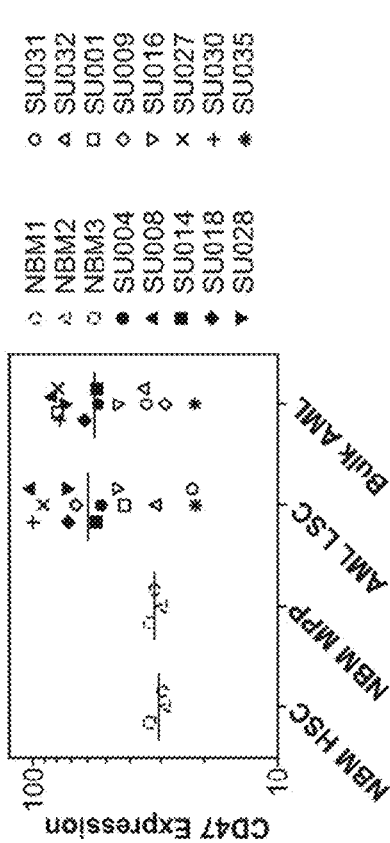

| Sample | Age | Gender | Primary/Secondary | De Novo/Relapsed | Cytogenetics | Flt-3 ITD | % CD34 | WHO Classification | FAB |
|---|---|---|---|---|---|---|---|---|---|
| SU001 | 59 | Female | Primary | Relapsed | Normal | Negative | 99 | AML not-otherwise specified | M2 |
| SU004 | 47 | Female | Primary | Relapsed | Normal | Positive | 38 | AML not-otherwise specified | M5 |
| SU008 | 64 | Male | Primary | De Novo | Normal | Positive | 3 | AML not-otherwise specified | M1 |
| SU009 | 43 | Male | Primary | De Novo | Normal | Negative | 73 | AML with multilineage dysplasia without antecedent MDS | M2 |
| SU014 | 59 | Male | Primary | De Novo | Normal | Positive | 18 | AML not-otherwise specified | NS |
| SU016 | 59 | Male | Primary | De Novo | Normal | Positive | 10 | AML with multilineage dysplasia without antecedent MDS | NS |
| SU018 | 21 | Male | Primary | Relapsed | Normal | Positive | 55 | AML not-otherwise specified | M5 |
| SU027 | 61 | Male | Primary | Relapsed | Failed to grow | Unknown | 10 | AML not-otherwise specified | M5 |
| SU028 | 53 | Female | Primary | Relapsed | Complex | Positive | 50 | AML not-otherwise specified | M5 |
| SU030 | 53 | Female | Primary | De Novo | Normal | Positive | 40 | AML with multilineage dysplasia without antecedent MDS | M4 |
| SU031 | 31 | Female | Primary | De Novo | inv(16)(p13;q22) | Negative | 97 | AML with inv(16)(p13;q22) or t(16;16)(p13;q22) | M4eo |
| SU032 | 47 | Male | Primary | De Novo | Normal | Negative | 68 | AML not-otherwise specified | M5 |
| SU035 | 46 | Male | Primary | De Novo | Failed to grow | Negative | 98 | AML not-otherwise specified | M5 |

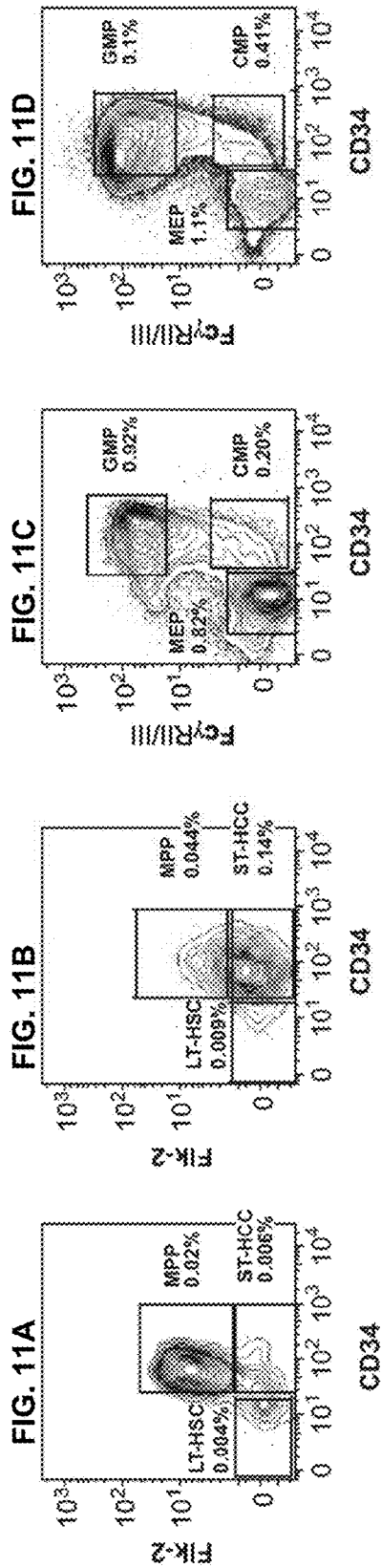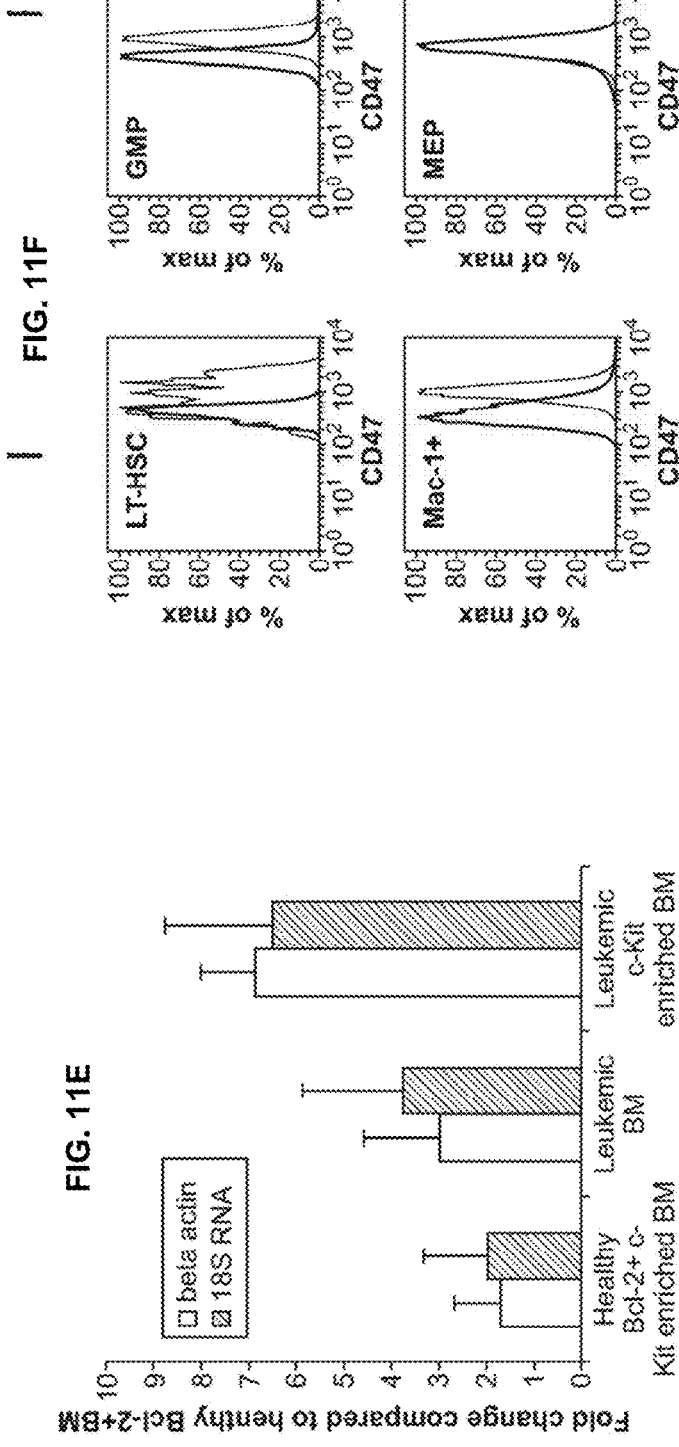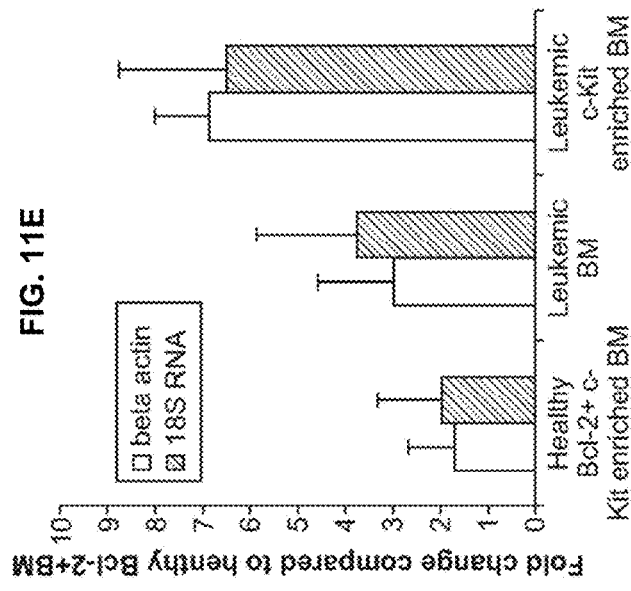

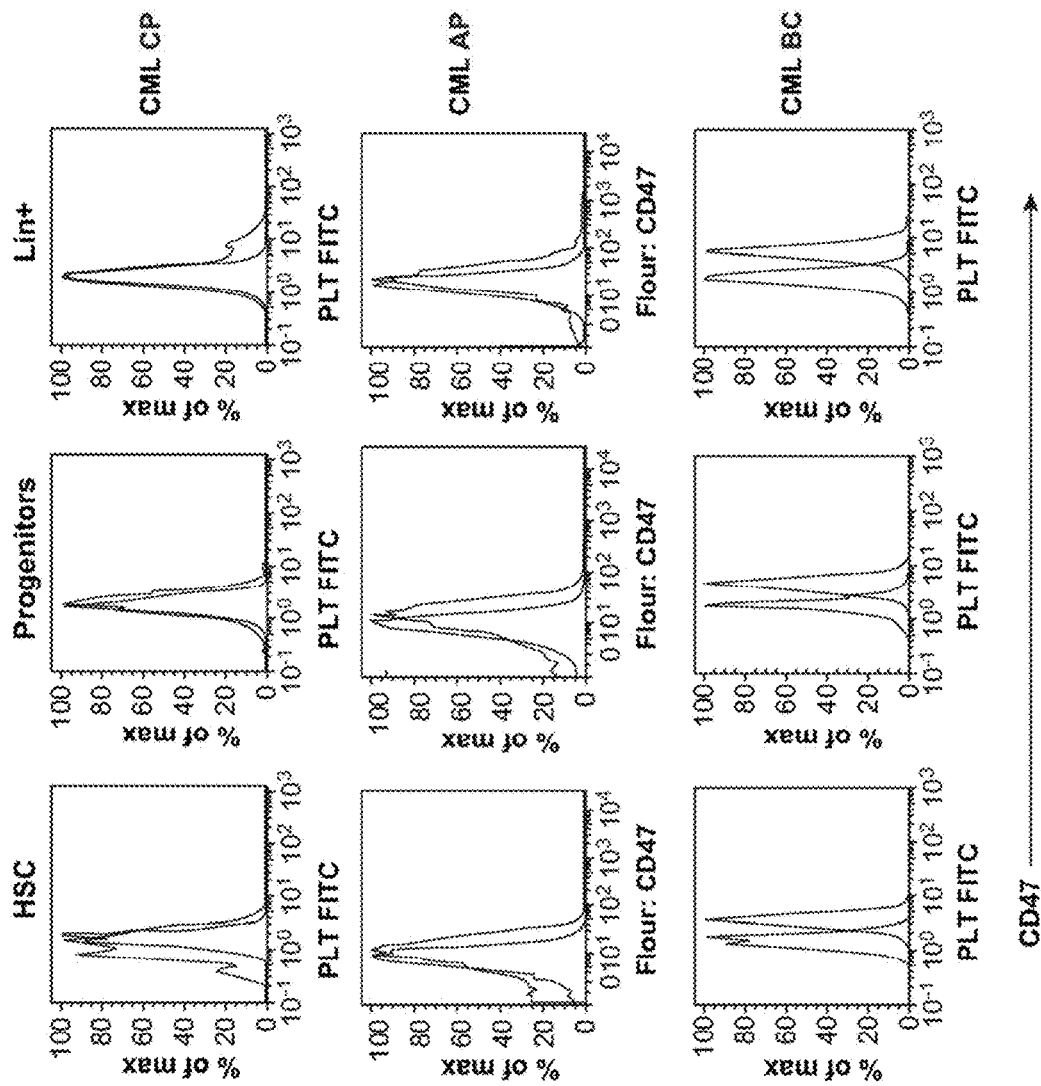

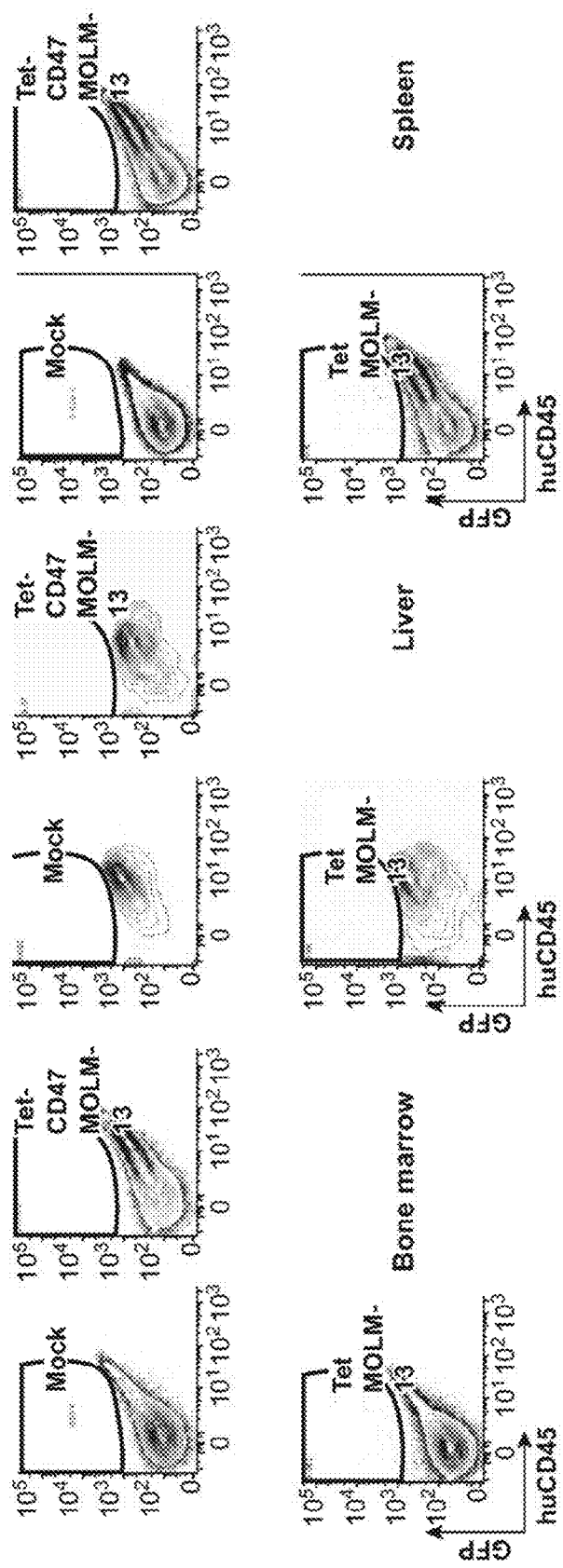

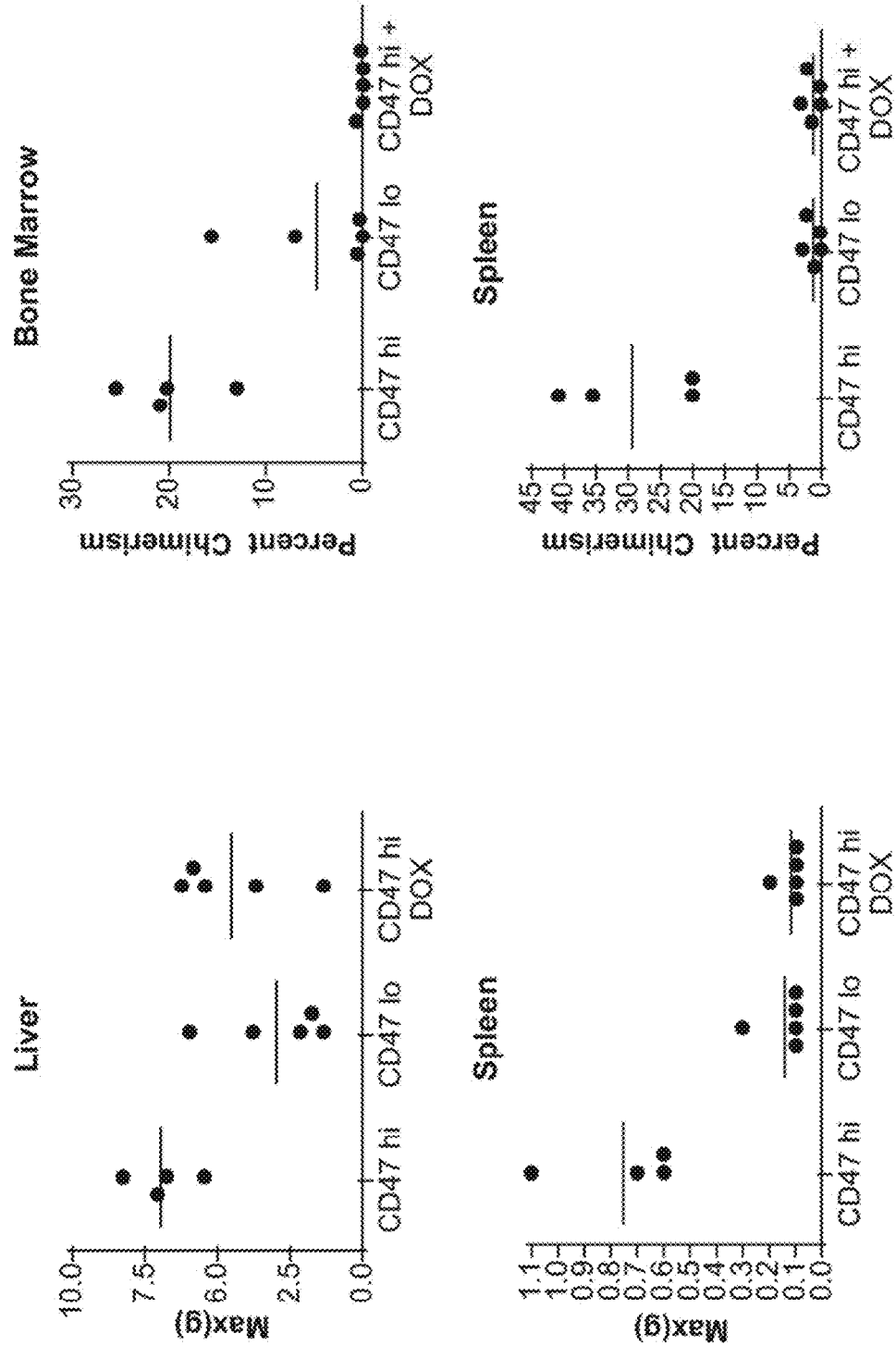

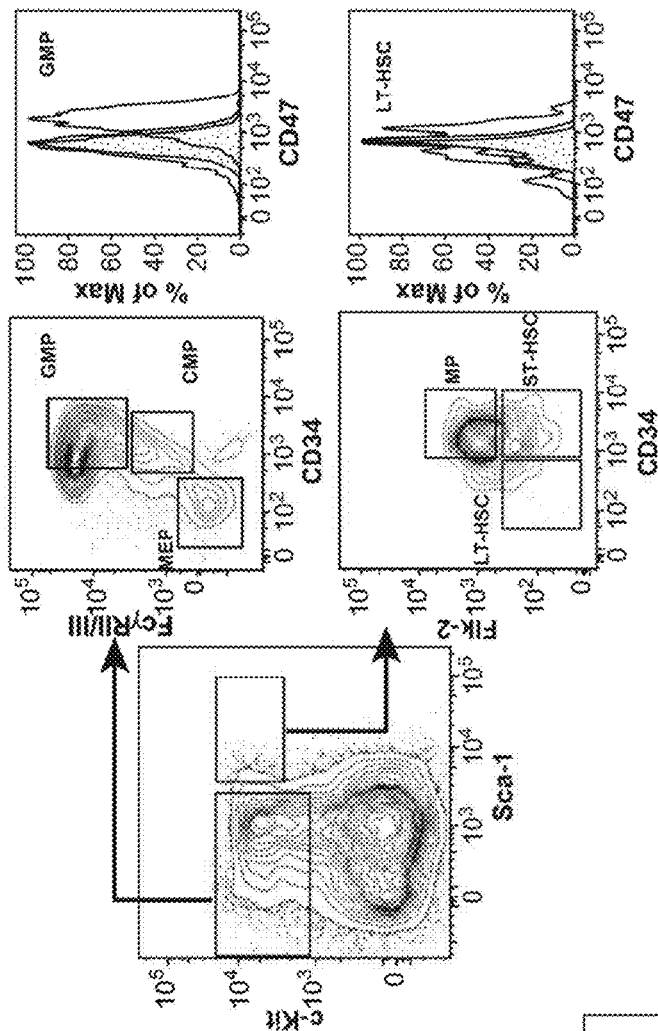
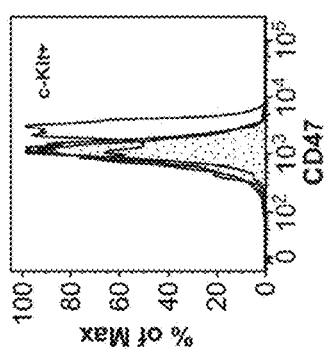
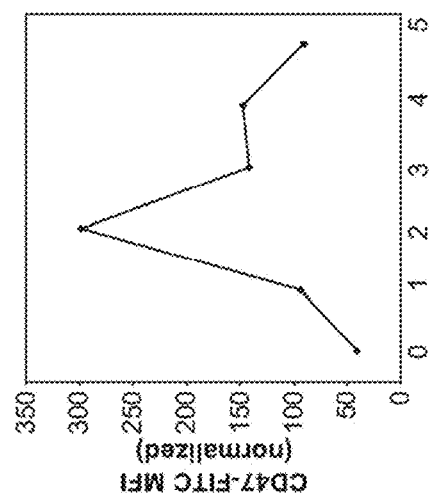
FIG. 19B
FIG. 19A
FIG. 19C

FIG. 26A
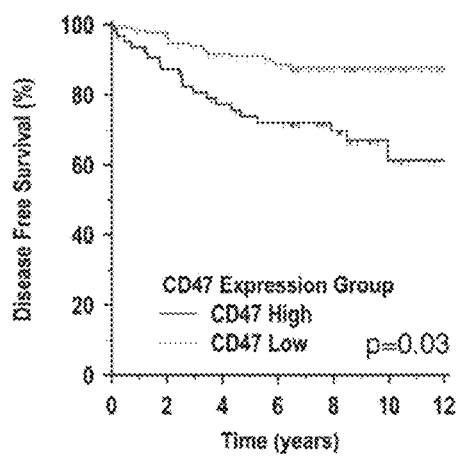
FIG. 26B
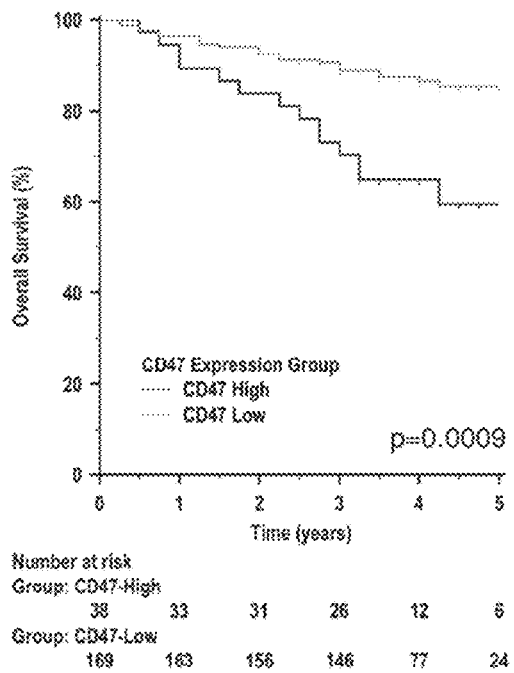
FIG. 26C
| Outcome Measure | HR | 95% CI | P |
|---|---|---|---|
| CD47 expression, continuous | 2.64 | 1.08 – 6.51 | 0.035 |
| Age at diagnosis | 1.03 | 0.97 – 1.11 | 0.028 |
| Gender | 0.89 | 0.42 – 1.91 | 0.771 |
| WBC count | 2.09 | 1.10 – 3.98 | 0.025 |
| CNS disease involvement | 1.21 | 0.56 – 2.68 | 0.632 |
| Minimal Residual Disease | 2.97 | 1.48 – 5.96 | 0.002 |
FIG. 26D
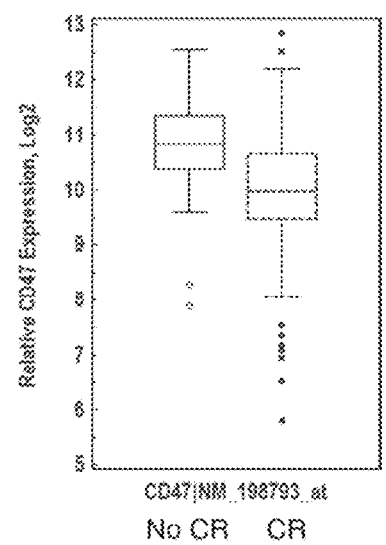

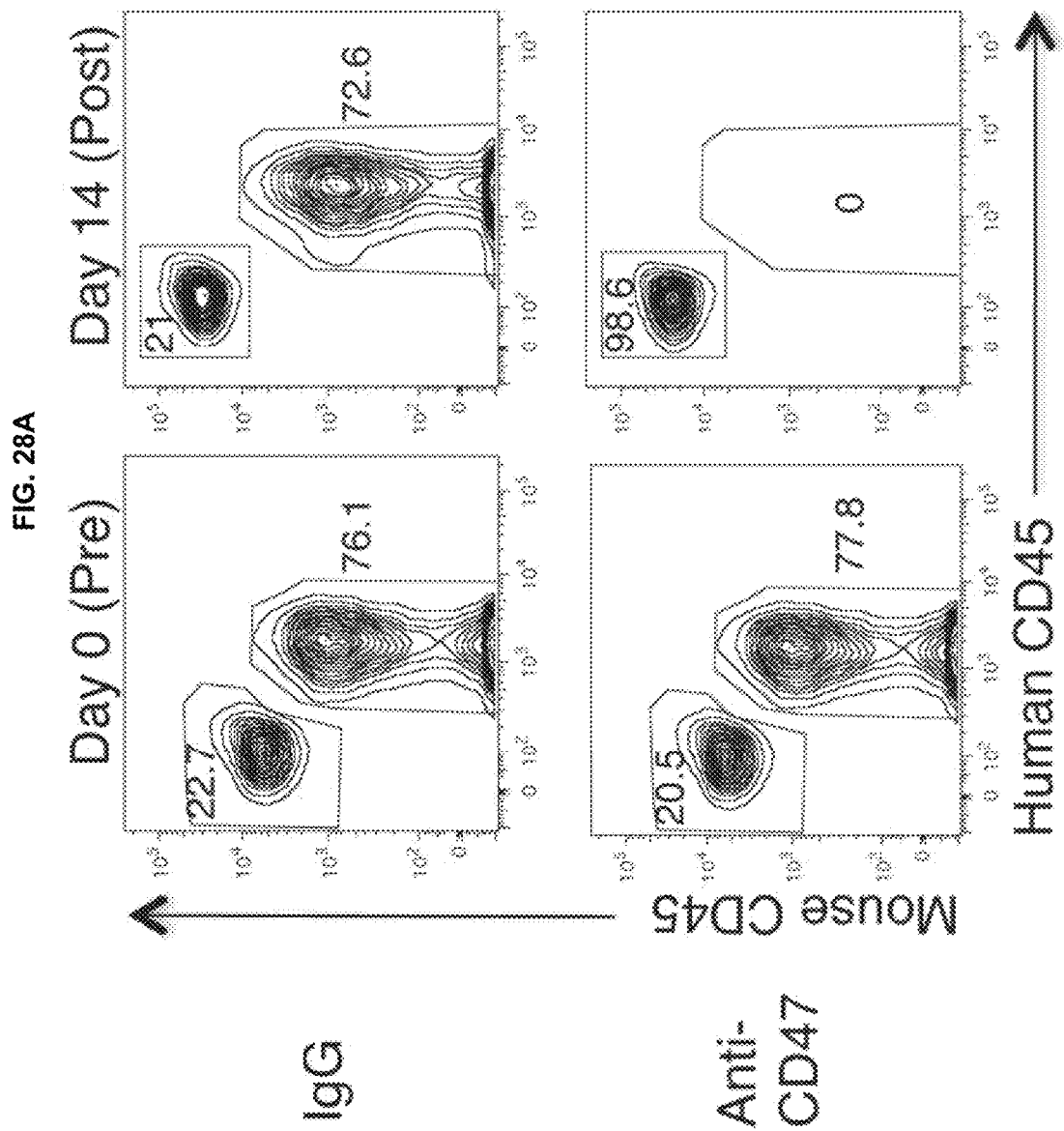

FIG. 31A
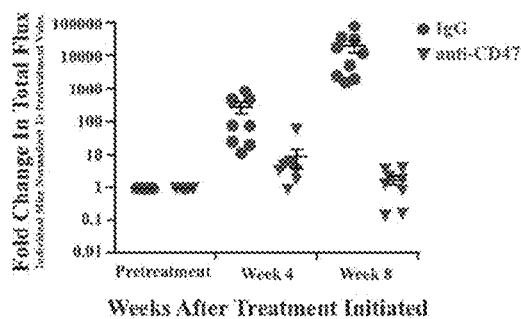
FIG. 31B
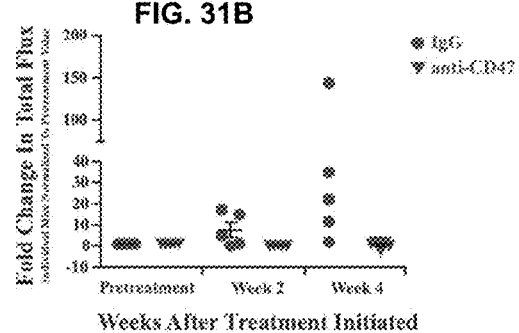
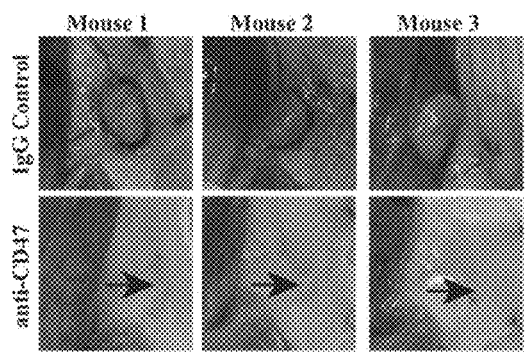
FIG. 31C
FIG. 31D
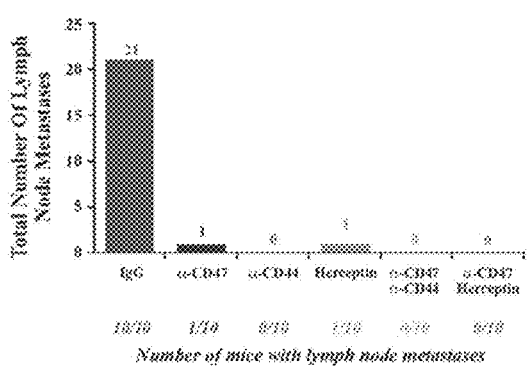
FIG. 31E
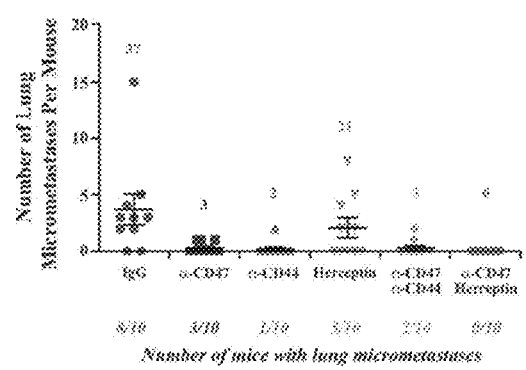
FIG. 31F

SEQUENCE LISTING

```
<160> NUMBER OF SEQ ID NOS: 18

<210> SEQ ID NO 1
<211> LENGTH: 142
<212> TYPE: PRT
<213> ORGANISM: Homo sapiens

<400> SEQUENCE: 1

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn
    130                 135                 140

<210> SEQ ID NO 2
<211> LENGTH: 5346
<212> TYPE: DNA
<213> ORGANISM: Homo sapiens
```

<400> SEQUENCE: 2

```
ggggagcagg cggggagcg ggcgggaagc agtgggagcg cgcgtgcgcg cggccgtgca      60
gcctgggcag tgggtcctgc ctgtgacgcg cggcggcggt cggtcctgcc tgtaacggcg     120
gcggcggctg ctgctccaga cacctgcggc ggcggcggcg accccgcggc gggcgcggag     180
atgtggcccc tggtagcggc gctgttgctg ggctcggcgt gctgcggatc agctcagcta     240
ctatttaata aaacaaaatc tgtagaattc acgttttgta atgacactgt cgtcattcca     300
tgctttgtta ctaatatgga ggcacaaaac actactgaag tatacgtaaa gtggaaattt     360
aaaggaagag atatttacac ctttgatgga gctctaaaca agtccactgt ccccactgac     420
tttagtagtg caaaaattga agtctcacaa ttactaaaag gagatgcctc tttgaagatg     480
gataagagtg atgctgtctc acacacagga aactacactt gtgaagtaac agaattaacc     540
agagaaggtg aaacgatcat cgagctaaaa tatcgtgttg tttcatggtt ttctccaaat     600
gaaaatattc ttattgttat tttcccaatt tttgctatac tcctgttctg gggacagttt     660
ggtattaaaa cacttaaata tagatccggt ggtatggatg agaaaacaat tgctttactt     720
gttgctggac tagtgatcac tgtcattgtc attgttggag ccattctttt cgtcccaggt     780
gaatattcat taaagaatgc tactggcctt ggtttaattg tgacttctac agggatatta     840
atattacttc actactatgt gtttagtaca gcgattggat taacctcctt cgtcattgcc     900
atattggtta ttcaggtgat agcctatatc ctcgctgtgg ttggactgag tctctgtatt     960
gcggcgtgta taccaatgca tggccctctt ctgatttcag gtttgagtat cttagctcta    1020
gcacaattac ttggactagt ttatatgaaa tttgtggctt ccaatcagaa gactatacaa    1080
cctcctagga aagctgtaga ggaaccccct aatgcattca agaatcaaa aggaatgatg    1140
aatgatgaat aactgaagtg aagtgatgga ctccgatttg gagagtagta agacgtgaaa    1200
ggaatacact tgtgtttaag caccatggcc ttgatgattc actgttgggg agaagaaaca    1260
agaaaagtaa ctggttgtca cctatgagac ccttacgtga ttgttagtta agttttatt    1320
caaagcagct gtaatttagt taataaaata attatgatct atgttgtttg cccaattgag    1380
atccagtttt ttgttgttat ttttaatcaa ttaggggcaa tagtagaatg gacaatttcc    1440
aagaatgatg cctttcaggt cctagggcct ctggcctcta ggtaaccagt ttaaattggt    1500
tcagggtgat aactacttag cactgccctg gtgattaccc agagatatct atgaaaacca    1560
gtggcttcca tcaaaccttt gccaactcag gttcacagca gctttgggca gttatggcag    1620
tatggcatta gctgagaggt gtctgccact tctgggtcaa tggaataata aattaagtac    1680
aggcaggaat ttggttggga gcatcttgta tgatctccgt atgatgtgat attgatggag    1740
atagtggtcc tcattcttgg gggttgccat tcccacattc ccccttcaac aaacagtgta    1800
acaggtcctt cccagattta gggtactttt attgatggat atgttttcct tttattcaca    1860
taaccccttg aaaccctgtc ttgtcctcct gttacttgct tctgctgtac aagatgtagc    1920
accttttctc ctctttgaac atggtctagt gacacggtag caccagttgc aggaaggagc    1980
cagacttgtt ctcagagcac tgtgttcaca cttttcagca aaaatagcta tggttgtaac    2040
atatgtattc ccttcctctg atttgaaggc aaaaatctac agtgtttctt cacttctttt    2100
ctgatctggg gcatgaaaaa agcaagattg aaatttgaac tatgagtctc ctgcatggca    2160
acaaaatgtg tgtcaccatc aggccaacag gccagccctt gaatggggat ttattactgt    2220
tgtatctatg ttgcatgata aacattcatc accttcctcc tgtagtcctg cctcgtactc    2280
```

```
cccttcccct atgattgaaa agtaaacaaa acccacattt cctatcctgg ttagaagaaa    2340
attaatgttc tgacagttgt gatcgcctgg agtactttta gacttttagc attcgttttt    2400
tacctgtttg tggatgtgtg tttgtatgtg catacgtatg agataggcac atgcatcttc    2460
tgtatggaca aaggtggggt acctacagga gagcaaggt taattttgtg cttttagtaa     2520
aaacatttaa atacaaagtt ctttattggg tggaattata tttgatgcaa atatttgatc    2580
acttaaaact tttaaaactt ctaggtaatt tgccacgctt tttgactgct caccaatacc    2640
ctgtaaaaat acgtaattct tcctgtttgt gtaataagat attcatattt gtagttgcat    2700
taataatagt tatttcttag tccatcagat gttcccgtgt gcctctttta tgccaaattg    2760
attgtcatat ttcatgttgg gaccaagtag tttgcccatg gcaaacctaa atttatgacc    2820
tgctgaggcc tctcagaaaa ctgagcatac tagcaagaca gctcttcttg aaaaaaaaaa    2880
tatgtataca caaatatata cgtatatcta tatatacgta tgtatataca cacatgtata    2940
ttcttccttg attgtgtagc tgtccaaaat aataacatat atagagggag ctgtattcct    3000
ttatacaaat ctgatggctc ctgcagcact ttttccttct gaaaatattt acattttgct    3060
aacctagttt gttactttaa aaatcagttt tgatgaaagg agggaaaagc agatggactt    3120
gaaaaagatc caagctccta ttagaaaagg tatgaaaatc tttatagtaa aatttttat     3180 aaactaaagt tgtaccttt aatatgtagt aaactctcat ttatttgggg ttcgctcttg     3240
gatctcatcc atccattgtg ttctctttaa tgctgcctgc cttttgaggc attcactgcc    3300
ctagacaatg ccaccagaga tagtggggga aatgccagat gaaaccaact cttgctctca    3360
ctagttgtca gcttctctgg ataagtgacc acagaagcag gagtcctcct gcttgggcat    3420
cattgggcca gttccttctc tttaaatcag atttgtaatg gctcccaaat tccatcacat    3480
cacatttaaa ttgcagacag tgttttgcac atcatgtatc tgttttgtcc cataatatgc    3540
tttttactcc ctgatcccag tttctgctgt tgactcttcc attcagtttt atttattgtg    3600
tgttctcaca gtgacaccat ttgtcctttt ctgcaacaac cttccagct actttgcca      3660 aattctattt gtcttctcct tcaaaacatt ctcctttgca gttcctcttc atctgtgtag    3720
ctgctctttt gtctcttaac ttaccattcc tatagtactt tatgcatctc tgcttagttc    3780 tattagttt ttggccttgc tcttctcctt gattttaaaa ttccttctat agctagagct     3840
tttctttctt tcattctctc ttcctgcagt gttttgcata catcagaagc taggtacata    3900
agttaaatga ttgagagttg gctgtattta gatttatcac ttttaatag ggtgagcttg     3960 agagttttct ttctttctgt ttttttttt tgtttttttt tttttttttt tttttttttt     4020
ttttgactaa tttcacatgc tctaaaaacc ttcaaggtg attattttc tcctggaaac      4080 tccaggtcca ttctgtttaa atccctaaga atgtcagaat taaataaca gggctatccc     4140 gtaattggaa atatttcttt tttcaggatg ctatagtcaa tttagtaagt gaccaccaaa    4200
ttgttatttg cactaacaaa gctcaaaaca cgataagttt actcctccat ctcagtaata    4260
aaaattaagc tgtaatcaac cttctaggtt tctcttgtct taaaatgggt attcaaaaat    4320
ggggatctgt ggtgtatgta tggaaacaca tactccttaa tttacctgtt gttggaaact    4380
ggagaaatga ttgtcgggca accgttatt ttttattgta ttttattgg ttgagggatt      4440 tttttataaa cagttttact tgtgtcatat tttaaaatta ctaactgcca tcacctgctg    4500
gggtcctttg ttaggtcatt ttcagtgact aataggata atccaggtaa ctttgaagag    4560
atgagcagtg agtgaccagg cagttttcct gcctttagct ttgacagttc ttaattaaga    4620
tcattgaaga ccagctttct cataaatttc tctttttgaa aaaagaaag catttgtact     4680
```

```
aagctcctct gtaagacaac atcttaaatc ttaaaagtgt tgttatcatg actggtgaga    4740
gaagaaaaca ttttgttttt attaaatgga gcattattta caaaaagcca ttgttgagaa    4800
ttagatccca catcgtataa atatctatta accattctaa ataaagagaa ctccagtgtt    4860
gctatgtgca agatcctctc ttggagcttt tttgcatagc aattaaaggt gtgctatttg    4920
tcagtagcca ttttttttgca gtgatttgaa gaccaaagtt gttttacagc tgtgttaccg    4980
ttaaaggttt tttttttttat atgtattaaa tcaatttatc actgtttaaa gctttgaata    5040
tctgcaatct tgccaaggt acttttttat ttaaaaaaaa acataacttt gtaaatatta    5100
ccctgtaata ttatatatac ttaataaaac attttaagct attttgttgg gctatttcta    5160
ttgctgctac agcagaccac aagcacattt ctgaaaaatt taatttatta atgtattttt    5220
aagttgctta tattctaggt aacaatgtaa agaatgattt aaaatattaa ttatgaattt    5280
tttgagtata atacccaata agcttttaat tagagcagag ttttaattaa aagttttaaa    5340
tcagtc                                                               5346
```

<210> SEQ ID NO 3
<211> LENGTH: 5288
<212> TYPE: DNA
<213> ORGANISM: Homo sapiens

<400> SEQUENCE: 3

```
ggggagcagg cgggggagcg ggcgggaagc agtgggagcg cgcgtgcgcg cggccgtgca      60
gcctgggcag tgggtcctgc ctgtgacgcg cggcggcggt cggtcctgcc tgtaacggcg     120
gcggcggctg ctgctccaga cacctgcggc ggcggcggcg accccgcggc gggcgcggag     180
atgtggcccc tggtagcggc gctgttgctg ggctcggcgt gctgcggatc agctcagcta     240
ctatttaata aaacaaaatc tgtagaattc acgttttgta atgacactgt cgtcattcca     300
tgctttgtta ctaatatgga ggcacaaaac actactgaag tatacgtaaa gtggaaattt     360
aaaggaagag atatttacac ctttgatgga gctctaaaca agtccactgt ccccactgac     420
tttagtagtg caaaaattga agtctcacaa ttactaaaag gagatgcctc tttgaagatg     480
gataagagtg atgctgtctc acacacagga aactacactt gtgaagtaac agaattaacc     540
agagaaggtg aaacgatcat cgagctaaaa tatcgtgttg tttcatggtt ttctccaaat     600
gaaaatattc ttattgttat tttcccaatt tttgctatac tcctgttctg gggacagttt     660
ggtattaaaa cacttaaata tagatccggt ggtatggatg agaaaacaat tgctttactt     720
gttgctggac tagtgatcac tgtcattgtc attgttggag ccattctttt cgtcccaggt     780
gaatattcat taagaatgc tactggcctt ggtttaattg tgacttctac agggatatta     840
atattacttc actactatgt gtttagtaca gcgattggat taacctcctt cgtcattgcc     900
atattggtta ttcaggtgat agcctatatc ctcgctgtgg ttggactgag tctctgtatt     960
gcggcgtgta taccaatgca tggccctctt ctgatttcag gtttgagtat cttagctcta    1020
gcacaattac ttggactagt ttatatgaaa tttgtggctt ccaatcagaa gactatacaa    1080
cctcctagga ataactgaag tgaagtgatg gactccgatt tggagagtag taagacgtga    1140
aaggaataca cttgtgttta agcaccatgg ccttgatgat tcactgttgg ggagaagaaa    1200
caagaaaagt aactggttgt cacctatgag acccttacgt gattgttagt taagttttta    1260
ttcaaagcag ctgtaattta gttaataaaa taattatgat ctatgttgtt tgcccaattg    1320
agatccagtt ttttgttgtt attttttaatc aattaggggc aatagtagaa tggacaattt    1380
```

-continued

```
ccaagaatga tgcctttcag gtcctagggc ctctggcctc taggtaacca gtttaaattg    1440
gttcagggtg ataactactt agcactgccc tggtgattac ccagagatat ctatgaaaac    1500
cagtggcttc catcaaacct tgccaactc aggttcacag cagctttggg cagttatggc     1560
agtatggcat tagctgagag gtgtctgcca cttctgggtc aatggaataa taaattaagt    1620
acaggcagga atttggttgg gagcatcttg tatgatctcc gtatgatgtg atattgatgg    1680
agatagtggt cctcattctt gggggttgcc attcccacat tcccccttca acaaacagtg    1740
taacaggtcc ttcccagatt tagggtactt ttattgatgg atatgttttc cttttattca    1800
cataacccct tgaaaccctg tcttgtcctc ctgttacttg cttctgctgt acaagatgta    1860
gcaccttttc tcctctttga acatggtcta gtgacacggt agcaccagtt gcaggaagga    1920
gccagacttg ttctcagagc actgtgttca cacttttcag caaaaatagc tatggttgta    1980
acatatgtat tcccttcctc tgatttgaag gcaaaaatct acagtgtttc ttcacttctt    2040
ttctgatctg gggcatgaaa aaagcaagat tgaaatttga actatgagtc tcctgcatgg    2100
caacaaaatg tgtgtcacca tcaggccaac aggccagccc ttgaatgggg atttattact    2160
gttgtatcta tgttgcatga taaacattca tcaccttcct cctgtagtcc tgcctcgtac    2220
tccccttccc ctatgattga aaagtaaaca aaacccacat ttcctatcct ggttagaaga    2280
aaattaatgt tctgacagtt gtgatcgcct ggagtacttt tagacttttta gcattcgttt    2340 tttacctgtt tgtggatgtg tgtttgtatg tgcatacgta tgagataggc acatgcatct    2400
tctgtatgga caaaggtggg gtacctacag gagagcaaag gttaattttg tgcttttagt    2460
aaaaacattt aaatacaaag ttctttattg ggtggaatta tatttgatgc aaatatttga    2520
tcacttaaaa cttttaaaac ttctaggtaa tttgccacgc ttttttgactg ctcaccaata    2580 ccctgtaaaa atacgtaatt cttcctgttt gtgtaataag atattcatat ttgtagttgc    2640
attaataata gttatttctt agtccatcag atgttcccgt gtgcctcttt tatgccaaat    2700
tgattgtcat atttcatgtt gggaccaagt agtttgccca tggcaaacct aaatttatga    2760
cctgctgagg cctctcagaa aactgagcat actagcaaga cagctcttct tgaaaaaaaa    2820
aatatgtata cacaaatata tacgtatatc tatatatacg tatgtatata cacacatgta    2880
tattcttcct tgattgtgta gctgtccaaa ataataacat atatagaggg agctgtattc    2940
ctttatacaa atctgatggc tcctgcagca cttttttcctt ctgaaaatat ttacattttg    3000
ctaacctagt ttgttacttt aaaaatcagt tttgatgaaa ggagggaaaa gcagatggac    3060
ttgaaaaaga tccaagctcc tattagaaaa ggtatgaaaa tctttatagt aaaattttt    3120 ataaactaaa gttgtacctt ttaatatgta gtaaactctc atttatttgg ggttcgctct    3180
tggatctcat ccatccattg tgttctcttt aatgctgcct gccttttgag gcattcactg    3240
ccctagacaa tgccaccaga gatagtgggg gaaatgccag atgaaaccaa ctcttgctct    3300
cactagttgt cagcttctct ggataagtga ccacagaagc aggagtcctc ctgcttgggc    3360
atcattgggc cagttccttc tctttaaatc agatttgtaa tggctcccaa attccatcac    3420
atcacattta aattgcagac agtgttttgc acatcatgta tctgttttgt cccataatat    3480 gcttttttact ccctgatccc agtttctgct gttgactctt ccattcagtt ttatttattg    3540
tgtgttctca cagtgacacc atttgtcctt ttctgcaaca acctttccag ctactttgc    3600 caaattctat ttgtcttctc cttcaaaaca ttctcctttg cagttcctct tcatctgtgt    3660
agctgctctt ttgtctctta acttaccatt cctatagtac tttatgcatc tctgcttagt    3720
tctattagtt ttttggcctt gctcttctcc ttgattttaa aattccttct atagctagag    3780
```

```
cttttctttc tttcattctc tcttcctgca gtgttttgca tacatcagaa gctaggtaca    3840
taagttaaat gattgagagt tggctgtatt tagatttatc acttttaat agggtgagct     3900
tgagagtttt ctttctttct gttttttttt tttgttttt tttttttttt ttttttttt     3960
tttttgact aatttcacat gctctaaaaa ccttcaaagg tgattatttt tctcctggaa    4020
actccaggtc cattctgttt aaatccctaa gaatgtcaga attaaaataa cagggctatc   4080
ccgtaattgg aaatatttct ttttttcagga tgctatagtc aatttagtaa gtgaccacca  4140
aattgttatt tgcactaaca aagctcaaaa cacgataagt ttactcctcc atctcagtaa   4200
taaaaattaa gctgtaatca accttctagg tttctcttgt cttaaaatgg gtattcaaaa   4260
atggggatct gtggtgtatg tatggaaaca catactcctt aatttacctg ttgttggaaa   4320
ctggagaaat gattgtcggg caaccgttta tttttttattg tattttatttt ggttgaggga 4380
ttttttata aacagtttta cttgtgtcat attttaaaat tactaactgc catcacctgc   4440
tggggtcctt tgttaggtca ttttcagtga ctaatgggga taatccaggt aactttgaag   4500
agatgagcag tgagtgacca ggcagttttt ctgcctttag ctttgacagt tcttaattaa   4560
gatcattgaa gaccagcttt ctcataaatt tctcttttg aaaaaaagaa agcatttgta   4620
ctaagctcct ctgtaagaca acatcttaaa tcttaaaagt gttgttatca tgactggtga   4680
gagaagaaaa catttgttt ttattaaatg gagcattatt tacaaaaagc cattgttgag   4740
aattagatcc cacatcgtat aaatatctat taaccattct aaataaagag aactccagtg   4800
ttgctatgtg caagatcctc tcttggagct tttttgcata gcaattaaag gtgtgctatt   4860
tgtcagtagc catttttttg cagtgatttg aagaccaaag ttgttttaca gctgtgttac   4920
cgttaaaggt tttttttttt atatgtatta aatcaattta tcactgttta aagctttgaa   4980
tatctgcaat ctttgccaag gtactttttt atttaaaaaa aacataact ttgtaaatat    5040
taccctgtaa tattatatat acttaataaa acatttaag ctattttgtt gggctatttc   5100
tattgctgct acagcagacc acaagcacat ttctgaaaaa tttaatttat taatgtatt    5160
ttaagttgct tatattctag gtaacaatgt aaagaatgat ttaaaatatt aattatgaat   5220
tttttgagta taataccccaa taagcttta attagagcag agttttaatt aaaagttta    5280
aatcagtc                                                             5288
```

<210> SEQ ID NO 4
<211> LENGTH: 5313
<212> TYPE: DNA
<213> ORGANISM: Homo sapiens

<400> SEQUENCE: 4

```
ggggagcagg cggggagcg ggcgggaagc agtgggagcg cgcgtgcgcg cggccgtgca      60
gcctgggcag tgggtcctgc ctgtgacgcg cggcggcggt cggtcctgcc tgtaacggcg    120
gcggcggctg ctgctccaga cacctgcggc ggcggcggcg accccgcggc gggcgcggag    180
atgtggcccc tggtagcggc gctgttgctg ggctcggcgt gctgcggatc agctcagcta    240
ctatttaata aaacaaaatc tgtagaattc acgttttgta atgacactgt cgtcattcca    300
tgctttgtta ctaatatgga ggcacaaaac actactgaag tatacgtaaa gtggaaattt    360
aaaggaagag atatttacac ctttgatgga gctctaaaca agtccactgt ccccactgac    420
tttagtagtg caaaaattga agtctcacaa ttactaaaag gagatgcctc tttgaagatg   480
gataagagtg atgctgtctc acacacagga aactacactt gtgaagtaac agaattaacc   540
```

```
agagaaggtg aaacgatcat cgagctaaaa tatcgtgttg tttcatggtt ttctccaaat    600
gaaaatattc ttattgttat tttcccaatt tttgctatac tcctgttctg gggacagttt    660
ggtattaaaa cacttaaata tagatccggt ggtatggatg agaaaacaat tgctttactt    720
gttgctggac tagtgatcac tgtcattgtc attgttggag ccattctttt cgtcccaggt    780
gaatattcat taaagaatgc tactggcctt ggtttaattg tgacttctac agggatatta    840
atattacttc actactatgt gtttagtaca gcgattggat taacctcctt cgtcattgcc    900
atattggtta ttcaggtgat agcctatatc ctcgctgtgg ttggactgag tctctgtatt    960
gcggcgtgta taccaatgca tggccctctt ctgatttcag gtttgagtat cttagctcta   1020
gcacaattac ttggactagt ttatatgaaa tttgtggctt ccaatcagaa gactatacaa   1080
cctcctagga aagctgtaga ggaaccccct aatgaataac tgaagtgaag tgatggactc   1140
cgatttggag agtagtaaga cgtgaaagga atacacttgt gtttaagcac catggccttg   1200
atgattcact gttggggaga agaaacaaga aaagtaactg ttgtcaccct atgagaccct   1260
tacgtgattg ttagttaagt ttttattcaa agcagctgta atttagttaa taaataatt    1320
atgatctatg ttgtttgccc aattgagatc cagttttttg ttgttatttt taatcaatta   1380
ggggcaatag tagaatggac aatttccaag aatgatgcct ttcaggtcct agggcctctg   1440
gcctctaggt aaccagttta aattggttca gggtgataac tacttagcac tgccctggtg   1500
attacccaga gatatctatg aaaaccagtg gcttccatca aacctttgcc aactcaggtt   1560
cacagcagct ttgggcagtt atggcagtat ggcattagct gagaggtgtc tgccacttct   1620
gggtcaatgg aataataaat taagtacagg caggaatttg gttgggagca tcttgtatga   1680
tctccgtatg atgtgatatt gatggagata gtggtcctca ttcttggggg ttgccattcc   1740
cacattcccc cttcaacaaa cagtgtaaca ggtccttccc agatttaggg tactttatt    1800
gatggatatg ttttcctttt attcacataa ccccttgaaa ccctgtcttg tcctcctgtt   1860
acttgcttct gctgtacaag atgtagcacc ttttctcctc tttgaacatg gtctagtgac   1920
acggtagcac cagttgcagg aaggagccag acttgttctc agagcactgt gttcacactt   1980
ttcagcaaaa atagctatgg ttgtaacata tgtattccct tcctctgatt tgaaggcaaa   2040
aatctacagt gtttcttcac ttcttttctg atctggggca tgaaaaaagc aagattgaaa   2100
tttgaactat gagtctcctg catggcaaca aaatgtgtgt caccatcagg ccaacaggcc   2160
agcccttgaa tggggattta ttactgttgt atctatgttg catgataaac attcatcacc   2220
ttcctcctgt agtcctgcct cgtactcccc ttccccctatg attgaaaagt aaacaaaacc   2280
cacatttcct atcctggtta gaagaaaatt aatgttctga cagttgtgat cgcctggagt   2340
acttttagac ttttagcatt cgttttttac ctgtttgtgg atgtgtgttt gtatgtgcat   2400
acgtatgaga taggcacatg catcttctgt atggacaaag gtggggtacc tacaggagag   2460
caaaggttaa ttttgtgctt ttagtaaaaa catttaaata caaagttctt tattgggtgg   2520
aattatattt gatgcaaata tttgatcact taaaactttt aaaacttcta ggtaatttgc   2580
cacgcttttt gactgctcac caatacccctg taaaaatacg taattcttcc tgtttgtgta   2640
ataagatatt catatttgta gttgcattaa taatagttat ttcttagtcc atcagatgtt   2700
cccgtgtgcc tcttttatgc caaattgatt gtcatatttc atgttgggac caagtagttt   2760
gcccatggca aacctaaatt tatgacctgc tgaggcctct cagaaaactg agcatactag   2820
caagacagct cttcttgaaa aaaaaaatat gtatacacaa atatatacgt atatctatat   2880
atacgtatgt atatacacac atgtatattc ttccttgatt gtgtagctgt ccaaaataat   2940
```

```
aacatatata gagggagctg tattccttta tacaaatctg atggctcctg cagcactttt    3000
tccttctgaa aatatttaca ttttgctaac ctagtttgtt actttaaaaa tcagttttga    3060
tgaaaggagg gaaaagcaga tggacttgaa aaagatccaa gctcctatta gaaaaggtat    3120
gaaaatcttt atagtaaaat tttttataaa ctaaagttgt accttttaat atgtagtaaa    3180
ctctcattta tttggggttc gctcttggat ctcatccatc cattgtgttc tctttaatgc    3240
tgcctgcctt ttgaggcatt cactgcccta gacaatgcca ccagagatag tgggggaaat    3300
gccagatgaa accaactctt gctctcacta gttgtcagct tctctggata agtgaccaca    3360
gaagcaggag tcctcctgct tgggcatcat tgggccagtt ccttctcttt aaatcagatt    3420
tgtaatggct cccaaattcc atcacatcac atttaaattg cagacagtgt tttgcacatc    3480
atgtatctgt tttgtcccat aatatgcttt ttactccctg atcccagttt ctgctgttga    3540
ctcttccatt cagttttatt tattgtgtgt tctcacagtg acaccatttg tccttttctg    3600
caacaacctt tccagctact tttgccaaat tctatttgtc ttctccttca aaacattctc    3660
ctttgcagtt cctcttcatc tgtgtagctg ctcttttgtc tcttaactta ccattcctat    3720
agtactttat gcatctctgc ttagttctat tagttttttg gccttgctct tctccttgat    3780
tttaaaattc cttctatagc tagagctttt cttttctttca ttctctcttc ctgcagtgtt    3840
ttgcatacat cagaagctag gtacataagt taaatgattg agagttggct gtatttagat    3900
ttatcacttt ttaatagggt gagcttgaga gttttctttc tttctgtttt ttttttttgt    3960
tttttttttt tttttttttt tttttttttt tgactaattt cacatgctct aaaaaccttc    4020
aaaggtgatt attttttctcc tggaaactcc aggtccattc tgtttaaatc cctaagaatg    4080
tcagaattaa aataacaggg ctatcccgta attggaaata tttctttttt caggatgcta    4140
tagtcaattt agtaagtgac caccaaattg ttatttgcac taacaaagct caaaacacga    4200
taagtttact cctccatctc agtaataaaa attaagctgt aatcaacctt ctaggtttct    4260
cttgtcttaa aatgggtatt caaaaatggg gatctgtggt gtatgtatgg aaacacatac    4320
tccttaattt acctgttgtt ggaaactgga gaaatgattg tcgggcaacc gtttattttt    4380
tattgtattt tatttggttg agggattttt ttataaacag ttttacttgt gtcatatttt    4440
aaaattacta actgccatca cctgctgggg tcctttgtta ggtcattttc agtgactaat    4500
agggataatc caggtaactt tgaagagatg agcagtgagt gaccaggcag ttttctgcc     4560 tttagctttg acagttctta attaagatca ttgaagacca gctttctcat aaatttctct    4620
ttttgaaaaa aagaaagcat ttgtactaag ctcctctgta agacaacatc ttaaatctta    4680
aaagtgttgt tatcatgact ggtgagagaa gaaaacattt tgtttttatt aaatggagca    4740
ttatttacaa aaagccattg ttgagaatta gatcccacat cgtataaaata tctattaacc    4800 attctaaata aagagaactc cagtgttgct atgtgcaaga tcctctcttg gagctttttt    4860
gcatagcaat taaggtgtg ctatttgtca gtagccattt ttttgcagtg atttgaagac     4920
caaagttgtt ttacagctgt gttaccgtta aaggttttttt tttttatatg tattaaatca   4980
atttatcact gtttaaagct ttgaatatct gcaatctttg ccaaggtact tttttatttta   5040 aaaaaaaaca taactttgta aatattaccc tgtaatatta tatatactta ataaaacatt    5100
ttaagctatt ttgttgggct atttctattg ctgctacagc agaccacaag cacatttctg    5160
aaaaatttaa tttattaatg tatttttaag ttgcttatat tctaggtaac aatgtaaaga    5220
atgatttaaa atattaatta tgaattttttt gagtataata cccaataagc ttttaattag   5280
```
agcagagttt taattaaaag ttttaaatca gtc 5313

<210> SEQ ID NO 5
<211> LENGTH: 323
<212> TYPE: PRT
<213> ORGANISM: Homo sapiens

<400> SEQUENCE: 5

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu
```

<210> SEQ ID NO 6
<211> LENGTH: 305
<212> TYPE: PRT
<213> ORGANISM: Homo sapiens

<400> SEQUENCE: 6

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
290                 295                 300

Asn
305

<210> SEQ ID NO 7
<211> LENGTH: 312
<212> TYPE: PRT
<213> ORGANISM: Homo sapiens

<400> SEQUENCE: 7

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp

```
            50                  55                  60
Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Glu
305                 310

<210> SEQ ID NO 8
<211> LENGTH: 21
<212> TYPE: DNA
<213> ORGANISM: Artificial Sequence
<220> FEATURE:
<223> OTHER INFORMATION: 18S RNA forward primer

<400> SEQUENCE: 8
ttgacggaag ggcaccacca g                                           21

<210> SEQ ID NO 9
<211> LENGTH: 21
<212> TYPE: DNA
<213> ORGANISM: Artificial Sequence
<220> FEATURE:
<223> OTHER INFORMATION: 18S RNA reverse primer

<400> SEQUENCE: 9
gcaccaccac ccacggaatc g                                           21

<210> SEQ ID NO 10
<211> LENGTH: 20
<212> TYPE: DNA
<213> ORGANISM: Artificial Sequence
```

```
<220> FEATURE:
<223> OTHER INFORMATION: beta-actin forward primer

<400> SEQUENCE: 10
ttccttcttg ggtatggaat                                          20

<210> SEQ ID NO 11
<211> LENGTH: 20
<212> TYPE: DNA
<213> ORGANISM: Artificial Sequence
<220> FEATURE:
<223> OTHER INFORMATION: beta-actin reverse primer

<400> SEQUENCE: 11
gagcaatgat cttgatcctc                                          20

<210> SEQ ID NO 12
<211> LENGTH: 21
<212> TYPE: DNA
<213> ORGANISM: Artificial Sequence
<220> FEATURE:
<223> OTHER INFORMATION: CD47 forward primer

<400> SEQUENCE: 12
aggccaagtc cagaagcatt c                                        21

<210> SEQ ID NO 13
<211> LENGTH: 21
<212> TYPE: DNA
<213> ORGANISM: Artificial Sequence
<220> FEATURE:
<223> OTHER INFORMATION: CD47 reverse primer

<400> SEQUENCE: 13
aatcattctg ctgctcgttg c                                        21

<210> SEQ ID NO 14
<211> LENGTH: 34
<212> TYPE: DNA
<213> ORGANISM: Artificial Sequence
<220> FEATURE:
<223> OTHER INFORMATION: 3' Neo PCR primer

<400> SEQUENCE: 14
gcatcgcatt gtctgagtag gtgtcattct attc                          34

<210> SEQ ID NO 15
<211> LENGTH: 28
<212> TYPE: DNA
<213> ORGANISM: Artificial Sequence
<220> FEATURE:
<223> OTHER INFORMATION: 5' IAP PCR primer

<400> SEQUENCE: 15
tcaccttgtt gttcctgtac tacaagca                                 28

<210> SEQ ID NO 16
<211> LENGTH: 23
<212> TYPE: DNA
<213> ORGANISM: Artificial Sequence
<220> FEATURE:
<223> OTHER INFORMATION: 3' IAP PCR Primer

<400> SEQUENCE: 16
tgtcacttcg caagtgtagt tcc                                      23
```

```
<210> SEQ ID NO 17
<211> LENGTH: 23
<212> TYPE: DNA
<213> ORGANISM: Artificial Sequence
<220> FEATURE:
<223> OTHER INFORMATION: FLT3-ITD PCR Forward Primer 11F

<400> SEQUENCE: 17
gcaatttagg tatgaaagcc agc                                             23

<210> SEQ ID NO 18
<211> LENGTH: 23
<212> TYPE: DNA
<213> ORGANISM: Artificial Sequence
<220> FEATURE:
<223> OTHER INFORMATION: FLT3-ITD PCR Reverse Primer 12R

<400> SEQUENCE: 18
ctttcagcat tttgacggca acc                                             23
```

METHODS FOR MANIPULATING PHAGOCYTOSIS MEDIATED BY CD47

CROSS REFERENCE

This application claims benefit and is a Continuation of application Ser. No. 15/054,891 filed Feb. 26, 2016, which is a Continuation of application Ser. No. 14/800,474 filed Jul. 15, 2015, now U.S. Pat. No. 9,399,682 issued on Jul. 26, 2016, which is a Continuation of application Ser. No. 13/941,276 filed Jul. 12, 2013, now abandon, which is a Continuation of application Ser. No. 12/837,409 filed Jul. 15, 2010 now U.S. Pat. No. 8,562,997 issued on Oct. 22, 2013, which is a Continuation in Part of PCT Application No. PCT/US2009/000319, filed Jan. 15, 2009, which claims benefit of U.S. Provisional Patent Application No. 61/189,786, filed Aug. 22, 2008, which claims benefit of U.S. Provisional Patent Application No. 61/011,324, filed Jan. 15, 2008, which applications are incorporated herein by reference in their entirety.

FEDERALLY SPONSORED RESEARCH AND DEVELOPMENT

This invention was made with Government support under contract CA086017 awarded by the National Institutes of Health. The Government has certain rights in the invention.

BACKGROUND

The reticuloendothelial system (RES) is a part of the immune system. The RES consists of the phagocytic cells located in reticular connective tissue, primarily monocytes and macrophages. The RES consists of 1) circulating monocytes; 2) resident macrophages in the liver, spleen, lymph nodes, thymus, submucosal tissues of the respiratory and alimentary tracts, bone marrow, and connective tissues; and 3) macrophage-like cells including dendritic cells in lymph nodes, Langerhans cells in skin, and microglial cells in the central nervous system. These cells accumulate in lymph nodes and the spleen. The RES functions to clear pathogens, particulate matter in circulation, and aged or damaged hematopoietic cells.

To eliminate foreign cells or particles in the innate immune response, macrophage-mediated phagocytosis is induced when the phosphatidylserine receptor (PSR) reacts to phosphatidylserine (PS), which can be externalized from the membranes of dead cells, such as apoptotic and necrotic cells. In turn, the interaction between PS and PSR plays a crucial role in the clearance of apoptotic cells by macrophages. Once phagocytosis has been performed by macrophages, the inflammatory response is downregulated by an increase in factors such as IL-10, TGF-$\beta$, and prostaglandin E2 (PGE2). The strict balance between the inflammatory and anti-inflammatory responses in both innate and adaptive immunity plays a critical role in maintaining cellular homeostasis and protecting a host from extrinsic invasion.

The causal relationship between inflammation and the neoplastic progression is a concept widely accepted. Data now support the concept of cancer immunosurveillance—that one of the physiologic functions of the immune system is to recognize and destroy transformed cells. However, some tumor cells are capable of evading recognition and destruction by the immune system. Once tumor cells have escaped, the immune system may participate in their growth, for example by promoting the vascularization of tumors.

Both adaptive and innate immune cells participate in the surveillance and the elimination of tumor cells, but monocytes/macrophages may be the first line of defense in tumors, as they colonize rapidly and secrete cytokines that attract and activate dendritic cells (DC) and NK cells, which in turn can initiate the adaptive immune response against transformed cells.

Tumors that escape from the immune machinery can be a consequence of alterations occurring during the immunosurveillance phase. As an example, some tumor cells develop deficiencies in antigen processing and presentation pathways, which facilitate evasion from an adaptive immune response, such as the absence or abnormal functions of components of the IFN-$\gamma$ receptor signaling pathway. Other tumors suppress the induction of proinflammatory danger signals, leading, for example, to impaired DC maturation. Finally, the inhibition of the protective functions of the immune system may also facilitate tumor escape, such as the overproduction of the anti-inflammatory cytokines IL-10 and TGF-$\beta$, which can be produced by many tumor cells themselves but also by macrophages or T regulatory cells.

A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop. Many observations suggest that analogies between normal stem cells and tumorigenic cells are appropriate. Both normal stem cells and tumorigenic cells have extensive proliferative potential and the ability to give rise to new (normal or abnormal) tissues. Both tumors and normal tissues are composed of heterogeneous combinations of cells, with different phenotypic characteristics and different proliferative potentials.

Stem cells are defined as cells that have the ability to perpetuate themselves through self-renewal and to generate mature cells of a particular tissue through differentiation. In most tissues, stem cells are rare. As a result, stem cells must be identified prospectively and purified carefully in order to study their properties. Perhaps the most important and useful property of stem cells is that of self-renewal. Through this property, striking parallels can be found between stem cells and cancer cells: tumors may often originate from the transformation of normal stem cells, similar signaling pathways may regulate self-renewal in stem cells and cancer cells, and cancers may comprise rare cells with indefinite potential for self-renewal that drive tumorigenesis.

Study of cell surface markers specific to or specifically upregulated in cancer cells is pivotal in providing targets for reducing growth of or for depleting cancer cells. Provided herein is a marker for myeloid leukemia, especially a marker for Acute Myeloid Leukemia (AML). Our studies have revealed a role of this marker in helping AML stem cells avoid clearance by phagocytosis. Methods are provided for using this marker to increase phagocytosis of AML stem cells (AML SCs), as well as to improve transplantation of hematopoietic and progenitor stem cells.

Interestingly, certain markers are shown to be shared by leukemia stem cells and hematopoietic stem cells (HSCs). During normal development, HSCs migrate to ectopic niches in fetal and adult life via the blood stream. Once in the blood stream, HSCs must navigate the vascular beds of the spleen and liver before settling in a niche. At these vascular beds, macrophages function to remove damaged cells and foreign particles from the blood stream. Furthermore, during inflammatory states, macrophages become more phagocytically active. The newly arriving stem cells thus face the possibility of being phagocytosed while en route, unless additional protection can be generated. Exploration of mechanisms by which the endogenous HSC avoid being cleared by phagocytosis can provide insight into ways for improving transplantation success of hematopoietic and progenitor stem cells. The present invention satisfies these, and other, needs.

SUMMARY OF THE INVENTION

Methods are provided to manipulate phagocytosis of hematopoietic cells, including circulating hematopoietic cells, e.g. bone marrow cells. In some embodiments of the invention the circulating cells are hematopoietic stem cells, or hematopoietic progenitor cells, particularly in a transplantation context, where protection from phagocytosis is desirable. In other embodiments the circulating cells are leukemia cells, particularly acute leukemia cells such as AML (acute myeloid leukemia) or ALL (acute lymphocytic leukemia), where increased phagocytosis is desirable. In certain embodiments of the invention, methods are provided to manipulate macrophage phagocytosis of circulating hematopoietic cells. In yet other embodiments of the invention, methods are provided to manipulate phagocytosis of solid tumors.

In other embodiments, tumor cells, e.g. solid tumor cells, leukemia cells, etc. are targeted for phagocytosis by blocking CD47 on the cell surface. It is shown that leukemia cells, particularly AML, ALL, etc. cells, evade macrophage surveillance by upregulation of CD47 expression. Administration of agents that mask the CD47 protein, e.g. antibodies that bind to CD47 and prevent interaction between CD47 and SIRPα are administered to a patient, which increases the clearance of acute leukemia cells via phagocytosis. In other embodiments, cells of solid tumors, e.g. carcinoma cells, are targeted for phagocytosis by blocking CD47 present on the cell surface. In other aspects, an agent that masks CD47 is combined with monoclonal antibodies directed against one or more additional leukemia stem cell (LSC) markers, e.g. CD96, and the like, which compositions can be synergistic in enhancing phagocytosis and elimination of LSC as compared to the use of single agents.

In another embodiment, methods are provided for targeting or depleting leukemia stem cells, the method comprising contacting a population of cells, e.g. blood from a leukemia patient, with a reagent that specifically binds CD47 in order to target or deplete LSC. In certain aspects, the reagent is an antibody conjugated to a cytotoxic agent, e.g. radioactive isotope, chemotherapeutic agent, toxin, etc. In some embodiments, the depletion is performed on an ex vivo population of cells, e.g. the purging of autologous stem cell products (mobilized peripheral blood or bone marrow) for use in autologous transplantation for patients with acute myeloid leukemia. In another embodiment, methods are provided for targeting cancer cells of a solid tumor in a human subject by administering an antibody against CD47 to the subject.

In some embodiments of the invention, hematopoietic stem or progenitor cells are protected from phagocytosis in circulation by providing a host animal with a CD47 mimetic molecule, which interacts with SIRPα on phagocytic cells, such as, macrophages, and decreases phagocytosis. The CD47 mimetic may be soluble CD47; CD47 coated on the surface of the cells to be protected, a CD47 mimetic that binds to SIRPα at the CD47 binding site, and the like. In some embodiments of the invention, CD47 is provided as a fusion protein, for example soluble CD47 fused to an Fc fragment, e.g., IgG1 Fc, IgG2 Fc, Ig A Fc etc.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 3A-3B. FIG. 3A Progenitor Profiles of Normal Bone Marrow (left), post-polycythemic myelofibrosis with myeloid metaplasia (PPMM) and CML Blast Crisis. FIG. 3B FACS analysis of human normal bone marrow (red) versus UMPD (green) versus PV (blue=ML) versus atypical CML (orange), HSC, progenitor and lineage positive cell CD47 expression.

(FIG. 5A) Progenitor Profiles of Normal bone marrow (left) versus AML (right). (FIG. 5B) FACS analysis of human normal bone marrow (red) versus AML (blue) HSC, progenitor and lineage positive cell (blast) CD47 expression.

FIG. 6A-6B. CD47 is More Highly Expressed on AML LSC Compared to Their Normal Counterparts. FIG. 6A. Relative CD47 expression on normal bone marrow HSC (Lin−CD34+CD38−CD90+) and MPP (Lin−CD34+CD38−CD90−CD45RA−), as well as LSC (Lin−CD34+CD38−CD90−) and bulk leukemia cells from human AML samples was determined by flow cytometry. Mean fluorescence intensity was normalized for cell size and against lineage positive cells to account for analysis on different days. The same sample of normal bone marrow (red, n=3) or AML (blue, n=13) is indicated by the same symbol in the different populations. The differences between the mean expression of HSC with LSC (p=0.003), HSC with bulk leukemia (p=0.001), MPP with LSC (p=0.004), and MPP with bulk leukemia (p=0.002) were statistically significant using a 2-sided Student's t-test. The difference between the mean expression of AML LSC compared to bulk AML was not statistically significant with p=0.50 using a paired 2-sided Student's t-test. FIG. 6B. Clinical and molecular characteristics of primary human AML samples manipulated in vitro and/or in vivo.

(FIG. 7C)

The phagocytic index was determined for each condition by calculating the number of ingested cells per 100 macrophages.

Figure 8A:
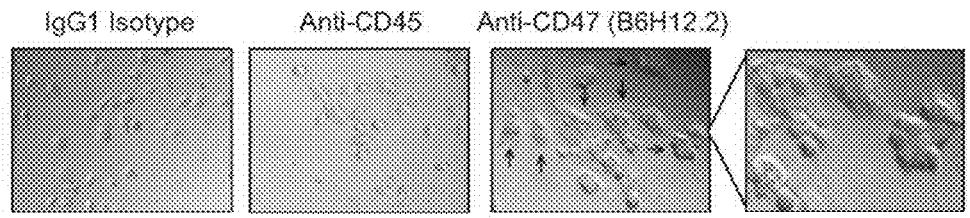
Figure 8B:
Figure 8C:
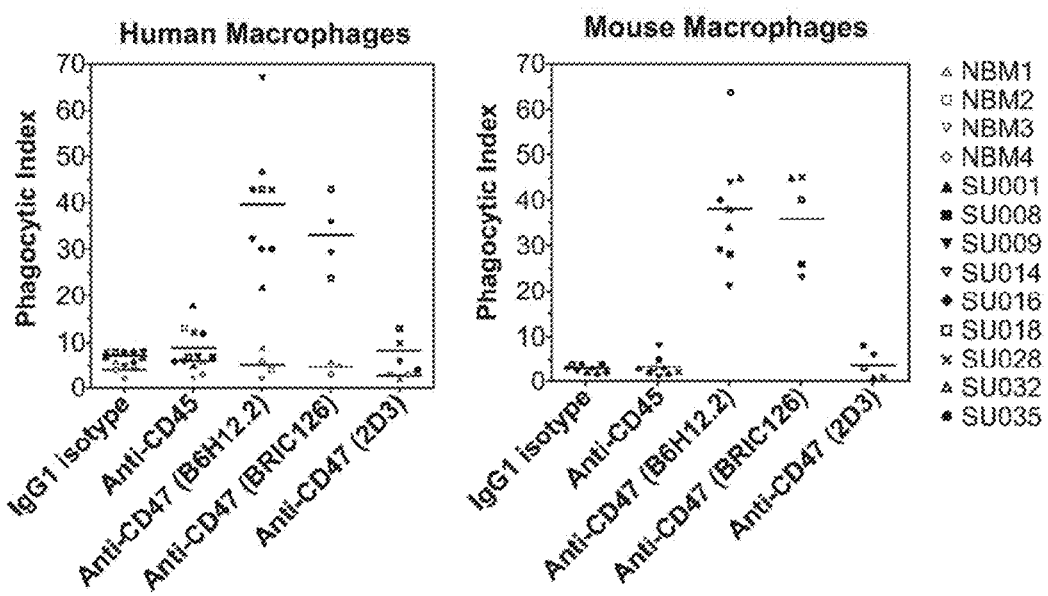

FIG. 8A-8C. Monoclonal Antibodies Directed Against Human CD47 Preferentially Enable Phagocytosis of Human AML LSC by Human and Mouse Macrophages. FIG. 8A,8B. CFSE-labeled AML LSC were incubated with human peripheral blood-derived macrophages (FIG. 8A) or mouse bone marrow-derived macrophages (FIG. 8B) in the presence of IgG1 isotype control, anti-CD45 IgG1, or anti-CD47 (B6H12.2) IgG1 antibody. These cells were assessed by immunofluorescence microscopy for the presence of fluorescently labeled LSC within the macrophages (indicated by arrows). (FIG. 8C) CFSE-labeled AML LSC or normal bone marrow CD34+ cells were incubated with human (left) or mouse (right) macrophages in the presence of the indicated antibodies and then assessed for phagocytosis by immunofluorescence microscopy. The phagocytic index was determined for each condition by calculating the number of ingested cells per 100 macrophages. For AML LSC, the differences between isotype or anti-CD45 antibody with blocking anti-CD47 antibody treatment (B6H12.2 and BRIC126) were statistically significant with $p<0.001$ for all pairwise comparisons with human and mouse macrophages. For human macrophages, the differences between AML LSC and normal CD34$^+$ cells were statistically significant for B6H12.2 ($p<0.001$) and BRIC126 ($p=0.002$).

Figure 9A:
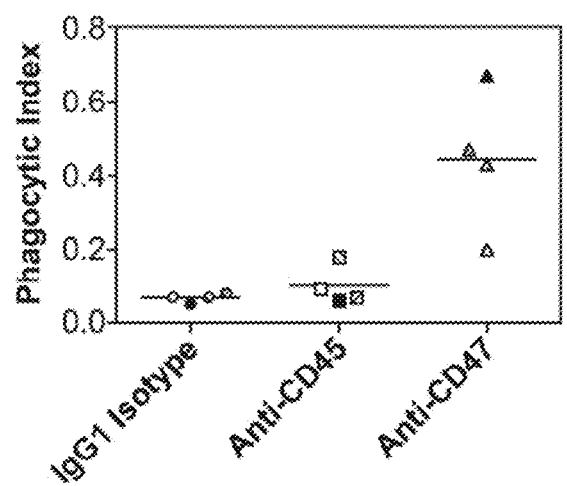
Figure 9B:
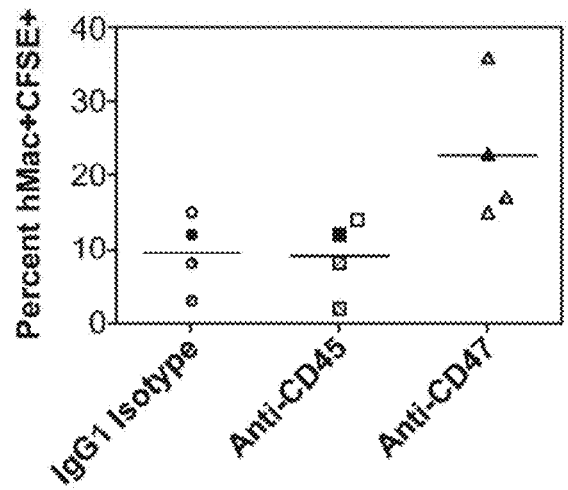

FIG. 9A-9B. Anti-CD47 Antibody stimulates in vitro macrophage phagocytosis of primary human AML LSC. AML LSC were purified by FACS from four primary human AML samples, labeled with the fluorescent dye CFSE, and incubated with human peripheral blood macrophages either in the presence of an isotype control, isotype matched anti-CD45, or anti-CD47 antibody. (FIG. 9A) These cells were assessed by immunofluorescence microscopy for the presence of fluorescently-labeled LSC within the macrophages. The phagocytic index was determined for each condition by calculating the number of ingested cells per 100 macrophages. (FIG. 9B) The macrophages were harvested, stained with a fluorescently labeled anti-human macrophage antibody, and analyzed by flow cytometry. hMac+CFSE+ double positive events identify macrophages that have phagocytosed CFSE-labeled LSC. Each sample is represented by a different color.

Figure 10A:
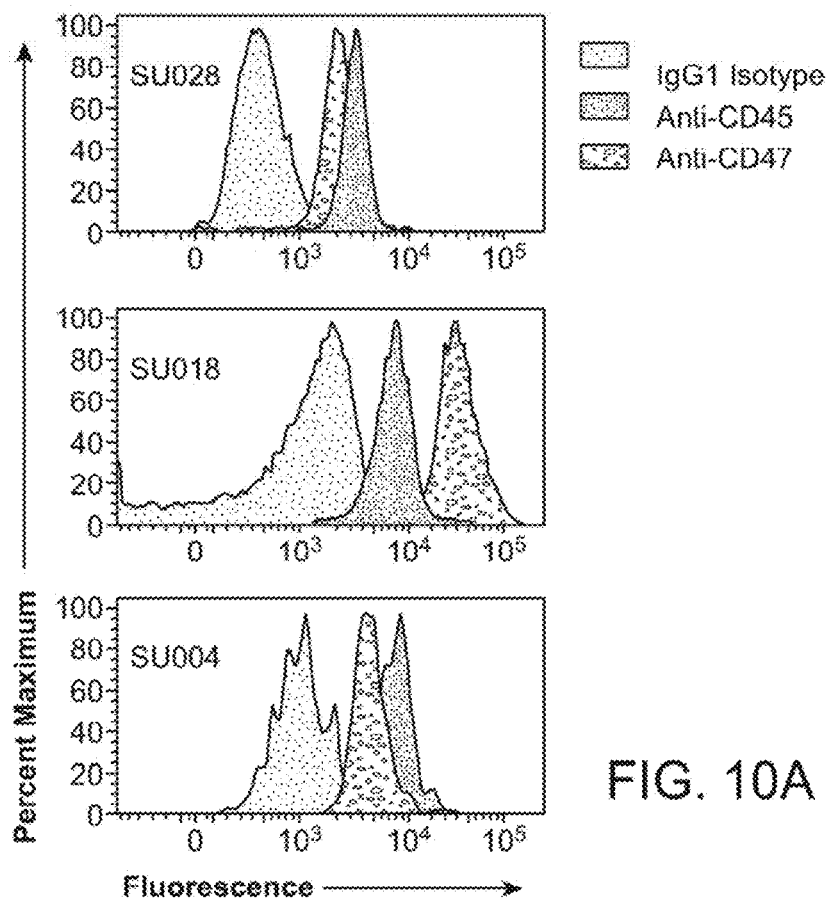
Figure 10B:
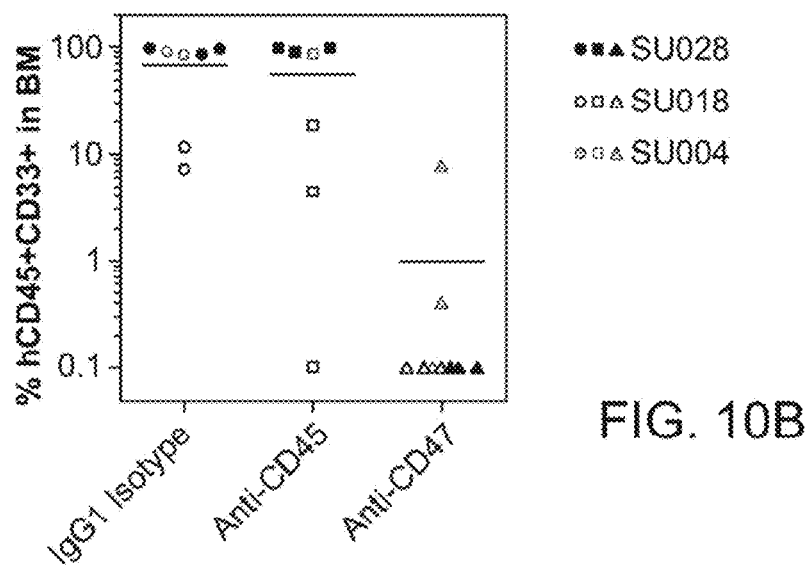

FIG. 10A-10B. A Monoclonal Antibody Directed Against Human CD47 Inhibits AML LSC Engraftment In Vivo. Three primary human AML samples were incubated with IgG1 isotype control, anti-CD45 IgG1, or anti-CD47 IgG1 antibody (B6H12.2) prior to transplantation into newborn NOG mice. A portion of the cells was analyzed for coating by staining with a secondary anti-mouse IgG antibody and analyzed by flow cytometry (FIG. 10A). 13 weeks later, mice were sacrificed and the bone marrow was analyzed for the percentage of human CD45+CD33+ myeloid leukemia cells by flow cytometry (FIG. 10B). The difference in mean engraftment between anti-CD47-coated cells and both isotype ($p<0.001$) and anti-CD45 ($p=0.003$) coated cells was statistically significant.

FIG. 11A-11F. CD47 is upregulated in murine acute myeloid leukemia. Typical stem and progenitor plots are shown for leukemic hMRP8bcrablxhMRP8bcl2 cells compared to control non-leukemic animals. Lin−c-Kit+Sca-1+ gated cells from control bone marrow (FIG. 11A) and leukemic spleen (FIG. 11B) and Lin−c-Kit+Sca-1− gated cells from control bone marrow (FIG. 11C) and leukemic spleen (FIG. 11D) demonstrate perturberances in normal hematopoiesis in leukemic mice. Frequency is shown as a percentage of entire marrow or spleen mononuclear fraction. (FIG. 11E) Quantitative RT-PCR shows that CD47 is upregulated in leukemic BM cells. Data are shown from 3 sets of mice transplanted with either leukemic or control hRMP8bcrablxhMRP8bcl2 BM cells and then sacrificed 2-6 weeks later. Results were normalized to beta-actin and 18S rRNA expression. Fold change relative to control transplanted whole Bcl-2+ BM cells was determined. Error bars represent 1 s.d. (FIG. 11F) Histograms show expression of CD47 on gated populations for leukemic (gray) and control (black) mice.

Figure 12A:
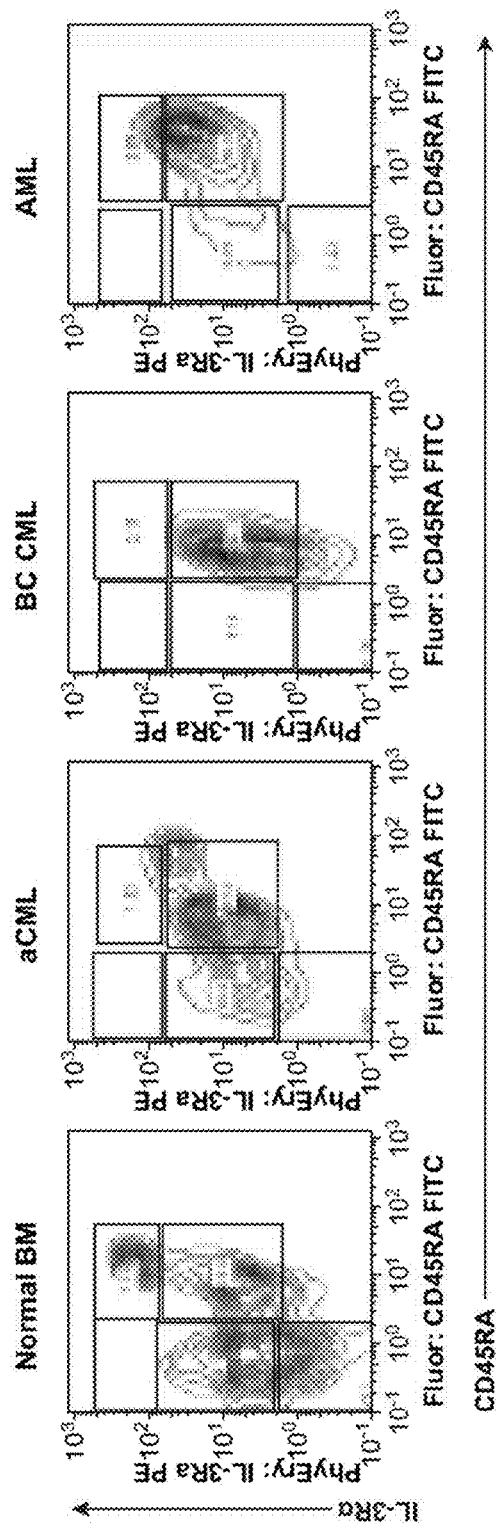
Figure 12B:
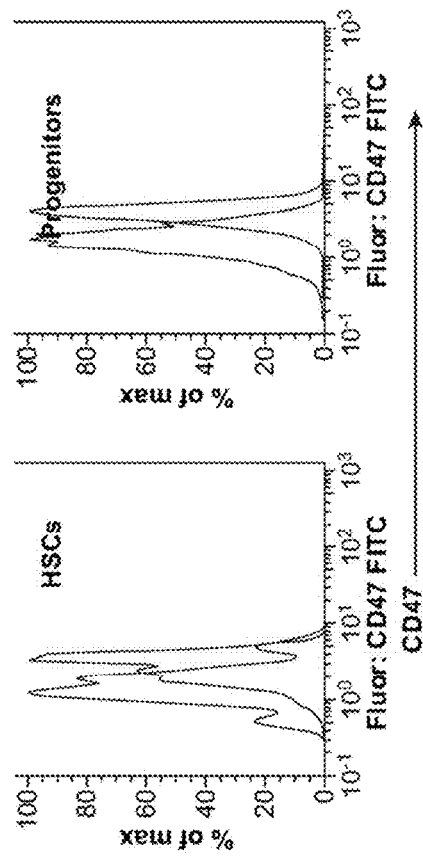

FIG. 12A-12C. GMP expansion and CD47 upregulation in human myeloid leukemia. (FIG. 12A) Representative FACS plots of myeloid progenitors (CD34+CD38+Lin−) including common myeloid progenitors (CMP), megakaryocyte-erythroid progenitors (MEP) and granulocyte-macrophage progenitors (GMP) in normal bone marrow (BM) versus aCML, BC CML and AML. (FIG. 12B) Comparative FACS histograms of CD47 expression by normal (red; n=6) and acute myelogenous leukemic (AML, blue; n=6) hematopoietic stem cells (HSC; CD34+CD38−CD90+Lin−) and progenitors (CD34+CD38+Lin−). (FIG. 12C) Comparative FACS histograms of CD47 expression by normal (red) and chronic myelogenous leukemia hematopoietic stem cells (HSC; CD34+CD38−CD90+Lin) and committed progenitors (CD34+CD38+Lin−). Upper panel: Normal (n=7) versus chronic phase CML (n=4) HSC, progenitors and lineage positive cells. Middle panel: Normal (n=7) versus accelerated phase CML (n=7) HSC, progenitors and lineage positive cells. Lower panel: Normal (n=7) versus blast crisis CML (n=4) HSC, progenitors and lineage positive cells.

FIG. 13A-13G. Over-expression of murine CD47 increases tumorigenicity of MOLM-13 cells. (FIG. 13A) MOLM-13 cells were transduced with either control virus or virus expressing murine CD47 cDNA form 2. The resulting cell lines, termed Tet or Tet-CD47, were transplanted competitively into RAG/common gamma chain deficient mice with untransduced MOLM-13 cells ($5\times10^5$ Tet (n=6) or Tet-47 (n=8) cells with $5\times10^5$ MOLM-13). Mice were analyzed for GFP and human CD45 chimerism when moribund. (FIG. 13B) MOLM-13 chimerism in hematopoietic tissues was determined by human CD45 chimerism and measurement of tumor lesion size. (FIG. 13C) Survival of mice competitively transplanted with MOLM-13 plus Tet or Tet-CD47 MOLM-13 cells was plotted. Control mice died of large tumor burden at the site of injection but had no engraftment in hematopoietic tissues. (FIG. 13D) Hematoxylin and eosin sections of Tet-CD47 MOLM-13 transplanted liver (200×). Periportal (arrow) and sinusoidal (arrowhead) tumor infiltration is evident. (FIG. 13E) $1\times10^6$Tet (n=5) or Tet-CD47 MOLM-13 (n=4) cells were injected into the right femur of RAG2−/−, Gc−/− mice and the tissues were analyzed 50-75 days later and chimerism of MOLM-13 cells in bone marrow was determined. (FIG. 13F) Survival curve of mice transplanted intrafemorally with Tet or Tet-CD47 MOLM-13 cells. (FIG. 13G) Examples of liver tumor formation and hepatomegaly in Tet-CD47 MOLM-13 transplanted mice versus control transplanted mice. GFP fluorescence demonstrates tumor nodule formation as well diffuse infiltration.

FIG. 14A-14D. CD47 over-expression prevents phagocytosis of live unopsonized MOLM-13 cells. (FIG. 14A) Tet or Tet-CD47 MOLM-13 cells were incubated with bone marrow derived macrophages (BMDM) for 2, 4, or 6 hours and phagocytic index was determined. Error bars represent 1 s.d. (n=6 for each time point). (FIG. 14B) FACS analysis of BMDMs incubated with either Tet or Tet-CD47 cells. (FIG.

14C) Photomicrographs of BMDMs incubated with Tet or Tet-CD47 MOLM-13 cells at 2 and 24 hours (400×). (FIG. 14D) Tet or Tet-CD47 MOLM-13 cells were transplanted into RAG2−/−, Gc−/− mice and marrow, spleen, and liver macrophages were analyzed 2 hours later. GFP+ fraction of macrophages are gated. Results are representative of 3 experiments.

FIG. 15A-15I. Higher expression of CD47 on MOLM-13 cells correlates with tumorigenic potential and evasion of phagocytosis. (FIG. 15A) Tet-CD47 MOLM-13 cells were divided into high and low expressing clones as described. Histograms show CD47 expression in MOLM-13 high (black), MOLM-13 low (gray), and mouse bone marrow (shaded) cells. Value obtained for $MFI/FSC^2$ ($\times 10^9$) are shown. (FIG. 15B) Mice transplanted with CD47hi MOLM-13 cells were given doxycycline for 2 weeks. The histograms show level of CD47 expression in untreated (shaded) and treated (shaded) mice, with the values of $MFI/FSC^2$ ($\times 10^9$) indicated. (FIG. 15C) Survival of RAG2−/−, Gc−/− mice transplanted with $1\times10^6$ $CD47^{hi}$, $CD47^{lo}$ MOLM-13 cells, or $CD47^{hi}$ MOLM-13 cells with doxycycline administration after 2 weeks post-transplant. (FIG. 15D) Liver and spleen size of mice at necropsy or 75 days after transplant with $1\times10^6$ $CD47^{hi}$, $CD47^{lo}$ MOLM-13 cells, or $CD47^{hi}$ MOLM-13 cells with doxycycline administration after 2 weeks post-transplant. (FIG. 15E) Bone marrow and spleen chimerism of human cells in mice at necropsy or 75 days after transplant with $1\times10^6$ $CD47^{hi}$, $CD47^{lo}$ MOLM-13 cells, or $CD47^{loi}$ MOLM-13 cells with doxycycline administration after 2 weeks post-transplant. (FIG. 15F) Murine CD47 expression on $CD47^{lo}$ MOLM-13 cells engrafting in bone marrow (open) compared with original cell line (shaded). The values of $MFI/FSC^2$ ($\times 10^9$) are indicated. (FIG. 15G) $2.5\times10^5$ $CD47^{hi}$ or $CD47^{lo}$ MOLM-13 cells were incubated with $5\times10^4$ BMDMs for 2 hours. Phagocytic index is shown. (FIG. 15H) $2.5\times10^5$ $CD47^{hi}$ RFP and $CD47^{lo}$ MOLM-13 GFP cells were incubated with $5\times10^4$ BMDMs for 2 hours. Phagocytic index is shown for three separate samples for $CD47^{hi}$ RFP (red) and $CD47^{lo}$ MOLM-13 GFP (green) cells. (FIG. 15I) $2.5\times10^5$ $CD47^{hi}$ RFP and $CD47^{lo}$ MOLM-13 GFP cells were incubated with $5\times10^4$ BMDMs for 24 hours. Photomicrographs show brightfield (top left), RFP (top right), GFP (bottom left), and merged (bottom right) images.

Figure 16A:
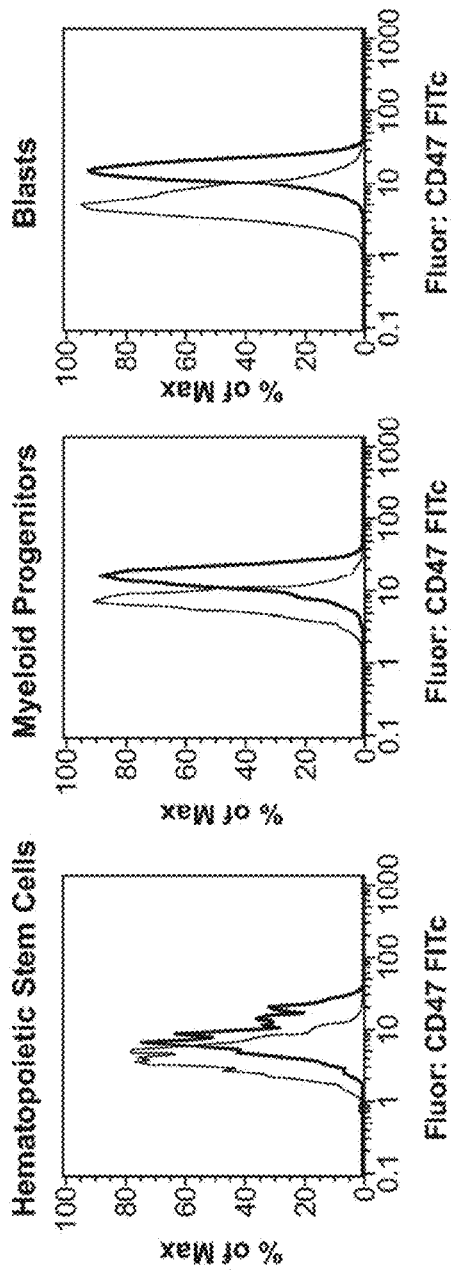
Figure 16B:
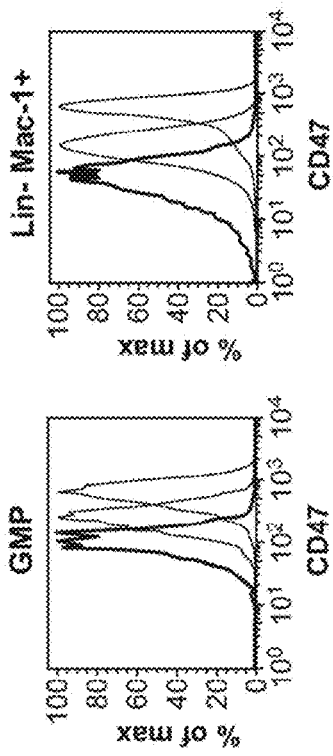
Figure 16C:
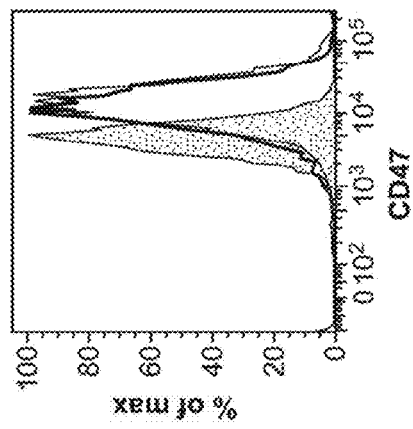
Figure 17A:
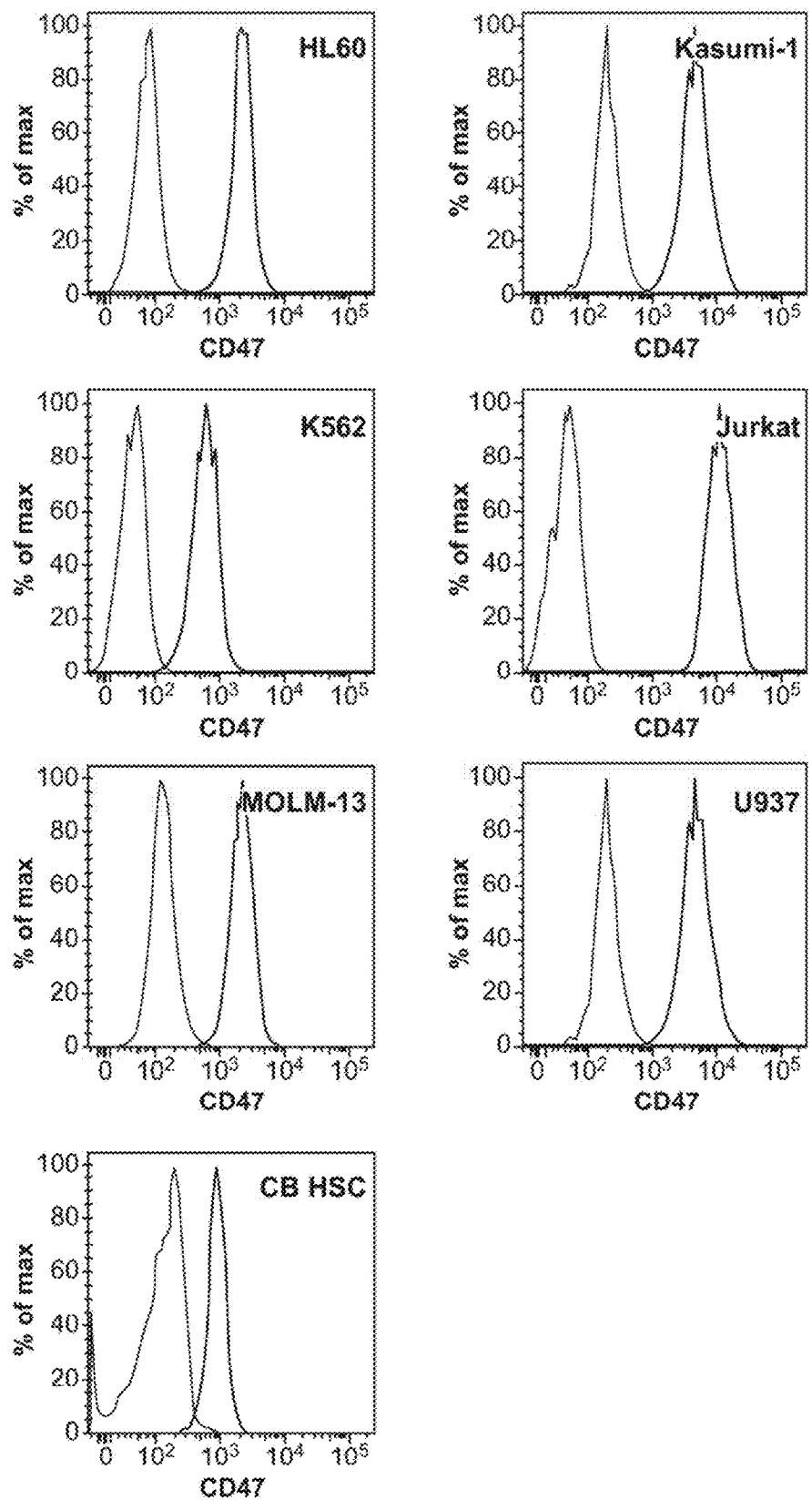
Figure 17B:
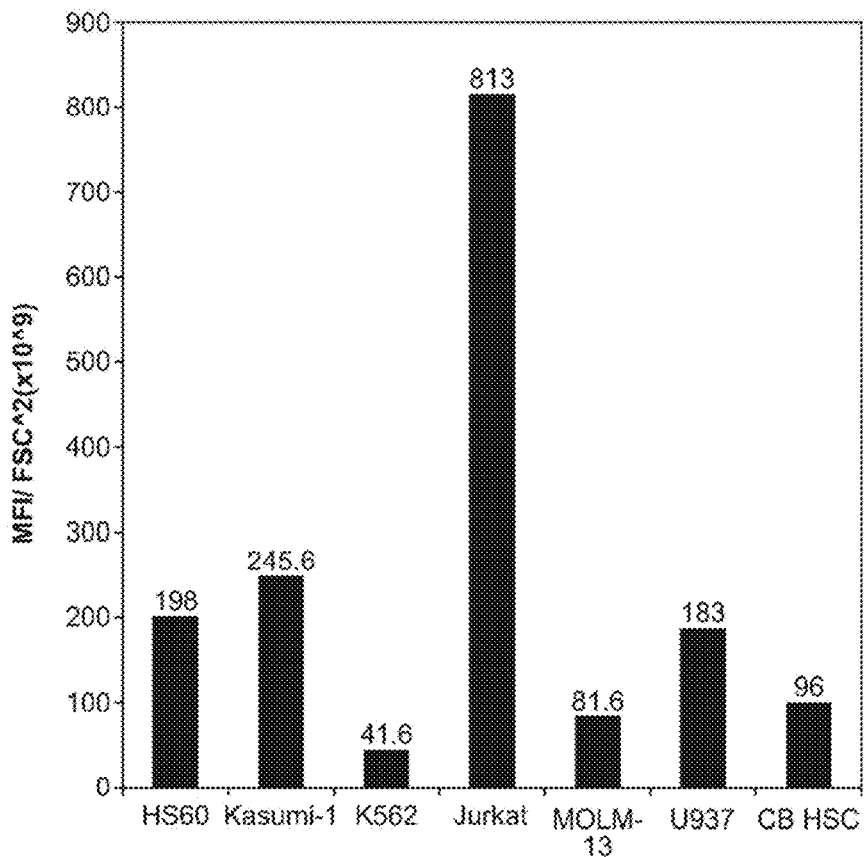
Figure 17C:
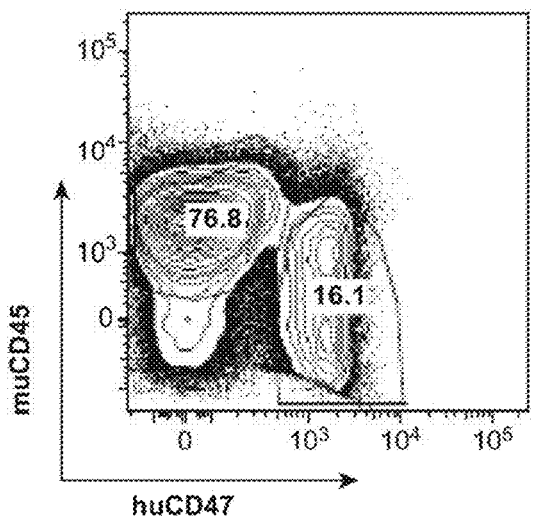
Figure 17D:
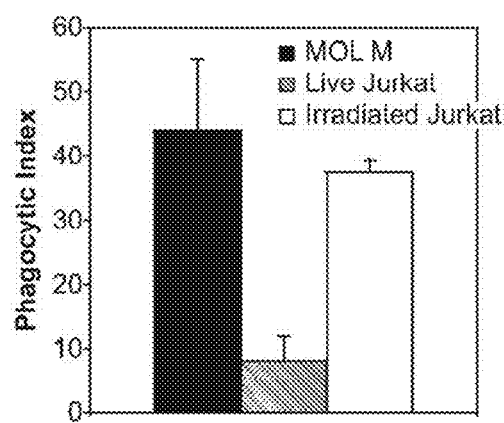

FIG. 16A-16C. (FIG. 16A) FACS analysis of CD47 expression of non-leukemic Fas lpr/lpr hMRP8bcl-2 (blue) and leukemic Fas lpr/lpr hMRP8bcl-2 (green) bone marrow hematopoietic stem cells (c-kit+Sca+Lin−), myeloid progenitors (c-kit+Sca-Lin−) or blasts (c-kit lo Sca-Lin−). (FIG. 16B) Mouse bone marrow was transduced with retrovirus containing p210 bcr/abl as previously described[24]. Mice were sacrificed when moribund and the spleens were analyzed. Expression of CD47 in c-Kit+Mac-1+ cells in the spleens of two leukemic mice (unshaded histograms) and bone marrow from a wild-type mouse (shaded histogram) are shown. (FIG. 16C) Histograms show expression of CD47 on gated populations for leukemic hMRP8bcrabl× hMRP8bcl2 mice (red), hMRP8bcl2 non-leukemic (blue) and wild-type (green) mice. CD47 was stained using FITC conjugated anti-mouse CD47 (Pharmingen).

FIG. 17A-17D. (FIG. 17A) Expression of human CD47 (black histograms) on human leukemia cell lines and cord blood HSCs is shown. Isotype control staining is shown in gray. (FIG. 17B) CD47 MFI over background was normalized to cell size by dividing by $FSC^2$. The value obtained for each cell type is shown above the bar. (FIG. 17C) HL-60 cells engraft mouse bone marrow. $5\times10^5$ cells were injected intravenously into RAG2−/−, Gc−/− animals and mice were analyzed 4 weeks later. (FIG. 17D) Cells were stained with CFSE and co-cultured with BMDM. Phagocytic events were counted after 2 h. For irradiation, Jurkat cells were given a dose of 2 Gray and incubated for 16 h prior to the phagocytosis assay.

FIG. 18A-18G. (FIG. 18A) Analysis of stem and progenitor cells from bone marrow of IAP+/+, IAP+/−, and IAP−/− mice. Stem cells (left) are gated on lineage−c-Kit+Sca-1+ cells. Myeloid progenitors (right) are gated on lineage−c-Kit+Sca-1+ cells. Frequency in whole bone marrow is shown adjacent to each gated population. (FIG. 18B) Colony output on day 7 of individually sorted LT-HSC. G-granulocyte, M-macrophage, GM-granulocyte and macrophage, GEMM-granulocyte, macrophage, erythroid, and megakaryocyte, Meg-megakaryocyte. (FIG. 18C) Survival curve of recipient mice given a radiation dose of 9.5 Gray and transplanted with the cells shown. Radiation control mice all died within 12-15 days. n=5 for each group. (FIG. 18D) Examples of CD45.1/CD45.2 chimerism plots at 4 weeks post-transplant. CD45.1 mice were transplanted with 50 LT-HSC (CD45.2) and $2\times10^5$ CD45.1 helper marrow. Cells are gated on B220−CD3−Mac-1+ side scatter mid/hi cells. IAP−/− cells fail to engraft. (FIG. 18E) Summary of chimerism analysis of mice transplanted with either 50 or 500 IAP+/+ or IAP−/− cells. (FIG. 18F) IAP+/+ or IAP−/− c-Kit enriched cells were incubated with wild-type BMDM. Results indicate mean phagocytic index calculated from three separate samples. Error bars represent 1 s.d. (FIG. 18G) Photomicrographs of phagocytosis assays taken after 2 hours. Genotype of the -Kit enriched cells is shown.

FIG. 19A-19E. (FIG. 19A) Mice were mobilized with Cy/G and bone marrow was analyzed on day 2. Expression level of CD47 on c-Kit+ cells is shown. (FIG. 19B) Myeloid progenitor and stem cell gates are shown for day 2 mobilized bone marrow. Histograms on left show level of CD47 expression in marrow LT-HSC and GMP for steady-state (shaded histogram), day 2 mobilized (black line), and day 5 mobilized (gray line). (FIG. 19C) Relative MFI of CD47 for GMP on days 0-5 of Cy/G mobilization. Results were normalized so that steady state GMP were equal to 100. (FIG. 19D) Myeloid progenitor and stem cell gates are shown for day 2 bone marrow post-LPS treatment. Histograms show level of CD47 expression on day 2 post-LPS (black line), day 5 post-LPS (dark gray shaded histogram), steady state (light gray shaded histogram), and IAP−/− (black shaded histogram) LT-HSC and GMP. (FIG. 19E) Evaluation of KLS cells in the hematopoietic organs of IAP+/+ and IAP−/− mice mobilized on days 2 through 5. Two mice are analyzed per genotype per day.

Figure 20A:
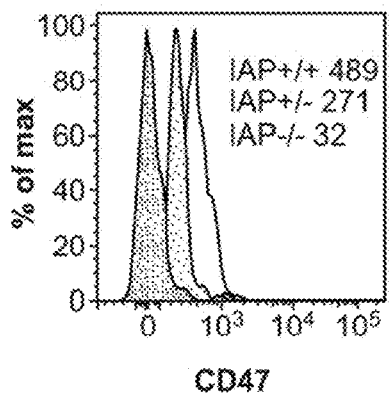
Figure 20B:
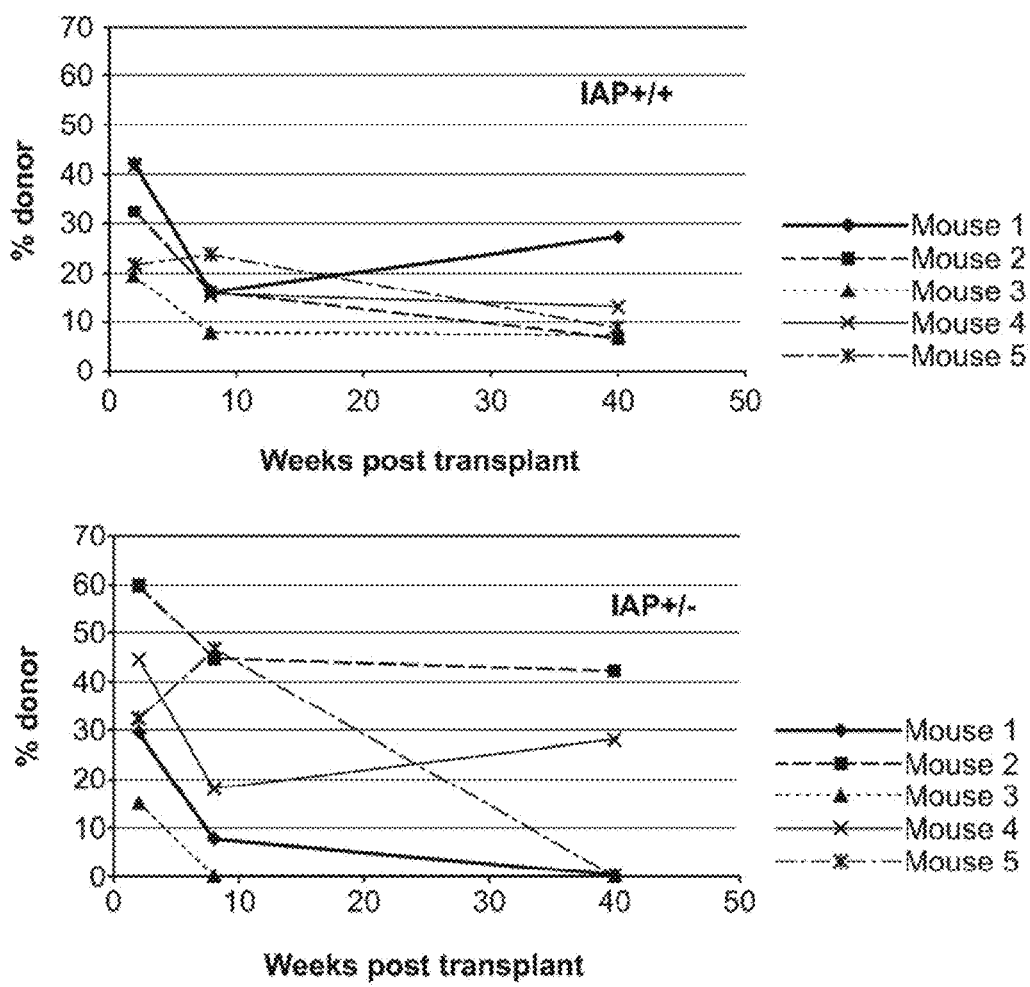

FIG. 20A-20B. (FIG. 20A) CD47 expression level of IAP+/+, IAP+/−, and IAP−/− LT-HSC. The numbers shown are the MFI for each group. (FIG. 20B) Donor chimerism analysis for transplants of IAP+/+ (top) or IAP+/− (bottom) mice. Mice were bled at 2, 8, and 40 weeks post transplant. $2\times10^6$ donor cells were transplanted into sub-lethally irradiated congenic recipients.

Figure 21A:
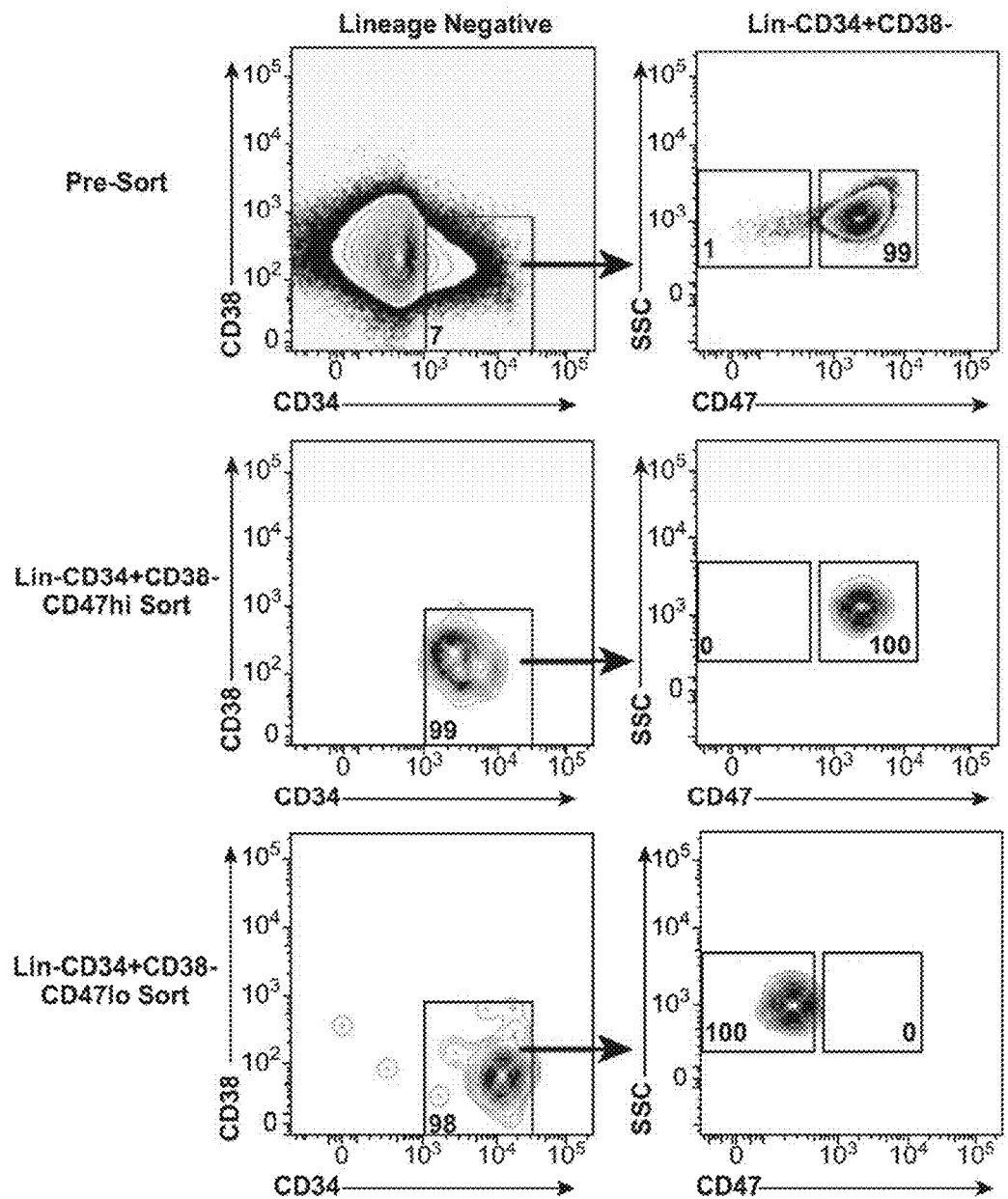
Figure 21B:
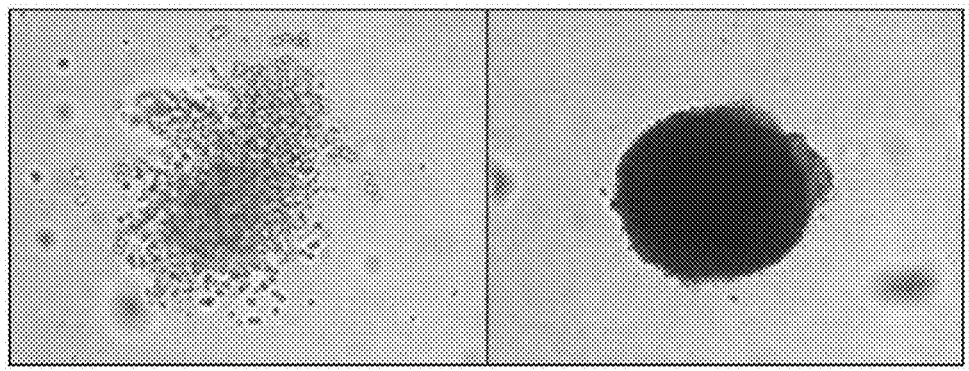
Figure 21C:
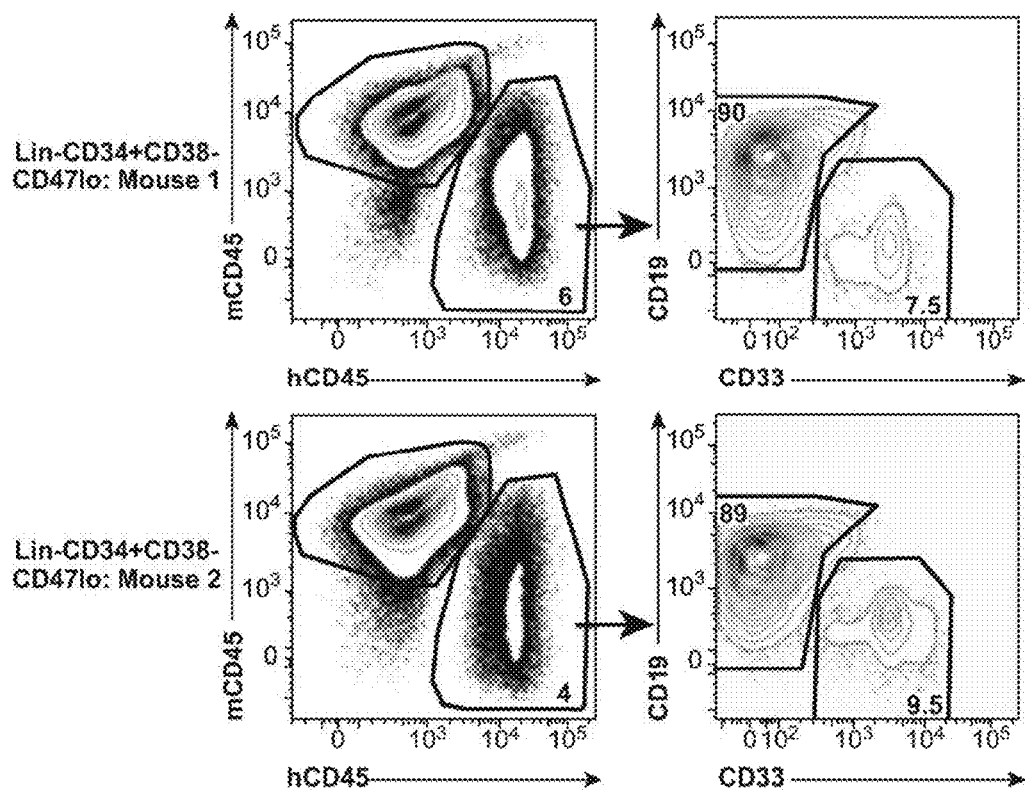
Figure 21D:
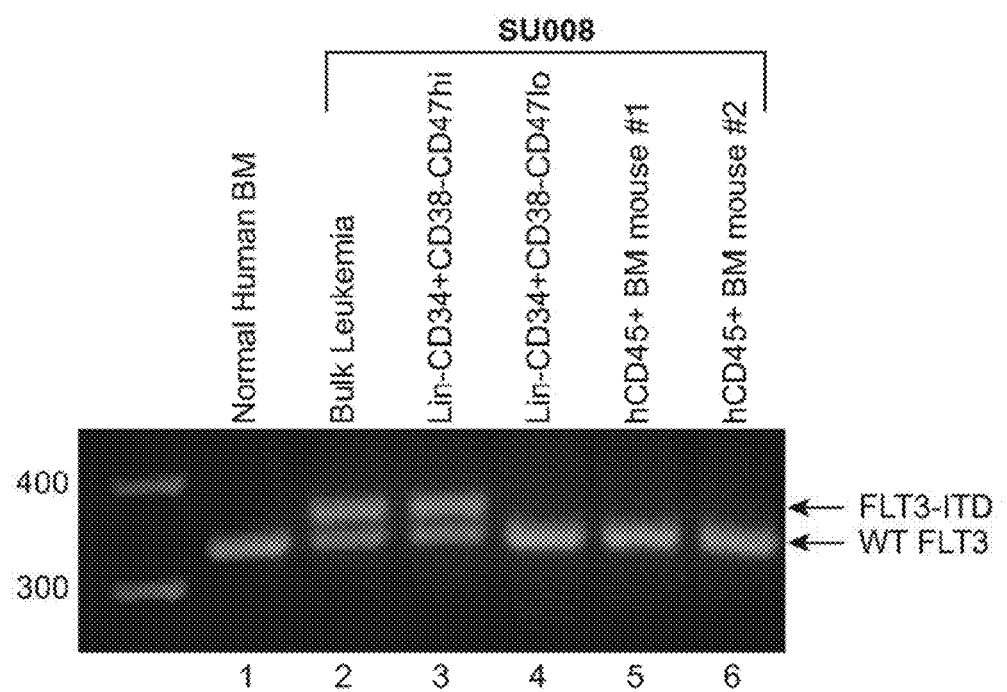

FIG. 21A-21D. Identification and Separation of Normal and Leukemic Progenitors From the Same Patient Based On Differential CD47 Expression. FIG. 21A CD47 expression on the Lin−CD34+CD38− LSC-enriched fraction of specimen SU008 was determined by flow cytometry. CD47hi- and CD47lo-expressing cells were identified and purified using FACS. The left panels are gated on lineage negative cells, while the right panels are gated on Lin−CD34+CD38− cells. FIG. 21B Lin−CD34+CD38−CD47lo and Lin−CD34+ CD38−CD47hi cells were plated into complete methylcellulose, capable of supporting the growth of all myeloid colonies. 14 days later, myeloid colony formation was determined by morphologic assessment. Representative CFU-G/M (left) and BFU-E (right) are presented. FIG. 21C Lin−CD34+CD38−CD47lo cells were transplanted into 2 newborn NOG mice. 12 weeks later, the mice were sacrificed and the bone marrow was analyzed for the presence of human CD45+CD33+ myeloid cells and human CD45+CD19+ lymphoid cells by flow cytometry. FIG. 21D Normal bone marrow HSC, bulk SU008 leukemia cells, Lin−CD34+CD38−CD47hi cells, Lin−CD34+CD38−CD47lo cells, or human CD45+ cells purified from the bone marrow of mice engrafted with Lin−CD34+CD38−CD47lo cells were assessed for the presence of the FLT3-ITD mutation by PCR. The wild type FLT3 and the FLT3-ITD products are indicated.

Figure 22A:
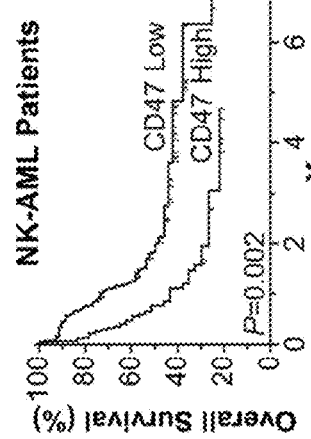
Figure 22B:
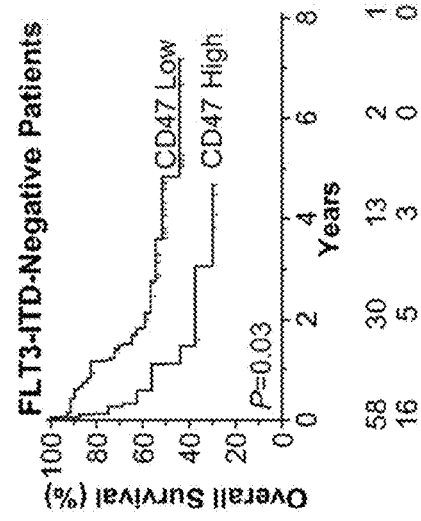
Figure 22C:
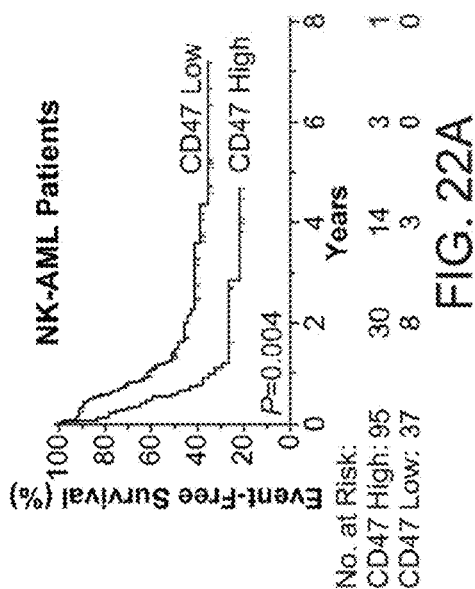
Figure 22D:
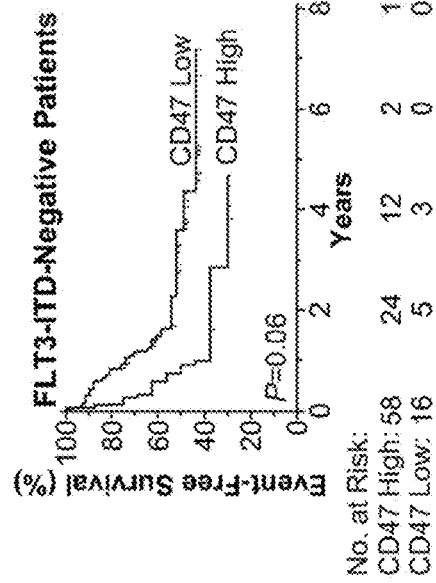

FIG. 22A-22D. Increased CD47 Expression in Human AML is Associated with Poor Clinical Outcomes. Event-free (FIG. 22A, FIG. 22C) and overall (FIG. 22B, FIG. 22D) survival of 132 AML patients with normal cytogenetics (FIG. 22A, FIG. 22B) and the subset of 74 patients without the FLT3-ITD mutation (FIG. 22C, FIG. 22D). Patients were stratified into low CD47 and high CD47 expression groups based on an optimal threshold (28% high, 72% low) determined by microarray analysis from an independent training data set. The significance measures are based on log-likelihood estimates of the p-value, when treating the model with CD47 expression as a binary classification.

Figure 23A:
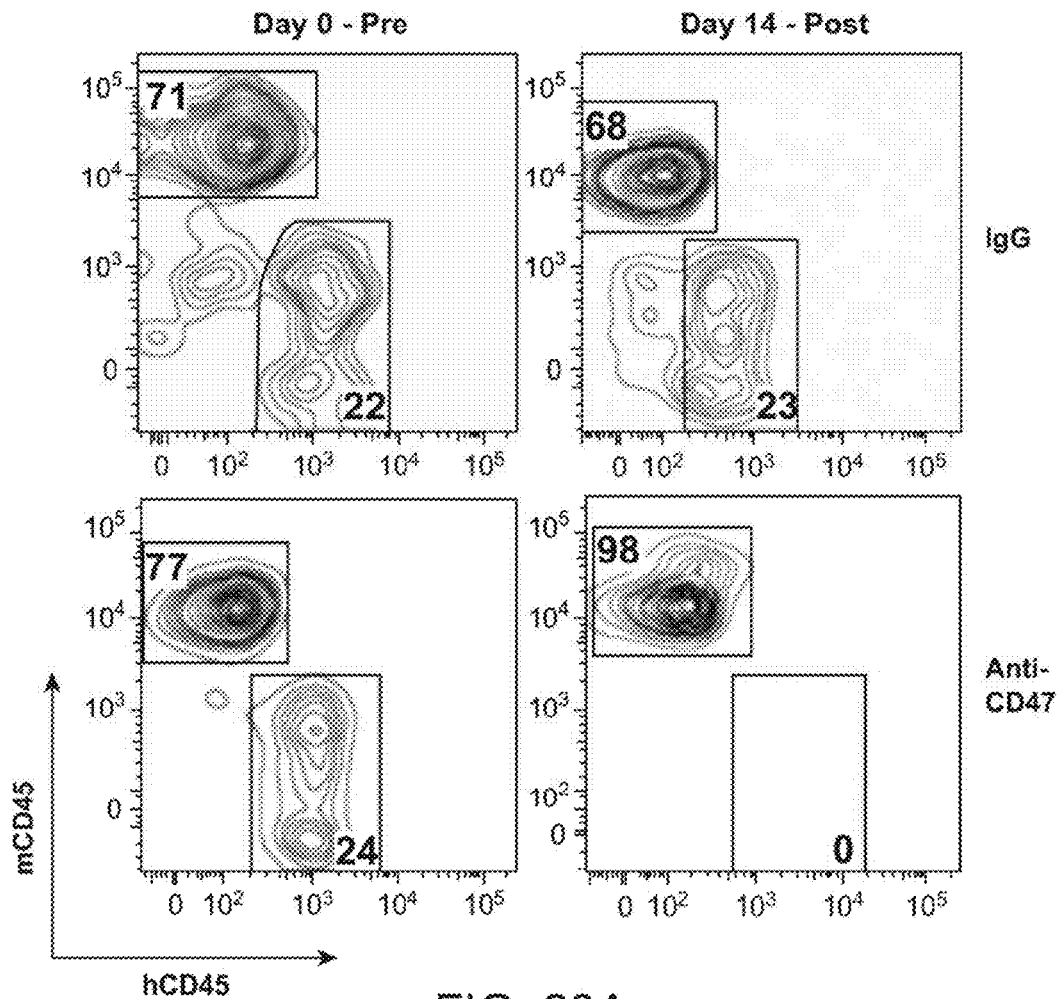
Figure 23B:
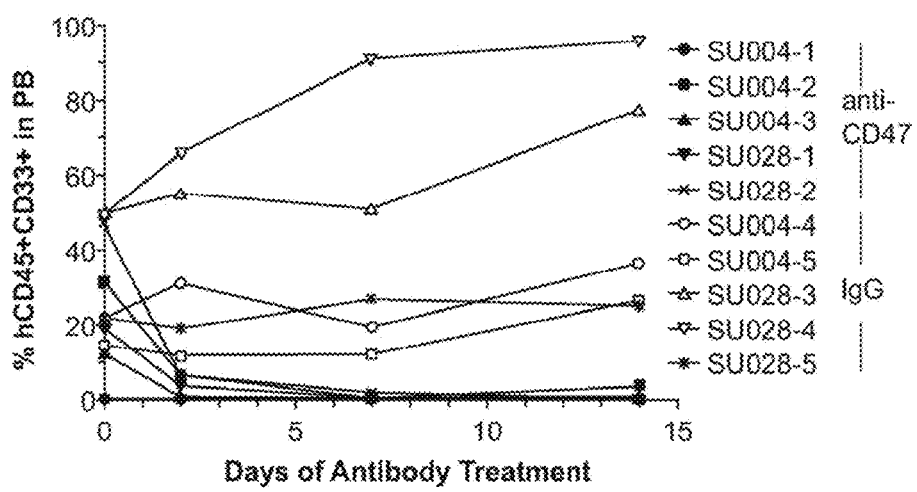
Figure 23C:
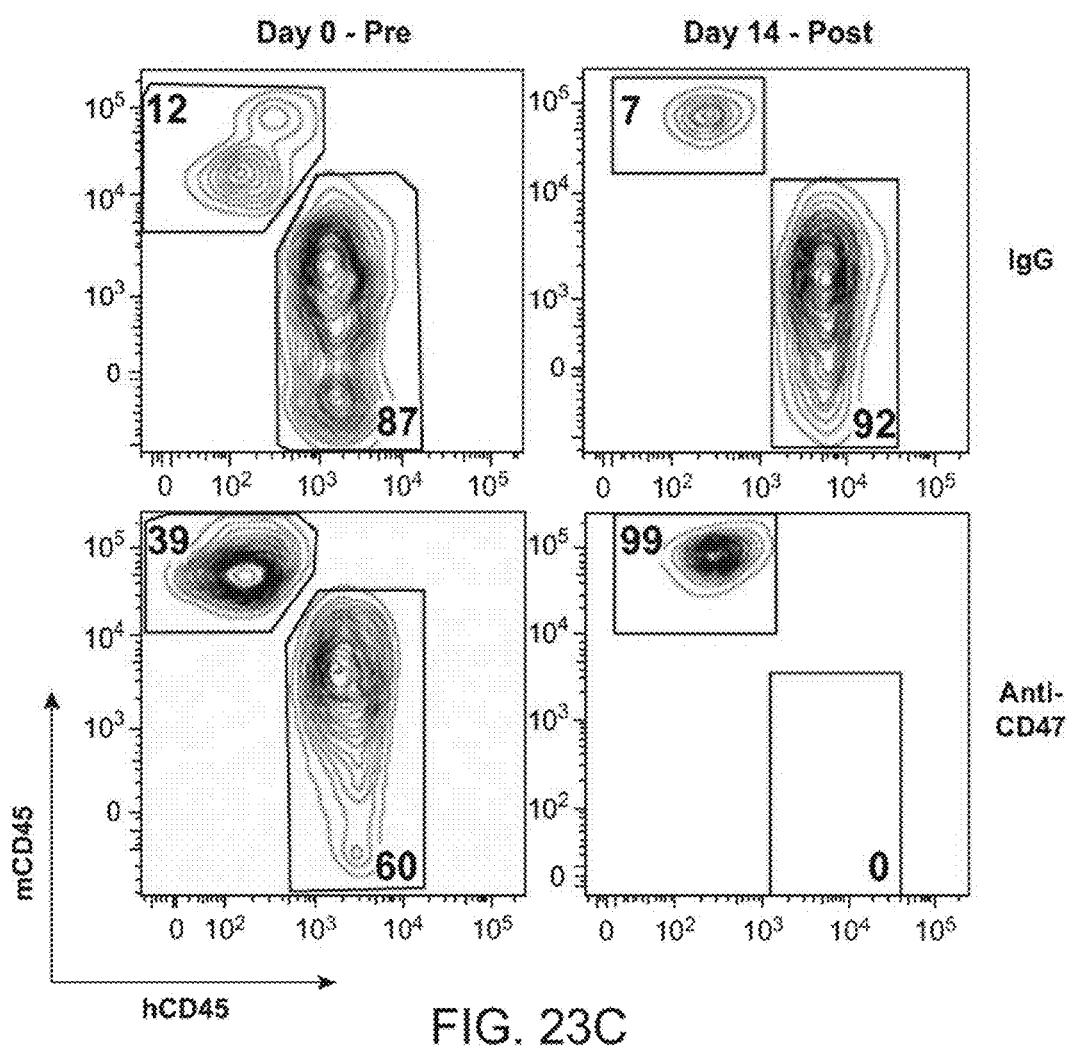
Figure 23D:
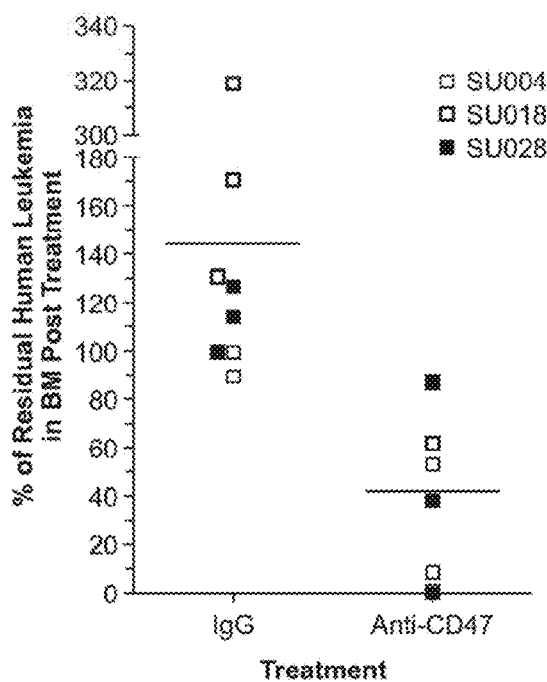
Figure 23E:
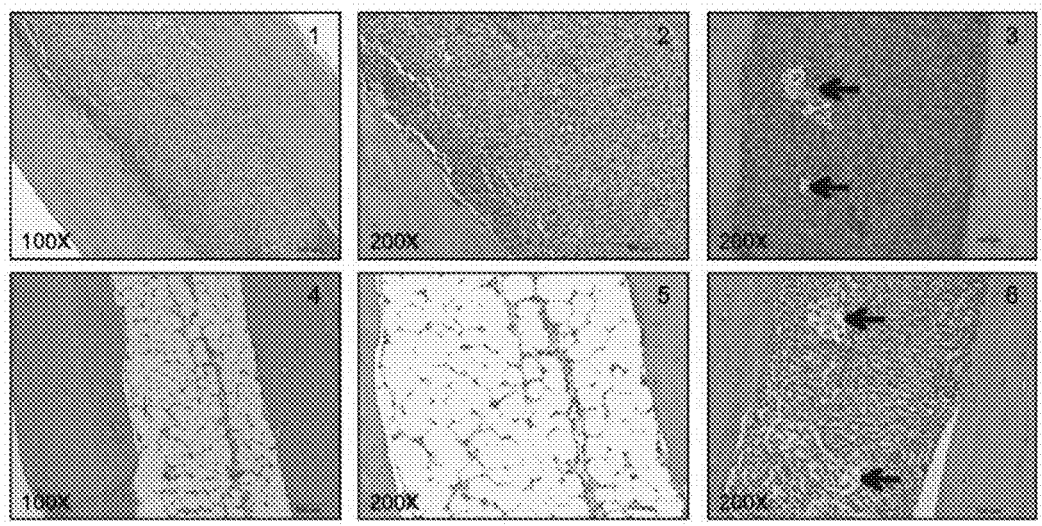

FIG. 23A-23E. A Monoclonal Antibody Directed Against Human CD47 Eliminates AML In Vivo. Newborn NOG mice were transplanted with AML LSC, and 8-12 weeks later, peripheral blood (FIG. 23A, FIG. 23B) and bone marrow (FIG. 23C-23E) were analyzed for baseline engraftment prior to treatment with anti-CD47 (B6H12.2) or control IgG antibody (Day 0). Mice were treated with daily 100 microgram intraperitoneal injections for 14 days, at the end of which, they were sacrificed and peripheral blood and bone marrow were analyzed for the percentage of human CD45+CD33+ leukemia. FIG. 23A Pre- and post-treatment human leukemic chimerism in the peripheral blood from representative anti-CD47 antibody and control IgG-treated mice as determined by flow cytometry. FIG. 23B Summary of human leukemic chimerism in the peripheral blood assessed on multiple days during the course of treatment demonstrated elimination of leukemia in anti-CD47 antibody treated mice compared to control IgG treatment (p=0.007). FIG. 23C Pre- and post-treatment human leukemic chimerism in the bone marrow from representative anti-CD47 antibody or control IgG-treated mice as determined by flow cytometry. FIG. 23D Summary of human leukemic chimerism in the bone marrow on day 14 relative to day 0 demonstrated a dramatic reduction in leukemic burden in anti-CD47 antibody treated mice compared to control IgG treatment (p<0.001). FIG. 23E H&E sections of representative mouse bone marrow cavities from mice engrafted with SU004 post-treatment with either control IgG (panels 1,2) or anti-CD47 antibody (panels 4,5). IgG-treated marrows were packed with monomorphic leukemic blasts, while anti-CD47-treated marrows were hypocellular, demonstrating elimination of the human leukemia. In some anti-CD47 antibody-treated mice that contained residual leukemia, macrophages were detected containing phagocytosed pyknotic cells, capturing the elimination of human leukemia (panels 3,6 arrows).

Figure 24B:
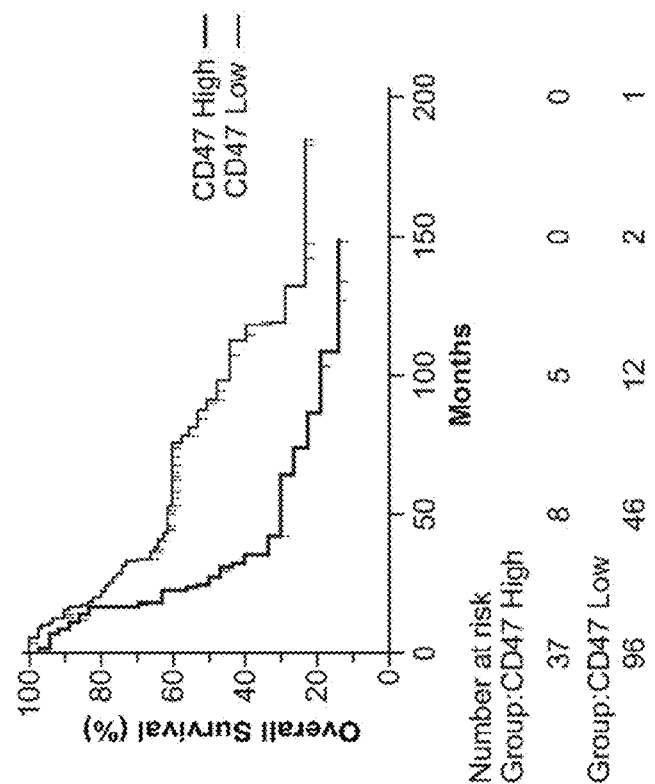
Figure 24A:
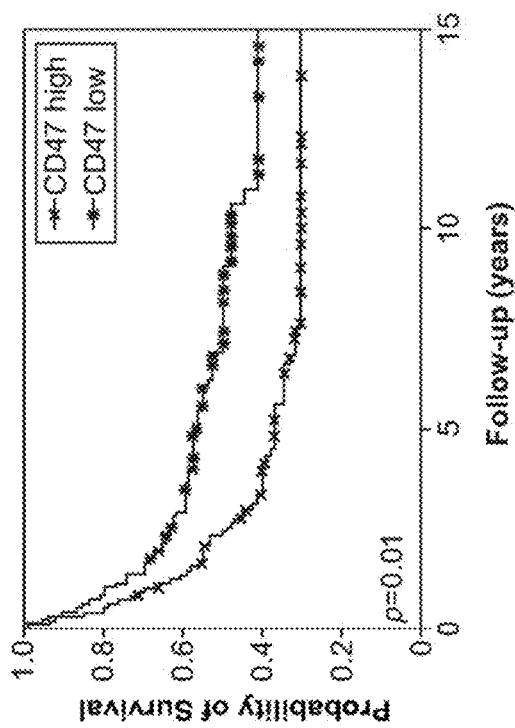

FIG. 24A-24B. Increased CD47 expression predicts worse overall survival in DLBCL and ovarian cancer. (FIG. 24A) A cohort of 230 patients with diffuse large B-cell lymphoma (p=0.01). (FIG. 24B) A cohort of 133 patients with advanced stage (III/IV) ovarian carcinoma (p=0.04).

Figure 25:
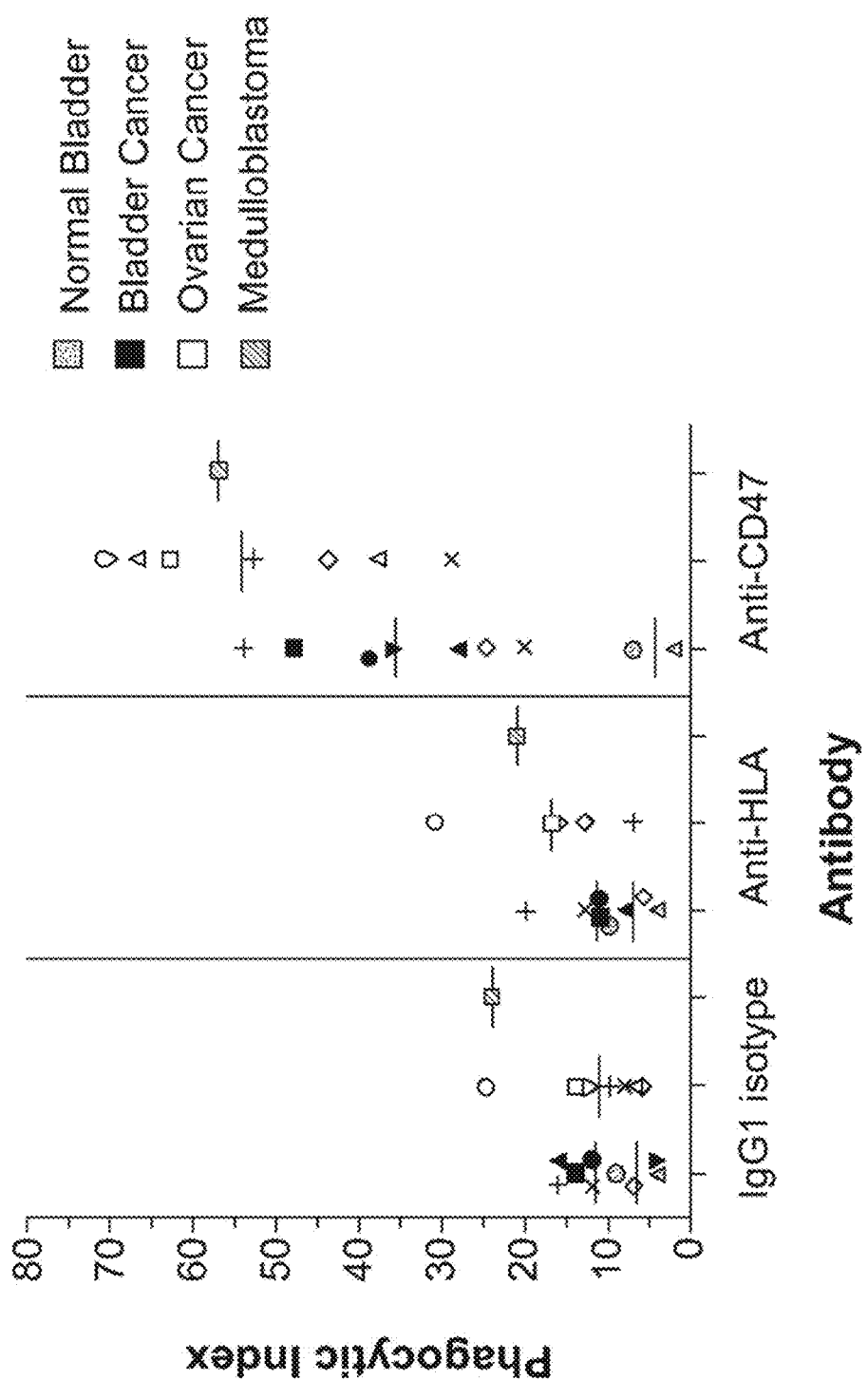

FIG. 25. Anti-CD47 antibody enables the phagocytosis of solid tumor stem cells in vitro. The indicated cells were incubated with human macrophages in the presence of IgG1 isotype, anti-HLA, or anti-CD47 antibodies and the phagocytic index was determined by immunofluorescence microscopy. Statistics: Bladder cancer cells IgG1 isotype compared to anti-HLA (p=0.93) and anti-CD47 (p=0.01); normal bladder urothelium IgG1 isotype compared to anti-HLA (p=0.50) and anti-CD47 (p=0.13); ovarian cancer cells IgG1 isotype compared to anti-HLA (p=0.11) and anti-CD47 (p<0.001). Each individual data point represents a distinct tumor or normal tissue sample.

FIG. 26A-26D. CD47 expression is an independent prognostic predictor in mixed and high-risk ALL. (FIG. 26A) Pediatric ALL patients (n=360) with mixed risk and treatment were stratified into CD47 high- and low-expressing groups based on an optimal cut point. Disease-free survival (DFS) was determined by Kaplan-Meier analysis. CD47 high-expressing patients had a worse DFS compared to CD47 low-expressing patients when CD47 expression was considered as a continuous variable. (FIG. 26B) Pediatric ALL patients (n=207) with high-risk (as defined by age>10 years, presenting WBC count>50,000/μl, hypodiploidy, and BCR-ABL positive disease) and uniform treatment were stratified into CD47 high- and low-expressing groups using a similar approach as in A. CD47 high-expressing patients had a worse overall survival compared to CD47 low-expressing patients (p=0.0009). (FIG. 26C) Multivariate analysis of prognostic covariates was performed from patients analyzed for CD47 expression in (FIG. 26B). When incorporated into this multivariate analysis, CD47 expression still remained prognostic (p=0.035). (FIG. 26D) ALL patients from were stratified into groups either achieving a complete remission (CR) or not achieving a CR (no CR). CD47 expression was higher in patients failing to receive a CR compared to those who did (p=0.0056).

Figure 27A:
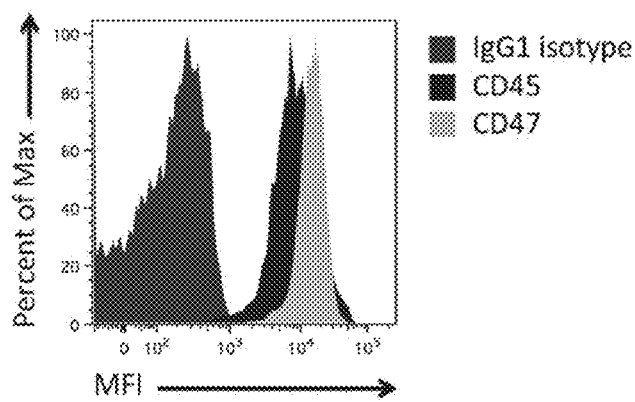
Figure 27B:
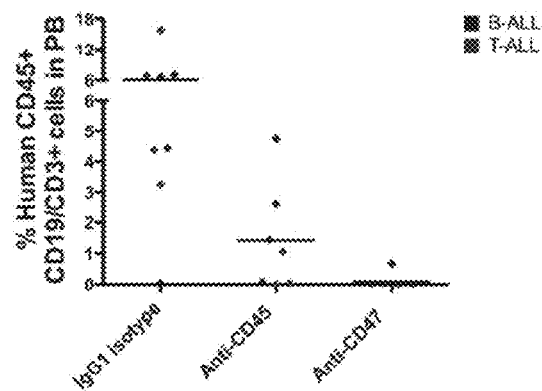
Figure 27C:
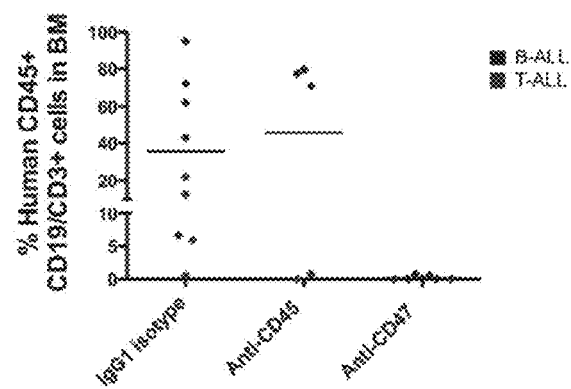

FIG. 27A-27C. Ex vivo coating of ALL cells with an anti-CD47 antibody inhibits leukemic engraftment. (FIG. 27A) ALL cells were incubated with the indicated antibodies in vitro, and positive cell coating was detected by staining a portion of the cells with a fluorescently-labeled secondary antibody. A flow cytometry plot of a representative ALL sample is shown. (FIG. 27B-27C) Pre-coated ALL cells were then transplanted into NSG mice, and human ALL chimerism was assessed 6-10 weeks later in the peripheral blood (FIG. 27B) or bone marrow (FIG. 27C). Ex vivo coating of ALL cells (ALL4 and ALL8) with anti-CD47 antibody inhibited engraftment in the peripheral blood compared to IgG1 isotype control (p=0.02). Ex vivo coating of ALL cells with anti-CD47 antibody inhibited bone marrow engraftment compared to IgG1 isotype control (p=0.02), while no difference in engraftment levels were detected between anti-CD45 antibody and IgG1 isotype control (p=0.67, considering both B and T-ALL samples). Each symbol represents a different primary ALL sample, with each point representing a different mouse. p-values were calculated using the Fisher's exact test. Red diamond=ALL4, blue diamond=ALL4.

FIG. 28A-28D. Anti-CD47 antibody eliminates ALL engraftment in the peripheral blood and bone marrow. (FIG. 28A) NSG mice engrafted with primary B and T-ALL patient samples were treated for 14 days with daily intraperitoneal injections of 100 μg IgG control or anti-CD47 antibody. Peripheral blood human ALL chimerism (huCD45+CD19/CD3+) pre- and post-treatment were measured by flow cytometry. Peripheral blood chimerism is shown from representative treatment mice. (FIG. 28B) Anti-CD47 antibody treatment reduced the level of circulating leukemia compared to IgG control (p=0.0002). (FIG. 28C) Anti-CD47 antibody treatment also reduced ALL engraftment in the bone marrow compared to IgG control (p=0.0004). Each symbol represents a different patient sample, with each data point representing a different mouse. (FIG. 28D) (Top) Hematoxylin and eosin bone marrow sections from representative mice engrafted with B-ALL post-treatment. IgG-treated marrows were primarily packed with monomorphic leukemic blasts, while anti-CD47 antibody-treated marrows demonstrated areas of normal mouse hematopoiesis. (Bottom) Leukemic infiltration was confirmed by immunohistochemical analysis of human CD45 demonstrating robust human leukemia infiltration in IgG-treated bone marrow compared to anti-CD47 antibody-treated marrow.

Figure 29A:
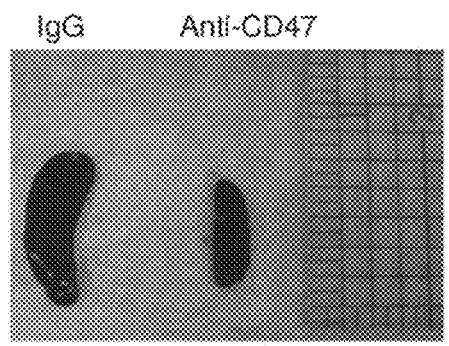
Figure 29B:
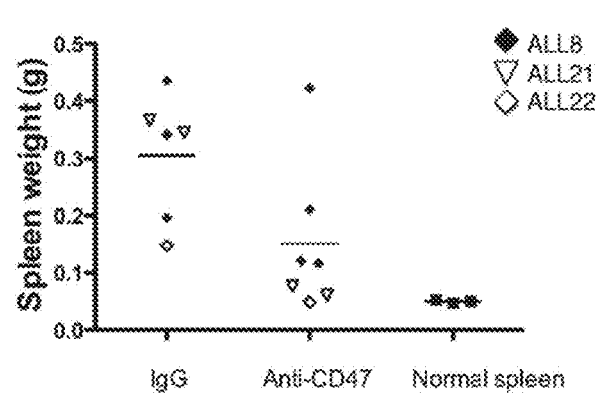
Figure 29C:
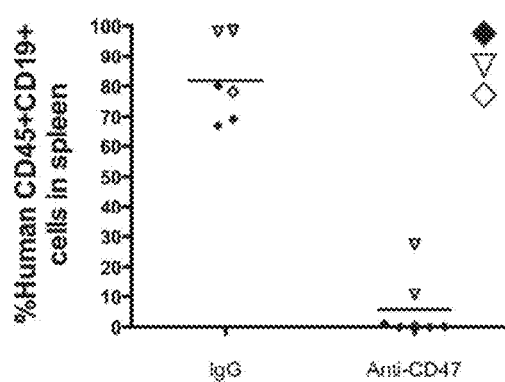
Figure 29D:
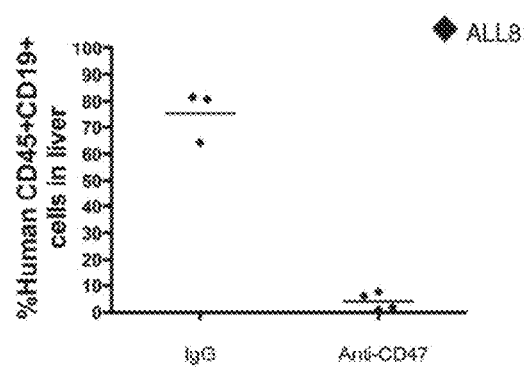

FIG. 29A-29D. Anti-CD47 antibody eliminates ALL engraftment in the spleen and liver. (FIG. 29A) NSG mice engrafted with primary B-ALL cells from sample ALL8, ALL21, or ALL22 were treated for 14 days with daily injections of IgG control or anti-CD47 antibody. Spleens were then harvested, with representative spleens from IgG control or anti-CD47 antibody treatment shown. (FIG. 29B) Spleen weights were determined from mice treated with anti-CD47 antibody demonstrating a reduction in spleen size compared to control IgG-treated mice (p=0.04) to sizes similar to that of normal spleens (p=0.09). Control IgG-treated mice demonstrate splenomegaly compared to normal mice (p=0.0002, student t-test). (FIG. 29C-29D) Levels of ALL engraftment were determined at the end of antibody treatment in the spleen (FIG. 29C) and liver (FIG. 29D). Compared to IgG control, treatment with anti-CD47 antibody eliminated ALL disease in the spleen (p<0.0001) and liver (p<0.0001, student t-test).

Figure 30A:
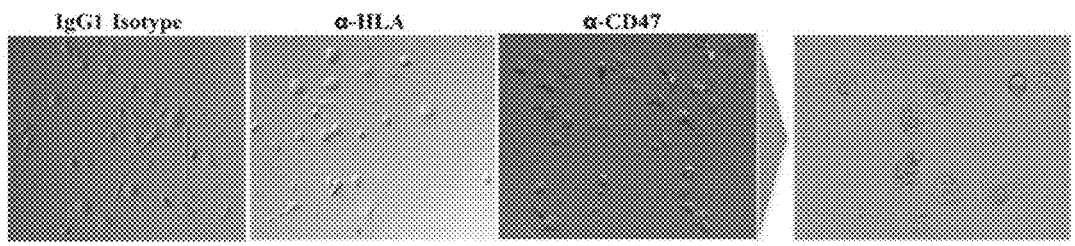
Figure 30B:
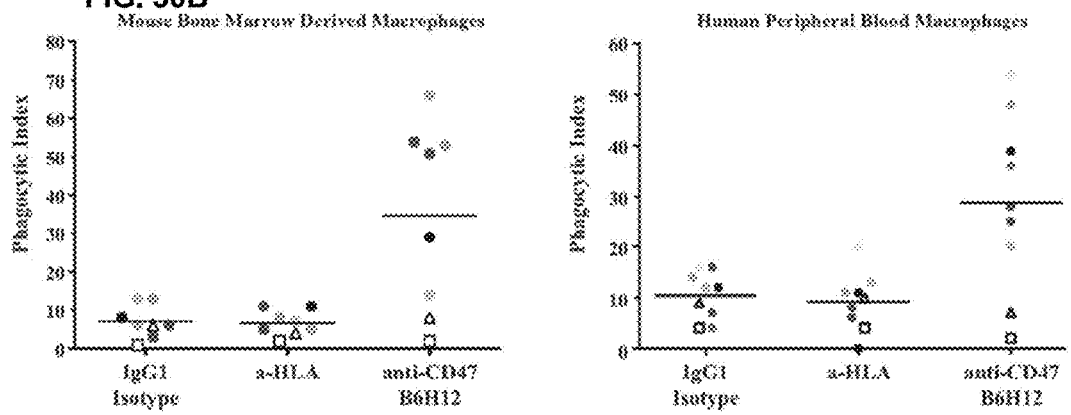
Figure 30C:
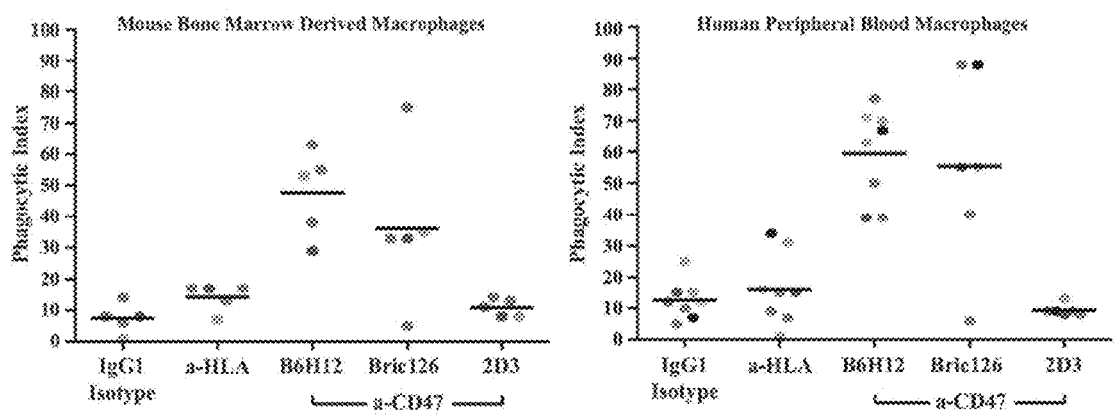
Figure 30D:
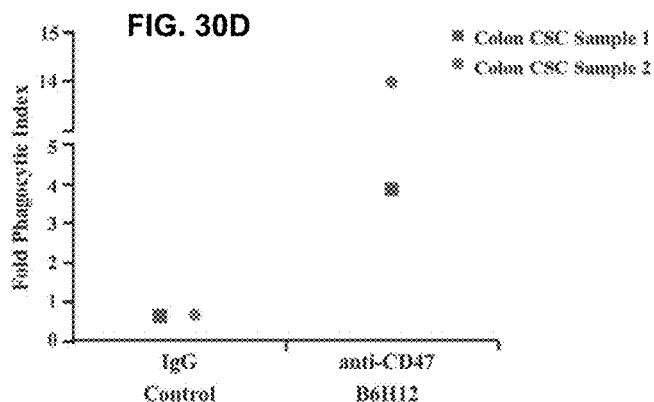

FIG. 30A-30D: Antibodies targeted to human CD47 enable the phagocytosis of human cancer cells. FIG. 30A: CFSE-labeled human patient bladder cancer cells were incubated with human macrophages in the presence of the indicated antibodies and assessed for the presence of tumor cells within macrophages. FIG. 30B-30D: Phagocytosis of patient bladder cancer cells (FIG. 30B), ovarian cancer cells (FIG. 30C), or colon cancer stem cells (FIG. 30D) resulting from indicated antibody treatment was quantified. Each dot color represents a different primary tumor sample. Open (non-colored) symbols represent normal tissue controls. The phagocytic index was determined as the number of CFSE labeled tumor cells present within 100 macrophages.

FIG. 31A-31F: Antibodies targeted to CD47 inhibit the growth of patient tumors. FIG. 31A-31D: Tumor cells from ovarian (FIG. 31A), pancreatic (FIG. 31B), breast (FIG. 31C), or colon (FIG. 31D) tumors were engrafted into immunodeficient mice. These mice were then treated with control IgG or anti-CD47 antibodies and tumor growth was assessed directly or by bioluminescence. In all cases, anti-CD47 antibody treatment substantially inhibited tumor growth. FIG. 31E-31F: Tumor cells from patient bladder were injected subcutaneously into immunodeficient mice and treated with the indicated antibodies. Anti-CD47 antibody treatment significantly inhibited metastasis to the lymph nodes (FIG. 31E) and formation of micrometastases in the lungs (FIG. 31F). The total number of metastases detected in each treatment group is indicated.

DETAILED DESCRIPTION OF THE EMBODIMENTS

Methods are provided to manipulate the phagocytosis of cells, including circulating hematopoietic cells. In some embodiments of the invention, leukemia cells, e.g. AML, B-ALL, T-ALL, etc. are targeted for phagocytosis by blocking CD47 on the cell surface. In other embodiments, cells of solid tumors are targeted for phagocytosis by blocking CD47 on the cell surface. In another embodiment, methods are provided for targeting or depleting leukemia stem cells, e.g. AML stem cells, ALL stem cells, etc., the method comprising contacting reagent blood cells with an antibody that specifically binds CD47 in order to target or deplete LSC. In another embodiment, methods are provided for targeting cancer cells of a tumor in a human subject by administering an antibody specific for CD47 to the subject.

In other embodiments, hematopoietic stem or progenitor cells are protected from phagocytosis in circulation by providing a host animal with a CD47 mimetic molecule, which interacts with SIRPα on phagocytic cells, such as, macrophages, and decreases phagocytosis.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

CD47 polypeptides. The three transcript variants of human CD 47 (variant 1, NM 001777; variant 2, NM 198793; and variant 3, NM 001025079) encode three isoforms of CD47 polypeptide. CD47 isoform 1 (NP 001768), the longest of the three isoforms, is 323 amino acids long. CD47 isoform 2 (NP 942088) is 305 amino acid long. CD47 isoform 3 is 312 amino acids long. The three isoforms are identical in sequence in the first 303 amino acids. Amino acids 1-8 comprise the signal sequence, amino acids 9-142 comprise the CD47 immunoglobulin like domain, which is the soluble fragment, and amino acids 143-300 is the transmembrane domain.

"CD47 mimetics" include molecules that function similarly to CD47 by binding and activating SIRPα receptor. Molecules useful as CD47 mimetics include derivatives, variants, and biologically active fragments of naturally occurring CD47. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural CD47 protein.

Fragments of the soluble CD47, particularly biologically active fragments and/or fragments corresponding to functional domains, are of interest. Fragments of interest will typically be at least about 10 aa to at least about 15 aa in length, usually at least about 50 aa in length, but will usually not exceed about 142 aa in length, where the fragment will have a stretch of amino acids that is identical to CD47. A fragment "at least 20 aa in length," for example, is intended to include 20 or more contiguous amino acids from, for example, the polypeptide encoded by a cDNA for CD47. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods.

A "fusion" polypeptide is a polypeptide comprising a polypeptide or portion (e.g., one or more domains) thereof fused or bonded to heterologous polypeptide. A fusion soluble CD47 protein, for example, will share at least one biological property in common with a native sequence soluble CD47 polypeptide. Examples of fusion polypeptides include immunoadhesins, as described above, which combine a portion of the CD47 polypeptide with an immunoglobulin sequence, and epitope tagged polypeptides, which comprise a soluble CD47 polypeptide or portion thereof fused to a "tag polypeptide". The tag polypeptide has enough residues to provide an epitope against which an antibody can be made, yet is short enough such that it does not interfere with biological activity of the CD47 polypeptide. Suitable tag polypeptides generally have at least six amino acid residues and usually between about 6-60 amino acid residues.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. The term "derivative" encompasses both amino acid sequence variants of polypeptide and covalent modifications thereof. Derivatives and fusion of soluble CD47 find use as CD47 mimetic molecules.

The first 142 amino acids of CD47 polypeptide comprise the extracellular region of CD47 (SEQ ID NO: 1). The three isoforms have identical amino acid sequence in the extracellular region, and thus any of the isoforms are can be used to generate soluble CD47. "Soluble CD47" is a CD47 protein that lacks the transmembrane domain. Soluble CD47 is secreted out of the cell expressing it instead of being localized at the cell surface. Soluble CD47 may be fused to another polypeptide to provide for added functionality, e.g. to increase the in vivo stability. Generally such fusion partners are a stable plasma protein that is capable of extending the in vivo plasma half-life of soluble CD47 protein when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide. Soluble CD47 fused to human Ig G1 has been described (Motegi S. et al. EMBO J. 22(11): 2634-2644).

Stable plasma proteins are proteins typically having about from 30 to 2,000 residues, which exhibit in their native environment an extended half-life in the circulation, i.e. greater than about 20 hours. Examples of suitable stable plasma proteins are immunoglobulins, albumin, lipoproteins, apolipoproteins and transferrin. The extracellular region of CD47 is typically fused to the plasma protein at the N-terminus of the plasma protein or fragment thereof which is capable of conferring an extended half-life upon the soluble CD47. Increases of greater than about 100% on the plasma half-life of the soluble CD47 are satisfactory.

Ordinarily, the soluble CD47 is fused C-terminally to the N-terminus of the constant region of immunoglobulins in place of the variable region(s) thereof, however N-terminal fusions may also find use. Typically, such fusions retain at least functionally active hinge, CH2 and CH3 domains of the constant region of an immunoglobulin heavy chain, which heavy chains may include IgG1, IgG2a, IgG2b, IgG3, IgG4, IgA, IgM, IgE, and IgD, usually one or a combination of proteins in the IgG class. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, the polypeptides may be synthesized according to known methods.

The precise site at which the fusion is made is not critical; particular sites may be selected in order to optimize the biological activity, secretion or binding characteristics of CD47. The optimal site will be determined by routine experimentation.

In some embodiments the hybrid immunoglobulins are assembled as monomers, or hetero- or homo-multimers, and particularly as dimers or tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of basic four-chain units held together by disulfide bonds. IgA immunoglobulin, and occasionally IgG immunoglobulin, may also exist in a multimeric form in serum. In the case of multimers, each four chain unit may be the same or different.

Suitable CD47 mimetics and/or fusion proteins may be identified by compound screening by detecting the ability of an agent to mimic the biological activity of CD47. One biological activity of CD47 is the activation of SIRPα receptor on macrophages. In vitro assays may be conducted as a first screen for efficacy of a candidate agent, and usually an in vivo assay will be performed to confirm the biological assay. Desirable agents are effective in temporarily blocking SIRP α receptor activation. Desirable agents are temporary in nature, e.g. due to biological degradation.

In vitro assays for CD47 biological activity include, e.g. inhibition of phagocytosis of porcine cells by human macrophages, binding to SIRP α receptor, SIRP α□ tyrosine phosphorylation, etc. An exemplary assay for CD47 biological activity contacts a human macrophage composition in the presence of a candidate agent. The cells are incubated with the candidate agent for about 30 minutes and lysed. The cell lysate is mixed with anti-human SIRP α□ antibodies to immunoprecipitate SIRP α. Precipitated proteins are resolved by SDS PAGE, then transferred to nitrocellulose and probed with antibodies specific for phosphotyrosine. A candidate agent useful as CD47mimetic increases SIRP α tyrosine phosphorylation by at least 10%, or up to 20%, or 50%, or 70% or 80% or up to about 90% compared to the level of phosphorylation observed in the absence of candidate agent. Another exemplary assay for CD47 biological activity measures phagocytosis of hematopoietic cells by human macrophages. A candidate agent useful as a CD47 mimetic results in the down regulation of phagocytosis by at least about 10%, at least about 20%, at least about 50%, at least about 70%, at least about 80%, or up to about 90% compared to level of phagocytosis observed in absence of candidate agent.

Polynucleotide encoding soluble CD47 or soluble CD47-Fc can be introduced into a suitable expression vector. The expression vector is introduced into a suitable cell. Expression vectors generally have convenient restriction sites located near the promoter sequence to provide for the insertion of polynucleotide sequences. Transcription cassettes may be prepared comprising a transcription initiation region, CD47 gene or fragment thereof, and a transcriptional termination region. The transcription cassettes may be introduced into a variety of vectors, e.g. plasmid; retrovirus, e.g. *lentivirus*; adenovirus; and the like, where the vectors are able to transiently or stably be maintained in the cells, usually for a period of at least about one day, more usually for a period of at least about several days to several weeks.

The various manipulations may be carried out in vitro or may be performed in an appropriate host, e.g. *E. coli*. After each manipulation, the resulting construct may be cloned, the vector isolated, and the DNA screened or sequenced to ensure the correctness of the construct. The sequence may be screened by restriction analysis, sequencing, or the like.

Soluble CD47 can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, protein G affinity chromatography, for example, hydroxylapatite chromatography and lectin chromatography. Most preferably, high performance liquid chromatography ("HPLC") is employed for purification.

Soluble CD47 can also be recovered from: products of purified cells, whether directly isolated or cultured; products of chemical synthetic procedures; and products produced by recombinant techniques from a prokaryotic or eukaryotic host, including, for example, bacterial, yeast higher plant, insect, and mammalian cells.

A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in binding.

Compounds of interest for screening include biologically active agents of numerous chemical classes, primarily organic molecules, although including in some instances inorganic molecules, organometallic molecules, immunoglobulins, chimeric CD47 proteins, CD47 related proteins, genetic sequences, etc. Also of interest are small organic molecules, which comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Compounds are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

By "manipulating phagocytosis" is meant an up-regulation or a down-regulation in phagocytosis by at least about 10%, or up to 20%, or 50%, or 70% or 80% or up to about 90% compared to level of phagocytosis observed in absence of intervention. Thus in the context of decreasing phagocytosis of circulating hematopoietic cells, particularly in a transplantation context, manipulating phagocytosis means a down-regulation in phagocytosis by at least about 10%, or up to 20%, or 50%, or 70% or 80% or up to about 90% compared to level of phagocytosis observed in absence of intervention.

CD47 inhibitors. Agents of interest as CD47 inhibitors include specific binding members that prevent the binding of CD47 with SIRP α receptor. The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). CD47 inhibitors useful in the methods of the invention include analogs, derivatives and fragments of the original specific binding member.

In a preferred embodiment, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH. Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. In addition, the antibodies or antigen binding fragments may be produced by genetic engineering. Humanized, chimeric, or xenogeneic human antibodies, which produce less of an immune response when administered to humans, are preferred for use in the present invention.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ricin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

The efficacy of a CD47 inhibitor is assessed by assaying CD47 activity. The above-mentioned assays or modified versions thereof are used. In an exemplary assay, AML SCs are incubated with bone marrow derived macrophages, in the presence or absence of the candidate agent. An inhibitor of the cell surface CD47 will up-regulate phagocytosis by at least about 10%, or up to 20%, or 50%, or 70% or 80% or up to about 90% compared to the phagocytosis in absence of the candidate agent. Similarly, an in vitro assay for levels of tyrosine phosphorylation of SIRPα will show a decrease in phosphorylation by at least about 10%, or up to 20%, or 50%, or 70% or 80% or up to about 90% compared to phosphorylation observed in absence of the candidate agent.

In one embodiment of the invention, the agent, or a pharmaceutical composition comprising the agent, is provided in an amount effective to detectably inhibit the binding of CD47 to SIRPα receptor present on the surface of phagocytic cells. The effective amount is determined via empirical testing routine in the art. The effective amount may vary depending on the number of cells being transplanted, site of transplantation and factors specific to the transplant recipient.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

Hematopoietic stem cells (HSC), as used herein, refers to a population of cells having the ability to self-renew, and to give rise to all hematopoietic lineages. Such cell populations have been described in detail in the art. Hematopoietic progenitor cells include the myeloid committed progenitors (CMP), the lymphoid committed progenitors (CLP), megakaryocyte progenitors, and multipotent progenitors. The earliest known lymphoid-restricted cell in adult mouse bone marrow is the common lymphocyte progenitor (CLP), and the earliest known myeloid-restricted cell is the common myeloid progenitor (CMP). Importantly, these cell populations possess an extremely high level of lineage fidelity in in vitro and in vivo developmental assays. A complete description of these cell subsets may be found in Akashi et al. (2000) Nature 404(6774):193, U.S. Pat. No. 6,465,247; and published application U.S. Ser. No. 09/956,279 (common myeloid progenitor); Kondo et al. (1997) Cell 91(5):661-7, and International application WO99/10478 (common lymphoid progenitor); and is reviewed by Kondo et al. (2003) Annu Rev Immunol. 21:759-806, each of which is herein specifically incorporated by reference. The composition may be frozen at liquid nitrogen temperatures and stored for long periods of time, being capable of use on thawing. For such a composition, the cells will usually be stored in a 10% DMSO, 50% FCS, 40% RPMI 1640 medium.

Populations of interest for use in the methods of the invention include substantially pure compositions, e.g. at least about 50% HSC, at least about 75% HSC, at least about 85% HSC, at least about 95% HSC or more; or may be combinations of one or more stem and progenitor cells populations, e.g. white cells obtained from apheresis, etc. Where purified cell populations are desired, the target population may be purified in accordance with known techniques. For example, a population containing white blood cells, particularly including blood or bone marrow samples, are stained with reagents specific for markers present of hematopoietic stem and progenitor cells, which markers are sufficient to distinguish the major stem and progenitor groups. The reagents, e.g. antibodies, may be detectably labeled, or may be indirectly labeled in the staining procedure.

Any combination of markers may be used that are sufficient to select for the stem/progenitor cells of interest. A marker combination of interest may include CD34 and CD38, which distinguishes hematopoietic stem cells, (CD34$^+$, CD38$^-$) from progenitor cells, which are CD34$^+$, CD38$^+$). HSC are lineage marker negative, and positive for expression of CD90.

In the myeloid lineage are three cell populations, termed CMPs, GMPs, and MEPs. These cells are CD34$^+$ CD38$^+$, they are negative for multiple mature lineage markers including early lymphoid markers such as CD7, CD10, and IL-7R, and they are further distinguished by the markers CD45RA, an isoform of CD45 that can negatively regulate at least some classes of cytokine receptor signaling, and IL-3R. These characteristics are CD45RA$^-$ IL-3R$\alpha^{lo}$ (CMPs), CD45RA$^+$IL-3R$\alpha^{lo}$ (GMPs), and CD45RA$^-$ IL-3R$\alpha^-$ (MEPs). CD45RA$^-$ IL-3R$\alpha^{lo}$ cells give rise to GMPs and MEPs and at least one third generate both GM and MegE colonies on a single-cell level. All three of the myeloid lineage progenitors stain negatively for the markers Thy-1 (CD90), IL-7R$\alpha$ (CD127); and with a panel of lineage markers, which lineage markers may include CD2; CD3; CD4; CD7; CD8; CD10; CD11b; CD14; CD19; CD20; CD56; and glycophorin A (GPA) in humans and CD2; CD3; CD4; CD8; CD19; IgM; Ter110; Gr-1 in mice. With the exception of the mouse MEP subset, all of the progenitor cells are CD34 positive. In the mouse all of the progenitor subsets may be further characterized as Sca-1 negative, (Ly-6E and Ly-6A), and c-kit high. In the human, all three of the subsets are CD38$^+$.

Common lymphoid progenitors, CLP, express low levels of c-kit (CD117) on their cell surface. Antibodies that specifically bind c-kit in humans, mice, rats, etc. are known in the art. Alternatively, the c-kit ligand, steel factor (Slf) may be used to identify cells expressing c-kit. The CLP cells express high levels of the IL-7 receptor alpha chain (CDw127). Antibodies that bind to human or to mouse CDw127 are known in the art. Alternatively, the cells are identified by binding of the ligand to the receptor, IL-7. Human CLPs express low levels of CD34. Antibodies specific for human CD34 are commercially available and well known in the art. See, for example, Chen et al. (1997) *Immunol Rev* 157:41-51. Human CLP cells are also characterized as CD38 positive and CD10 positive. The CLP subset also has the phenotype of lacking expression of lineage specific markers, exemplified by B220, CD4, CD8, CD3, Gr-1 and Mac-1. The CLP cells are characterized as lacking expression of Thy-1, a marker that is characteristic of hematopoietic stem cells. The phenotype of the CLP may be further characterized as Mel-14$^-$, CD43$^{lo}$, HSA$^{lo}$, CD45$^+$ and common cytokine receptor $\gamma$ chain positive.

Megakaryocyte progenitor cells (MKP) cells are positive for CD34 expression, and tetraspanin CD9 antigen. The CD9 antigen is a 227-amino acid molecule with 4 hydrophobic domains and 1 N-glycosylation site. The antigen is widely expressed, but is not present on certain progenitor cells in the hematopoietic lineages. The MKP cells express CD41, also referred to as the glycoprotein IIb/IIIa integrin, which is the platelet receptor for fibrinogen and several other extracellular matrix molecules, for which antibodies are commercially available, for example from BD Biosciences, Pharmingen, San Diego, Calif., catalog number 340929, 555466. The MKP cells are positive for expression of CD117, which recognizes the receptor tyrosine kinase c-Kit. Antibodies are commercially available, for example from BD Biosciences, Pharmingen, San Diego, Calif., Cat. No. 340529. MKP cells are also lineage negative, and negative for expression of Thy-1 (CD90).

The phrase "solid tumor" as used herein refers to an abnormal mass of tissue that usually does not contain cysts or liquid areas. Solid tumors may be benign or malignant. Different types of solid tumors are named for the type of cells that form them. Examples of solid tumors are sarcomas, carcinomas, lymphomas etc.

Anti-CD47 antibodies. Certain antibodies that bind CD47 prevent its interaction with SIRP$\alpha$ receptor. Antibodies include free antibodies and antigen binding fragments derived therefrom, and conjugates, e.g. pegylated antibodies, drug, radioisotope, or toxin conjugates, and the like.

Monoclonal antibodies directed against a specific epitope, or combination of epitopes, will allow for the targeting and/or depletion of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like.

Humanized versions of such antibodies are also within the scope of this invention. Humanized antibodies are especially useful for in vivo applications in humans due to their low antigenicity.

The phrase "bispecific antibody" refers to a synthetic or recombinant antibody that recognizes more than one protein. Examples include bispecific antibodies 2B1, 520C9xH22, mDX-H210, and MDX447. Bispecific antibodies directed against a combination of epitopes, will allow for the targeting and/or depletion of cellular populations expressing the combination of epitopes. Exemplary bi-specific antibodies include those targeting a combination of CD47 and a cancer cell marker, such as, CD96, CD97, CD99, PTHR2, HAVCR2 etc. Generation of bi-specific antibody is described in the literature, for example, in U.S. Pat. No. 5,989,830, U.S. Pat. No. 5,798,229, which are incorporated herein by reference.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "recipient", "individual", "subject", "host", and "patient", used interchangeably herein and refer to any mammalian subject for whom diagnosis, treatment, or therapy is desired, particularly humans.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

Cancers of interest for treatment by the methods of the invention, e.g. treatment with an agent that binds to cell surface CD47 to increase phagocytosis of the cancer cells; include leukemias, particularly acute leukemias such as T-ALL, B-ALL, AML, etc.; lymphomas (Hodgkins and non-Hodgkins); sarcomas; melanomas; adenomas; carcinomas of solid tissue including ovarian carcinoma, breast carcinoma, pancreatic carcinoma, colon carcinoma, squamous cell carcinoma, transitional cell carcinoma, etc., hypoxic tumors, squamous cell carcinomas of the mouth, throat, larynx, and lung, genitourinary cancers such as cervical and bladder cancer, hematopoietic cancers, head and neck cancers, and nervous system cancers, such as gliomas, astrocytomas, meningiomas, etc., benign lesions such as papillomas, and the like.

As used herein, a "target cell" is a cell expressing CD47 on the surface, where masking or otherwise altering the CD47 positive phenotype results in altered phagocytosis. Usually a target cell is a mammalian cell, preferably a human cell.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, rodents, primates, farm animals, sport animals, and pets.

An "effective amount" is an amount sufficient to effect beneficial or desired clinical results. An effective amount can be administered in one or more administrations. For purposes of this invention, an effective amount of a CD47 binding agent is an amount that is sufficient to palliate, ameliorate, stabilize, reverse, slow or delay the progression of the disease state by modulating phagocytosis of a target cell.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment. "Palliating" a disease means that the extent and/or undesirable clinical manifestations of a disease state are lessened and/or time course of the progression is slowed or lengthened, as compared to not administering the methods of the present invention.

"Therapeutic target" refers to a gene or gene product that, upon modulation of its activity (e.g., by modulation of expression, biological activity, and the like), can provide for modulation of the cancerous phenotype. As used throughout, "modulation" is meant to refer to an increase or a decrease in the indicated phenomenon (e.g., modulation of a biological activity refers to an increase in a biological activity or a decrease in a biological activity).

Methods for Transplantation

Methods are provided to manipulate phagocytosis of circulating hematopoietic cells. In some embodiments of the invention the circulating cells are hematopoietic stem cells, or hematopoietic progenitor cells, particularly in a transplantation context, where protection from phagocytosis is desirable. In other embodiments the circulating cells are leukemia cells, particularly acute myeloid leukemia (AML), where increased phagocytosis is desirable.

In some embodiments of the invention, hematopoietic stem or progenitor cells are protected from phagocytosis in circulation by providing a host animal with a CD47 mimetic molecule, which interacts with SIRPα on macrophages and decreases macrophage phagocytosis. The CD47 mimetic may be soluble CD47; CD47 coated on the surface of the cells to be protected, a CD47 mimetic that binds to SIRPα at the CD47 binding site, and the like. In some embodiments of the invention, CD47 is provided as a fusion protein, for example soluble CD47 fused to an Fc fragment, e.g., IgG1 Fc, IgG2 Fc, Ig A Fc etc.

Methods for generating proteins lacking the transmembrane region are well known in the art. For example, a soluble CD47 can be generated by introducing a stop codon immediately before the polynucleotide sequence encoding the transmembrane region. Alternatively, the polynucleotide sequence encoding the transmembrane region can be replaced by a polynucleotide sequence encoding a fusion protein such as IgG1 Fc. Sequence for Fc fragments from different sources are available via publicly accessible database including Entrez, Embl, etc. For example, mRNA encoding human IgG1 Fc fragment is provided by accession number X70421.

The subject invention provide for methods for transplanting hematopoietic stem or progenitor cells into a mammalian recipient. A need for transplantation may be caused by genetic or environmental conditions, e.g. chemotherapy, exposure to radiation, etc. The cells for transplantation may be mixtures of cells, e.g. buffy coat lymphocytes from a donor, or may be partially or substantially pure. The cells may be autologous cells, particularly if removed prior to cytoreductive or other therapy, or allogeneic cells, and may be used for hematopoietic stem or progenitor cell isolation and subsequent transplantation.

The cells may be combined with the soluble CD47 mimetic prior to administration. For example, the cells may be combined with the mimetic at a concentration of from about 10 µg/ml, about 100 µg/ml, about 1 mg/ml, about 10 mg/ml, etc., at a temperature of from about 4°, about 10°, about 25° about 37°, for a period of time sufficient to coat the cells, where in some embodiments the cells are maintained on ice. In other embodiments the cells are contacted with the CD47 mimetic immediately prior to introduction into the recipient, where the concentrations of mimetic are as described above.

The composition comprising hematopoietic stem or progenitor cells and a CD47 mimetic is administered in any physiologically acceptable medium, normally intravascularly, although they may also be introduced into bone or other convenient site, where the cells may find an appropriate site for regeneration and differentiation. Usually, at least $1 \times 10^5$ cells will be administered, preferably $1 \times 10^6$ or more. The composition may be introduced by injection, catheter, or the like.

Myeloproliferative Disorders, Leukemias, and Myelodysplastic Syndrome

Acute leukemias are rapidly progressing leukemia characterized by replacement of normal bone marrow by blast cells of a clone arising from malignant transformation of a hematopoietic cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas). In addition to CD47, we have discovered a number of markers specific to AML SC. These include CD96, CD97, CD99, PTHR2, HAVCR2 etc. These markers have been disclosed in U.S. Patent Application No. 61/011, 324, filed on Jan. 15, 2008 and are hereby incorporated by reference.

The presenting symptoms are usually nonspecific (e.g., fatigue, fever, malaise, weight loss) and reflect the failure of normal hematopoiesis. Anemia and thrombocytopenia are very common (75 to 90%). The WBC count may be decreased, normal, or increased. Blast cells are usually found in the blood smear unless the WBC count is markedly decreased. The blasts of ALL can be distinguished from those of AML by histochemical studies, cytogenetics, immunophenotyping, and molecular biology studies. In addition to smears with the usual stains, terminal transferase, myeloperoxidase, Sudan black B, and specific and nonspecific esterase.

ALL is the most common malignancy in children, with a peak incidence from ages 3 to 5 yr. It also occurs in adolescents and has a second, lower peak in adults. Typical treatment emphasizes early introduction of an intensive multidrug regimen, which may include prednisone, vincristine, anthracycline or asparaginase. Other drugs and combinations are cytarabine and etoposide, and cyclophosphamide. Relapse usually occurs in the bone marrow but may also occur in the CNS or testes, alone or concurrent with bone marrow. Although second remissions can be induced in many children, subsequent remissions tend to be brief.

The incidence of AML increases with age; it is the more common acute leukemia in adults. AML may be associated with chemotherapy or irradiation (secondary AML). Remission induction rates are lower than with ALL, and long-term disease-free survival reportedly occurs in only 20 to 40% of patients. Treatment differs most from ALL in that AML responds to fewer drugs. The basic induction regimen includes cytarabine; along with daunorubicin or idarubicin. Some regimens include 6-thioguanine, etoposide, vincristine, and prednisone.

Polycythemia vera (PV) is an idiopathic chronic myeloproliferative disorder characterized by an increase in Hb concentration and RBC mass (erythrocytosis). PV occurs in about 2.3/100,000 people per year; more often in males (about 1.4:1). The mean age at diagnosis is 60 yr (range, 15 to 90 yr; rarely in childhood); 5% of patients are <40 yr at onset. The bone marrow sometimes appears normal but usually is hypercellular; hyperplasia involves all marrow elements and replaces marrow fat. There is increased production and turnover of RBCs, neutrophils, and platelets. Increased megakaryocytes may be present in clumps. Marrow iron is absent in >90% of patients, even when phlebotomy has not been performed.

Studies of women with PV who are heterozygous at the X-chromosome-linked locus for G6PD have shown that RBCs, neutrophils, and platelets have the same G6PD isoenzyme, supporting a clonal origin of this disorder at a pluripotent stem cell level.

Eventually, about 25% of patients have reduced RBC survival and fail to adequately increase erythropoiesis; anemia and myelofibrosis develop. Extramedullary hemopoiesis occurs in the spleen, liver, and other sites with the potential for blood cell formation.

Without treatment, 50% of symptomatic patients die within 18 mo of diagnosis. With treatment, median survival is 7 to 15 yr. Thrombosis is the most common cause of death, followed by complications of myeloid metaplasia, hemorrhage, and development of leukemia.

The incidence of transformation into an acute leukemia is greater in patients treated with radioactive phosphate ($^{32}$P) or alkylating agents than in those treated with phlebotomy alone. PV that transforms into acute leukemia is more resistant to induction chemotherapy than de novo leukemia.

Because PV is the only form of erythrocytosis for which myelosuppressive therapy may be indicated, accurate diagnosis is critical. Therapy must be individualized according to age, sex, medical status, clinical manifestations, and hematologic findings.

Myelodysplastic syndrome (MDS) is a group of syndromes (preleukemia, refractory anemias, Ph-negative chronic myelocytic leukemia, chronic myelomonocytic leukemia, myeloid metaplasia) commonly seen in older patients. Exposure to carcinogens may by be implicated. MDS is characterized by clonal proliferation of hematopoietic cells, including erythroid, myeloid, and megakaryocytic forms. The bone marrow is normal or hypercellular, and ineffective hematopoiesis causes variable cytopenias, the most frequent being anemia. The disordered cell production is also associated with morphologic cellular abnormalities in marrow and blood. Extramedullary hematopoiesis may occur, leading to hepatomegaly and splenomegaly. Myelofibrosis is occasionally present at diagnosis or may develop during the course of MDS. The MDS clone is unstable and tends to progress to AML.

Anemia is the most common clinical feature, associated usually with macrocytosis and anisocytosis. Some degree of thrombocytopenia is usual; on blood smear, the platelets vary in size, and some appear hypogranular. The WBC count may be normal, increased, or decreased. Neutrophil cytoplasmic granularity is abnormal, with anisocytosis and variable numbers of granules. Eosinophils also may have abnormal granularity. A monocytosis is characteristic of the chronic myelomonocytic leukemia subgroup, and immature myeloid cells may occur in the less well differentiated subgroups. The prognosis is highly dependent on classification and on any associated disease. Response of MDS to AML chemotherapy is similar to that of AML, after age and karyotype are considered.

Treatment of Cancer

The invention provides methods for reducing growth of cancer cells by increasing their clearance by phagocytosis, through the introduction of a CD47 blocking agent, e.g. an anti-CD47 antibody. In certain embodiments the cancer cells may be AML stem cells. In other embodiments, the cancer cells may be those of a solid tumor, such as carcinomas, glioblastoma, melanoma, etc. By blocking the activity of CD47, the downregulation of phagocytosis that is found with certain tumor cells, e.g. AML cells, is prevented.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with AML, etc.

Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

As an alternative embodiment, an agent, e.g. a chemotherapeutic drug that reduces cancer cell growth, can be targeted to a cancer cell by conjugation to a CD47 specific antibody. Thus, in some embodiments, the invention provides a method of delivering a drug to a cancer cell, comprising administering a drug-antibody complex to a subject, wherein the antibody is specific for a cancer-associated polypeptide, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art and need not be elaborated upon herein.

In certain embodiments, a bi-specific antibody may be used. For example a bi-specific antibody in which one antigen binding domain is directed against CD47 and the other antigen binding domain is directed against a cancer cell marker, such as, CD96 CD97, CD99, PTHR2, HAVCR2 etc. may be used.

Depletion of AMLSC is useful in the treatment of AML. Depletion can be achieved by several methods. Depletion is defined as a reduction in the target population by up to about 30%, or up to about 40%, or up to about 50%, or up to about 75% or more. An effective depletion is usually determined by the sensitivity of the particular disease condition to the levels of the target population. Thus in the treatment of certain conditions a depletion of even about 20% could be beneficial.

A CD47 specific agent that specifically depletes the targeted AMLSC is used to contact the patient blood in vitro or in vivo, wherein after the contacting step, there is a reduction in the number of viable AMLSC in the targeted population. An effective dose of antibodies for such a purpose is sufficient to decrease the targeted population to the desired level, for example as described above. Antibodies for such purposes may have low antigenicity in humans or may be humanized antibodies.

In one embodiment of the invention, antibodies for depleting target population are added to patient blood in vivo. In another embodiment, the antibodies are added to the patient blood ex vivo. Beads coated with the antibody of interest can be added to the blood, target cells bound to these beads can then be removed from the blood using procedures common in the art. In one embodiment the beads are magnetic and are removed using a magnet. Alternatively, when the antibody is biotinylated, it is also possible to indirectly immobilize the antibody onto a solid phase which has adsorbed avidin, streptavidin, or the like. The solid phase, usually agarose or sepharose beads are separated from the blood by brief centrifugation. Multiple methods for tagging antibodies and removing such antibodies and any cells bound to the antibodies are routine in the art. Once the desired degree of depletion has been achieved, the blood is returned to the patient. Depletion of target cells ex vivo decreases the side effects such as infusion reactions associated with the intravenous administration. An additional advantage is that the repertoire of available antibodies is expanded significantly as this procedure does not have to be limited to antibodies with low antigenicity in humans or humanized antibodies.

Example 1

CD47 is a Marker of Myeloid Leukemias

Materials and Methods

Immunohistochemistry. Cytospins of double sorted myeloid progenitor populations (CMP, GMP), IL-3Rα high CD45 RA+ cells and CD14+c-kit+lin− cells were performed using a Shandon cytospin apparatus. Cytospins were stained with Giemsa diluted ⅕ with H$_2$O for 10 min followed by staining with May-Grunwald for 20 minutes. Cytospins were analyzed with the aid of a Zeiss microscope.

Human Bone Marrow and Peripheral Blood Samples. Normal bone marrow samples were obtained with informed consent from 20-25 year old paid donors who were hepatitis A, B, C and HIV negative by serology (All Cells). CMML bone marrow samples were obtained with informed consent, from previously untreated patients, at Stanford University Medical Center.

Human Bone Marrow HSC and Myeloid Progenitor Flow-Cytometric Analysis and Cell Sorting. Mononuclear fractions were extracted following Ficoll density centrifugation according to standard methods and analyzed fresh or subsequent to rapid thawing of samples previously frozen in 90% FCS and 10% DMSO in liquid nitrogen. In some cases, CD34+ cells were enriched from mononuclear fractions with the aid of immunomagnetic beads (CD34+ Progenitor Isolation Kit, Miltenyi Biotec, Bergisch-Gladbach, Germany). Prior to FACS analysis and sorting, myeloid progenitors were stained with lineage marker specific phycoerythrin (PE)-Cy5-conjugated antibodies including CD2 RPA-2.10; CD11b, ICRF44; CD20, 2H7; CD56, B159; GPA, GA-R2 (Becton Dickinson—PharMingen, San Diego), CD3,S4.1; CD4, S3.5; CD7, CD7-6B7; CD8, 3B5; CD10, 5-1B4, CD14, TUK4; CD19, SJ25-C1 (Caltag, South San Francisco, Calif.) and APC-conjugated anti-CD34, HPCA-2 (Becton Dickinson-PharMingen), biotinylated anti-CD38, HIT2 (Caltag) in addition to PE-conjugated anti-IL-3Rα, 9F5 (Becton Dickinson-ParMingen) and FITC-conjugated anti-CD45RA, MEM56 (Caltag) followed by staining with Streptavidin—Texas Red to visualize CD38-BIO stained cells and resuspension in propidium iodide to exclude dead cells. Unstained samples and isotype controls were included to assess background fluorescence.

Following staining, cells were analyzed and sorted using a modified FACS Vantage (Becton Dickinson Immunocytometry Systems, Mountain View, Calif.) equipped with a 599 nm dye laser and a 488 nm argon laser. Double sorted progenitor cells (HSC) were identified as CD34+ CD38+ and lineage negative. Common myeloid progenitors (CMP) were identified based on CD34+ CD38+ IL-3Rα+ CD45RA– lin– staining and their progeny including granulocyte/macrophage progenitors (GMP) were CD34+CD38+ IL-3Rα+ CD45RA+ while megakaryocyte/erythrocyte progenitors (MEP) were identified based on CD34+ CD38+ IL-3Rα– CD45RA– lin– staining (Manz, PNAS 11872).

CD47 Expression by Normal Versus Myeloproliferative and AML Progenitors

Peripheral blood and bone marrow samples were obtained with informed consent from patients with myeloproliferative disorders and acute myelogenous leukemia at Stanford University Medical Center according to Stanford IRB and HIPAA regulations. Peripheral blood or bone marrow mononuclear cells ($1-5\times10^6$ cells) were stained with lineage cocktail as above but excluding CD7, CD11b and CD14. Subsequently, samples were stained with CD14 PE (1/25), CD47 FITC (1/25), CD38 Bio (Bio) and c-kit APC (1/25) or CD34 APC or FITC (1/50) for 45 min followed by washing and staining with Streptavidin Texas Red (1/25) for 45 min and finally resuspension in propidium iodide.

Discussion

Here we show that CD47 overexpression is characteristic of progression of human myeloproliferative disorders to AML (see FIGS. 1-5B). CD47 controls integrin function but also the ability of macrophages to phagocytose cells, depending on the level of CD47 expression. Thus, aberrant CD47 expression may allow LSC to evade both innate and adaptive host immunity.

Human CD47 expression analysis was performed via FACS on human normal, pre-leukemic myeloproliferative disorder (MPD) or AML HSC, progenitors and lineage positive cells derived from marrow or peripheral blood. MPD samples (n=63) included polycythemia vera (PV; n=15), post-polycythemic myeloid metaplasia/myelofibrosis (PPMM/MF; n=5), essential thrombocythemia (ET; n=8), atypical chronic myelogenous leukemia (aCML; n=2), CML (n=7), chronic eosinophilic leukemia (CEL; n=1), chronic myelomonocytic leukemia (CMML; n=13) and acute myelogenous leukemia (AML; n=12). As we have observed with the transgenic leukemic mouse models, progression of human myeloproliferative disorders to AML (n=12) was associated with an expansion of the GMP pool (70.6%+/– S.D. 2.15) compared with normal bone marrow (14.7%+/– S.D. 2.3). Furthermore, FACS analysis revealed that CD47 expression first increased 1.7 fold in AML compared with normal HSC and then increased to 2.2 fold greater than normal with commitment of AML progenitors to the myeloid lineage. CD47 was over-expressed by AML primitive progenitors and their progeny but not by the majority of MPD (MFI 2.3+/– S.D. 0.43) compared with normal bone marrow (MFI 1.9+/– S.D. 0.07). Thus, increased CD47 expression is a useful diagnostic marker for progression to AML and in addition represents a novel therapeutic target.

Example 2

Human and Mouse Leukemias Upregulate CD47 to Evade Macrophage Killing

CD47 Facilitates Engraftment, Inhibits Phagocytosis, and is More Highly Expressed on AML LSC. We determined expression of CD47 on human AML LSC and normal HSC by flow cytometry. HSC (Lin–CD34+CD38–CD90+) from three samples of normal human mobilized peripheral blood and AML LSC (Lin–CD34+CD38–CD90–) from seven samples of human AML were analyzed for surface expression of CD47 (FIG. 6). CD47 was expressed at low levels on the surface of normal HSC; however, on average, it was approximately 5-fold more highly expressed on AML LSC, as well as bulk leukemic blasts.

Figure 1:
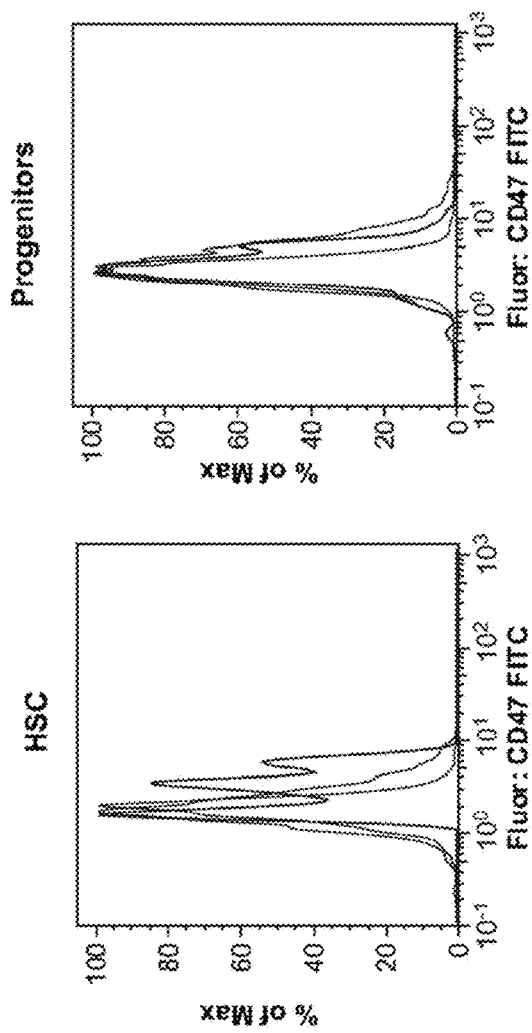
FIG. 1. FACS analysis of human HSC and progenitor CD47 expression from Myelodysplastic syndrome (MDS, blue), Chronic Myelogenous Leukemia, Accelerated Phase (CML AP, green) and normal bone marrow (red).
Figure 2:
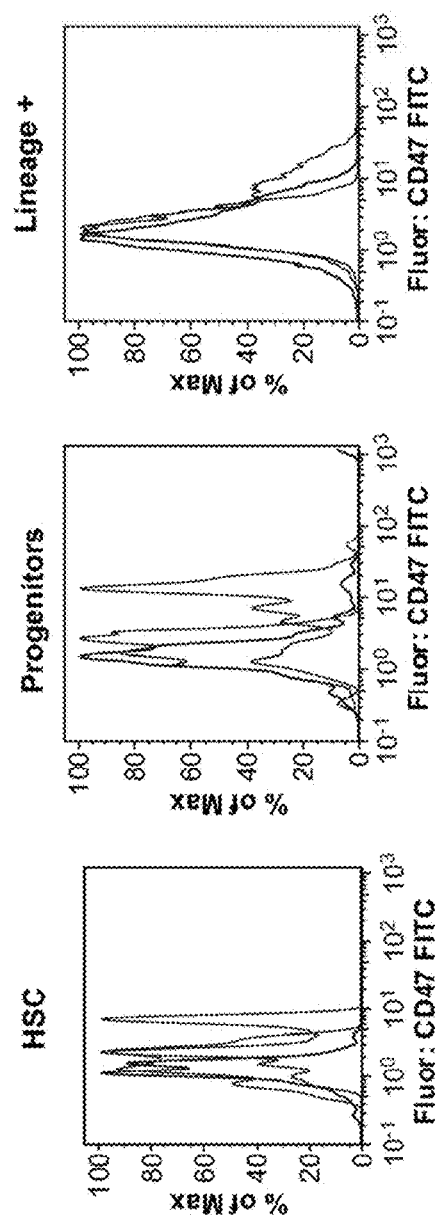
FIG. 2. ET vs. PV. FACS analysis of CD47 expression by human myeloproliferative disorders such as essential thrombocythemia (ET, blue) and polycythemia vera (PV, green) HSC, progenitor and lineage positive cells compared with human normal bone marrow (red).
Figure 4:
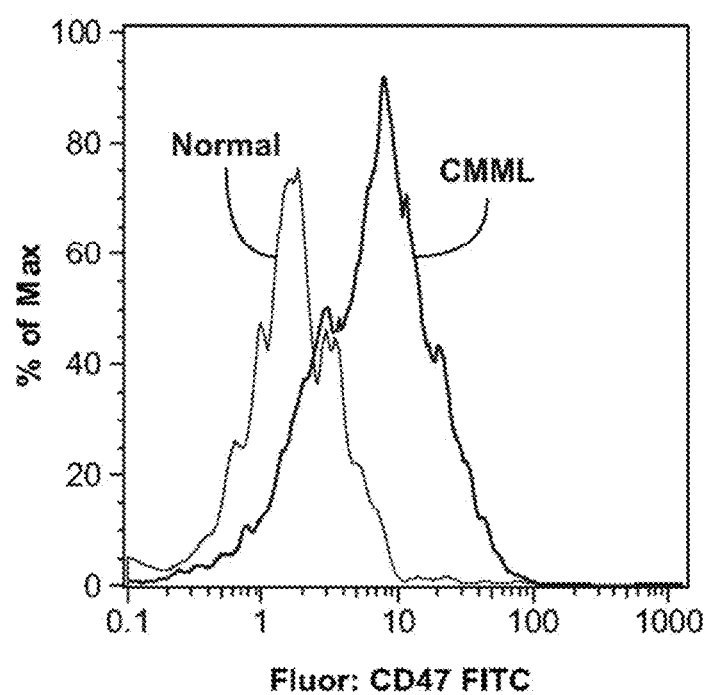
FIG. 4. Increased CD47 Expression by CMML Progenitors (blue) compared with normal bone marrow (red) with disease progression.
Figure 5A:
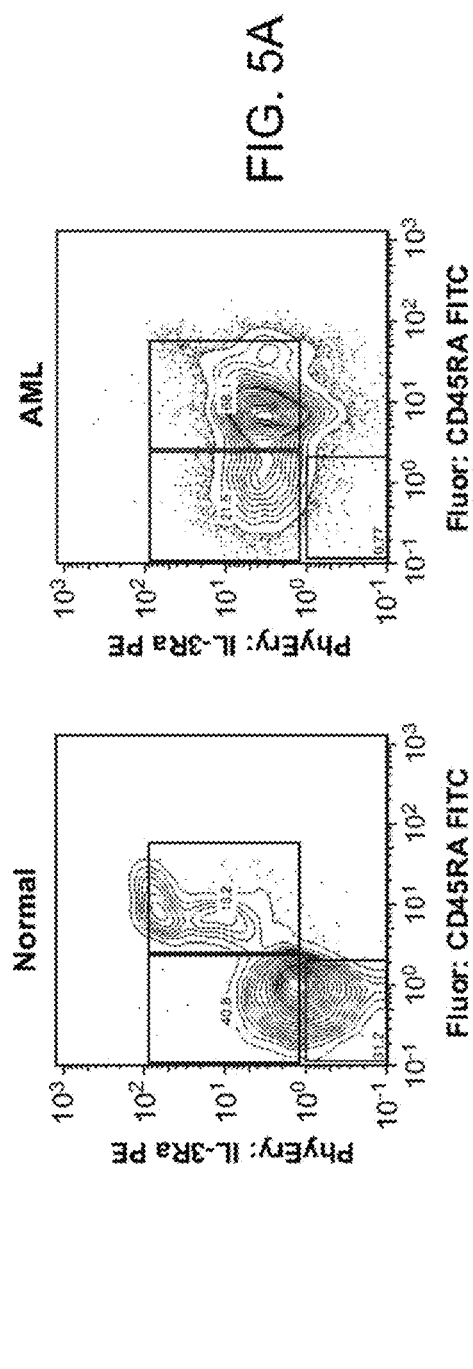
FIG. 5A-5B.
Figure 5B:
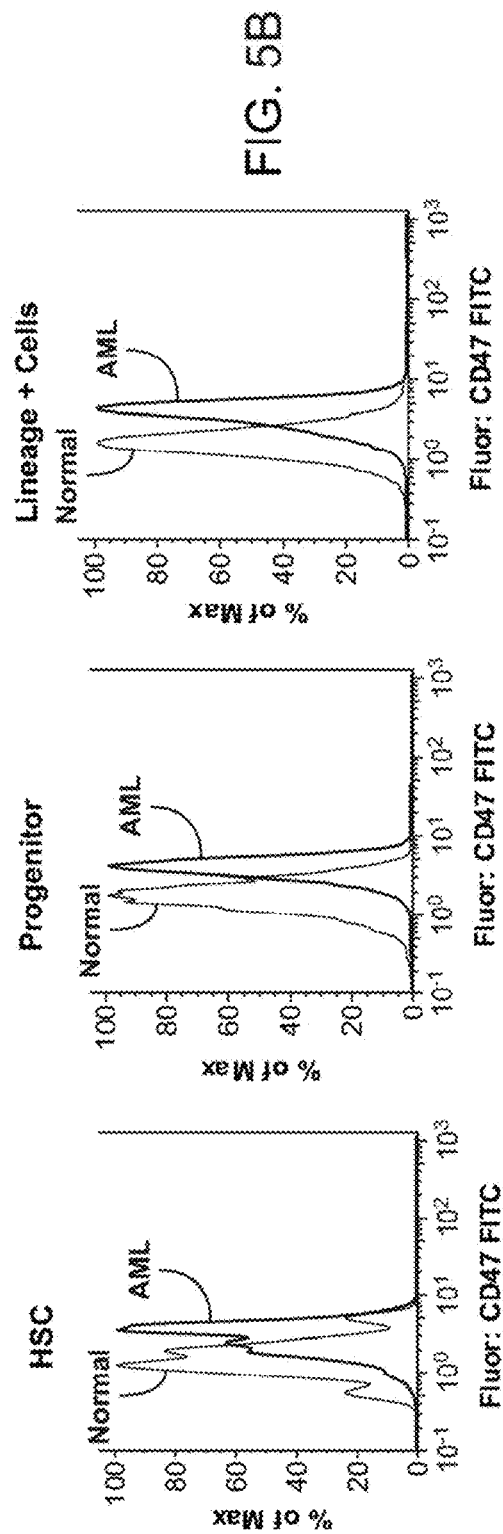
Figures 7A, 7B:
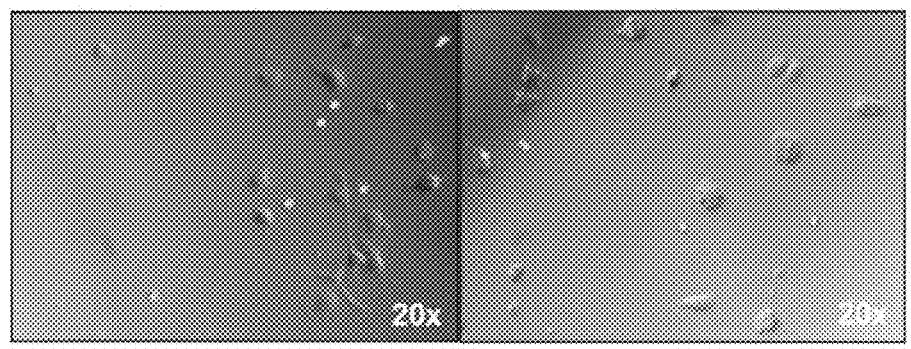
FIG. 7A-7C. Anti-CD47 Antibody Stimulates In Vitro Macrophage Phagocytosis of Primary Human AML LSC. AML LSC were purified by FACS from two primary human AML samples, labeled with the fluorescent dye CFSE, and incubated with mouse bone marrow-derived macrophages either in the presence of an isotype control (FIG. 7A) or anti-CD47 antibody (FIG. 7B). These cells were assessed by immunofluorescence microscopy for the presence of fluorescently labeled LSC within the macrophages.
Figure 7C:
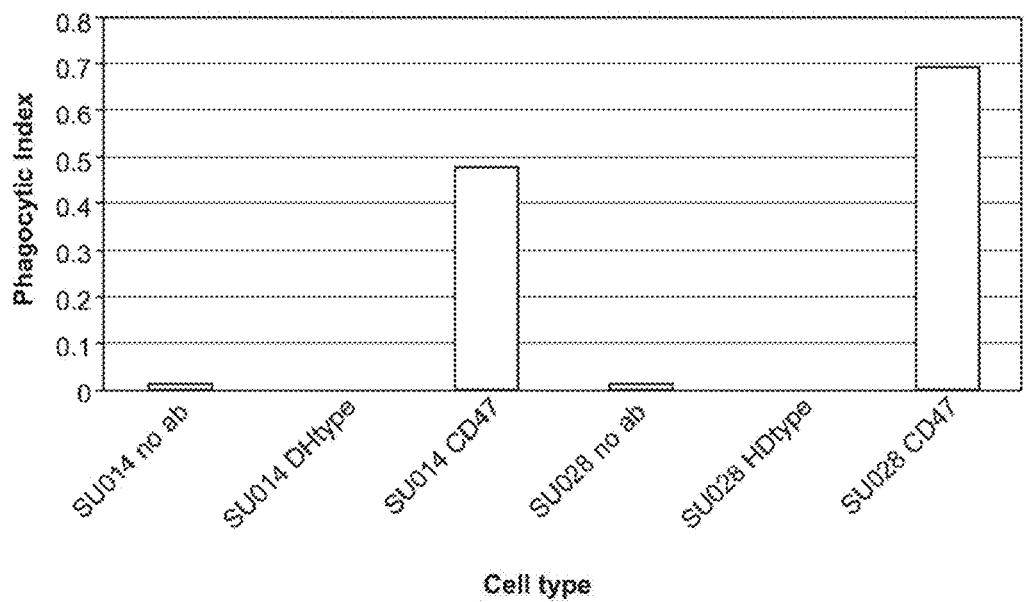

Anti-Human CD47 Monoclonal Antibody Stimulates Phagocytosis and Inhibits Engraftment of AML LSC. In order to test the model that CD47 overexpression on AML LSC prevents phagocytosis of these cells through its interaction with SIRPα on effector cells, we have utilized a monoclonal antibody directed against CD47 known to disrupt the CD47-SIRPα interaction. The hybridoma producing a mouse-anti-human CD47 monoclonal antibody, termed B6H12, was obtained from ATCC and used to produce purified antibody. First, we conducted in vitro phagocytosis assays. Primary human AML LSC were purified by FACS from two samples of human AML, and then loaded with the fluorescent dye CFSE. These cells were incubated with mouse bone marrow-derived macrophages and monitored using immunofluorescence microscopy (FIG. 7) and flow cytometry (FIG. 9) to identify phagocytosed cells. In both cases, no phagocytosis was observed in the presence of an isotype control antibody; however, significant phagocytosis was detected with the addition of the anti-CD47 antibody (FIG. 9). Thus, blockage of human CD47 with a monoclonal antibody is capable of stimulating the phagocytosis of these cells by mouse macrophages.

We next investigated the ability of the anti-CD47 antibody to inhibit AML LSC engraftment in vivo. Two primary human AML samples were either untreated or coated with the anti-CD47 antibody prior to transplantation into NOG newborn mice. 13 weeks later, the mice were sacrificed and analyzed for human leukemia bone marrow engraftment by flow cytometry (FIG. 10). The control mice demonstrated leukemic engraftment while mice transplanted with the anti-CD47-coated cells showed little to no engraftment. These data indicate that blockade of human CD47 with a monoclonal antibody is able to inhibit AML LSC engraftment.

CD96 is a Human Acute Myeloid Leukemia Stem Cell-Specific Cell Surface Molecule. CD96, originally termed Tactile, was first identified as a T cell surface molecule that is highly upregulated upon T cell activation. CD96 is expressed at low levels on resting T and NK cells and is strongly upregulated upon stimulation in both cell types. It is not expressed on other hematopoietic cells, and examination of its expression pattern showed that it is only otherwise present on some intestinal epithelia. The cytoplasmic domain of CD96 contains a putative ITIM motif, but it is not know if this functions in signal transduction. CD96 promotes adhesion of NK cells to target cells expressing CD155, resulting in stimulation of cytotoxicity of activated NK cells.

Preferential Cell Surface Expression of Molecules Identified from Gene Expression Analysis. Beyond CD47 and CD96, several molecules described in U.S. Patent Application No. 61/011,324 are known to be expressed on AML LSC, including: CD123, CD44, CD99 and CD33.

Tumor progression is characterized by several hallmarks, including growth signal independence, inhibition of apoptosis, and evasion of the immune system, among others. We show here that expression of CD47, a ligand for the macrophage inhibitory signal regulatory protein alpha (SIRPα) receptor, is increased in human and mouse myeloid leukaemia and allows cells to evade phagocytosis and increase their tumorigenic potential. CD47, also known as integrin associated protein (IAP), is an immunoglobulin-like transmembrane pentaspanin that is broadly expressed in mammalian tissues. We provide evidence that CD47 is upregulated in mouse and human myeloid leukaemia stem and progenitor cells, as well as leukemic blasts. Consistent with a biological role for CD47 in myeloid leukaemia development and maintenance, we demonstrate that ectopic overexpression of CD47 allows a myeloid leukaemia cell line to grow in mice that are T, B, and NK-cell deficient, whereas it is otherwise cleared rapidly when transplanted into these recipients. The leukemogenic potential of CD47 is also shown to be dose-dependent, as higher expressing clones have greater tumor forming potential than lower expressing clones. We also show that CD47 functions in promoting leukemogenesis by inhibiting phagocytosis of the leukemic cells by macrophages.

CD47 is significantly upregulated in leukemic $Fas^{lpr/lpr} \times$ hMRP8bcl2 transgenic bone marrow, and in leukemic hMRP8bcr/abl×hMRP8bcl2 mice. Transcripts for CD47 are increased in leukemic hMRP8bcr/abl×hMRP8bcl2 bone marrow 3-4 fold by quantitative RT-PCR and 6-7 fold in c-Kit enriched leukemic marrow relative to healthy hMRP8bcl2+ bone marrow (FIG. 11e). Leukemic spleen had an expansion of the granulocyte macrophage progenitor (GMP) population as well as c-Kit+Sca-1+Lin-stem and progenitor subsets relative to control mice, which were of the same genotype as leukemic mice but failed to develop disease (FIG. 11a-d). Expression levels for CD47 protein were found to begin increasing in leukemic mice relative to control mice at the stage of the Flk2– CD34– c-Kit+Sca-1+Lin– long-term hematopoietic stem cell (LT-HSC) (FIG. 11f). This increased level of expression was maintained in GMP and Mac-1+ blasts, but not megakaryocyte/erythroid restricted progenitors (MEP) (FIG. 11f). The increase in CD47 between leukemic and normal cells was between 3 to 20 fold. All mice that developed leukaemia that we have examined from hMRP8bcr/abl×hMRP8bcl2 primary (n=3) and secondary transplanted mice (n=3), $Fas^{lpr/lpr} \times$ hMRP8bcl2 primary (n=14) and secondary (n=19) mice, and hMRP8bcl2×hMRP8bcl2 primary (n=3) and secondary (n=12) mice had increased CD47 expression. We have also found increased CD47 expression in mice that received p210bcr/abl retrovirally-transduced mouse bone marrow cells that developed leukemia.

FACS-mediated analysis of human hematopoietic progenitor populations was performed on blood and marrow derived from normal cord blood and mobilized peripheral blood (n=16) and myeloproliferative disorders (MPDs) including polycythemia vera (PV; n=16), myelofibrosis (MF; n=5), essential thrombocythemia (ET; n=7), chronic myelomonocytic leukaemia (CMML; n=11) and atypical chronic myeloid leukaemia (aCML; n=1) as well as blast crisis phase chronic myeloid leukaemia (CML; n=19), chronic phase CML (n=7) and acute myelogenous leukaemia (AML; n=13). This analysis demonstrated that granulocyte-macrophage progenitors (GMP) expanded in MPDs with myeloid skewed differentiation potential including atypical CML, proliferative phase CMML and acute leukaemia including blast crisis CML and AML (FIG. 12a). AML HSC and progenitors uniformly exhibited higher levels of CD47 expression compared with normal controls (FIG. 12b); every sample from BC-CML and AML had elevated levels of CD47. Moreover, progression from chronic phase CML to blast crisis was associated with a significant increase in CD47 expression (FIG. 12c). Using the methods described in this study, we have found that human CD47 protein expression in CML-BC increased 2.2 fold in CD90+ CD34+ CD38– Lin– cells relative to normal ($p=6.3\times10^{-5}$), 2.3 fold in CD90– CD34+ CD38– Lin– cells relative to normal ($p=4.3\times10^{-5}$), and 2.4 fold in CD 34+ CD38+ Lin–cells ($p=7.6\times10^{-6}$) (FIGS. 12b-12c); however, using a newer optimized staining protocol we have observed that CD47 is increased approximately 10 fold in AML and BC-CML compared to normal human HSCs and progenitors.

Figure 13A:
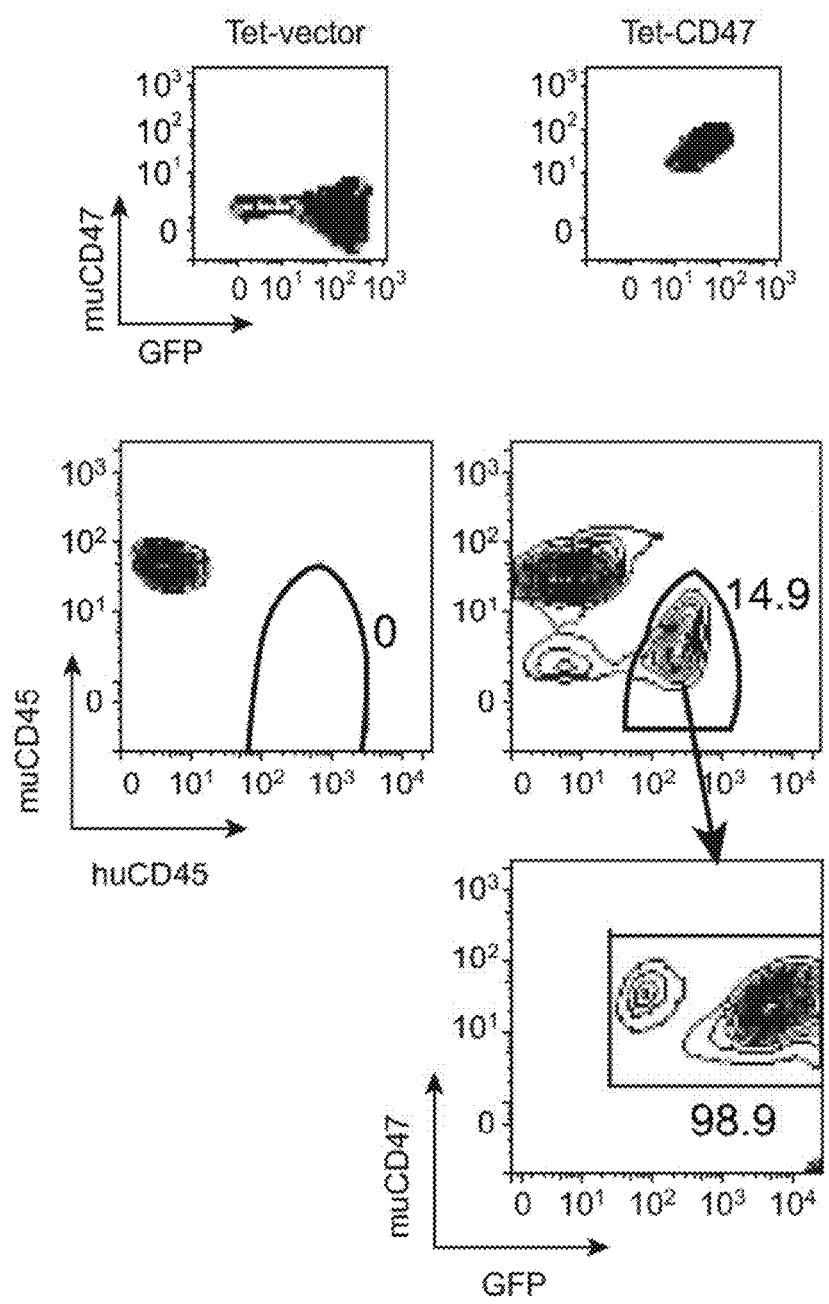
Figure 13B:
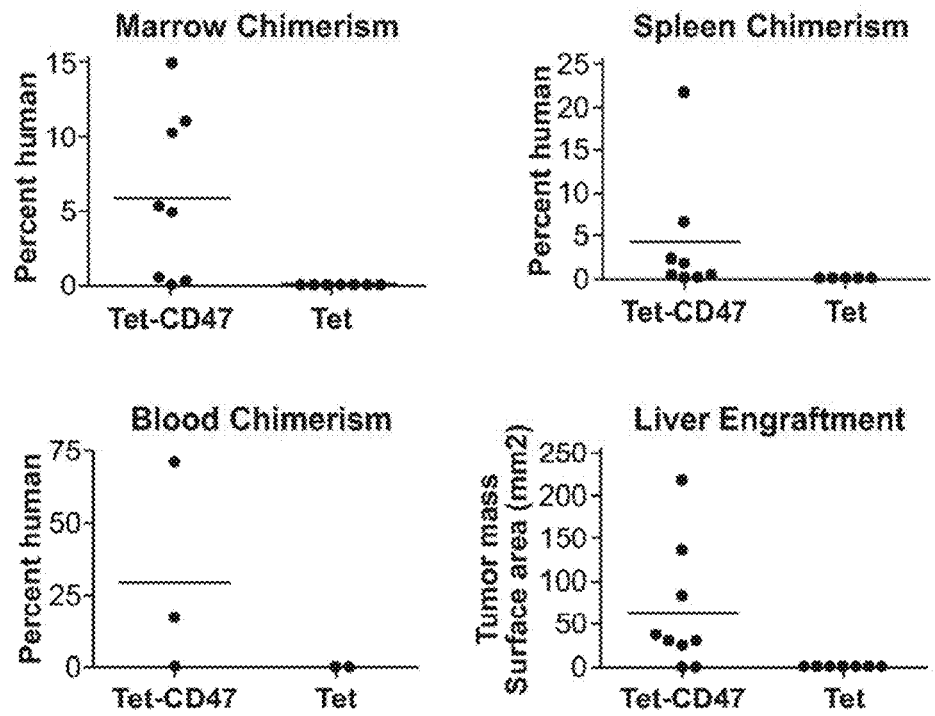
Figure 13C:
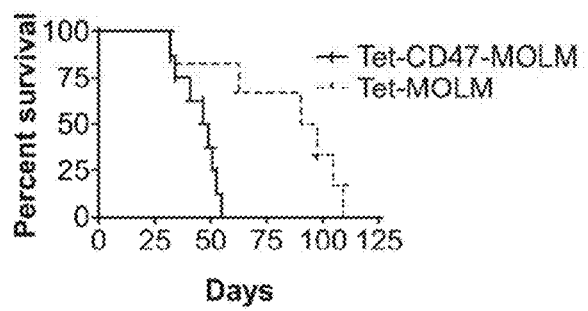
Figure 13D:
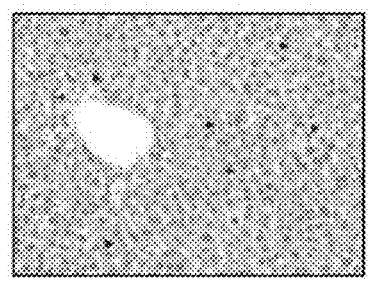

It was then asked whether forced expression of mouse CD47 on human leukemic cells would confer a competitive advantage in forming tumors in mice. MOLM-13 cells, which are derived from a patient with AML 5a, were transduced with Tet-MCS-IRES-GFP (Tet) or Tet-CD47-MCS-IRES-GFP (Tet-CD47) (FIG. 13a), and stable integrants were propagated on the basis of GFP expression. The cells were then transplanted intravenously in a competitive setting with untransduced MOLM-13 cells into T, B, and NK deficient recombination activating gene 2, common gamma chain deficient (RAG2-/-, Gc-/-) mice. Only cells transduced with Tet-CD47 were able to give rise to tumors in these mice, efficiently engrafting bone marrow, spleen and peripheral blood (FIGS. 13a-b). The tumors were also characterized by large tumor burden in the liver (FIGS. 13b, 13g), which is particularly significant because the liver is thought to have the highest number of macrophages of any organ, with estimates that Kupffer cells may comprise 80% of the total tissue macrophage population. These cells also make up 30% of the sinusoidal lining, thereby strategically placing them at sites of entry into the liver. Hence, significant engraftment there would have to disable a macrophage cytotoxic response. In addition to developing tumor nodules, the Tet-CD47 MOLM-13 cells exhibited patterns of hepatic involvement typically seen with human AML, with leukemic cells infiltrating the liver with a sinusoidal and perivenous pattern. (FIG. 13d). Overall, Tet-CD47 MOLM-13 transplanted mice died more quickly than Tet MOLM-13 transplanted mice, which had virtually no engraftment of leukemic cells in hematopoietic tissues (FIG. 13c). Tet-MOLM-13 mice still had significant mortality, most likely due to localized growth at the site of injection (retro-orbital sinus) with extension into the brain.

Figure 13E:
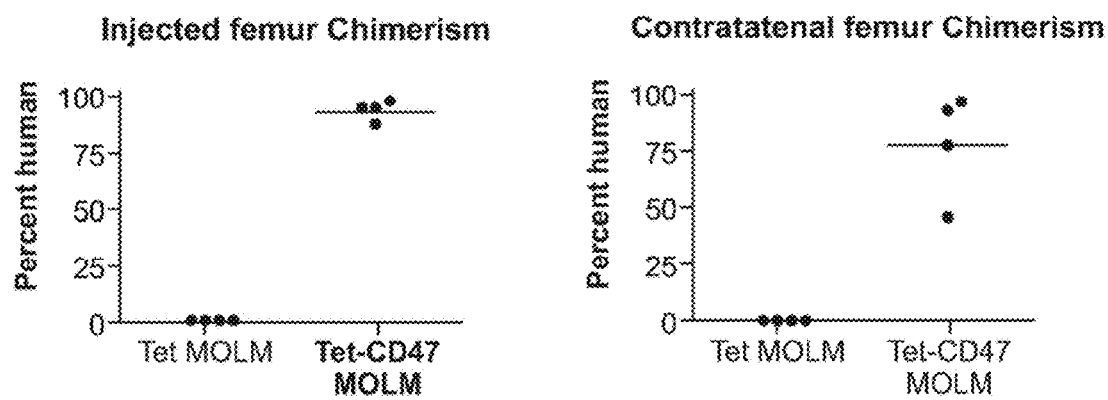
Figure 13F:
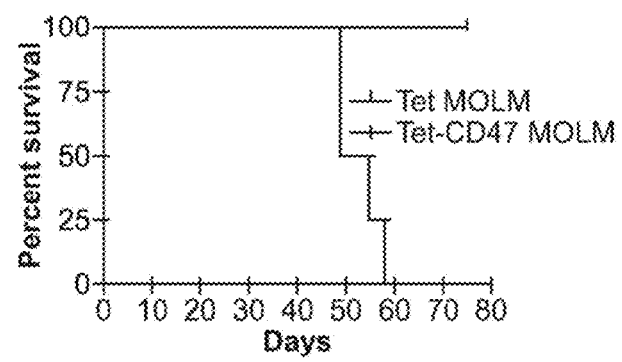
Figure 13G:

Since CD47 has been shown to be important for the migration of hematopoietic cells, and is known to modulate binding to extracellular matrix proteins, either by direct interaction or via its effect on integrins, one possibility for the lack of growth of Tet MOLM-13 cells in mice was their inability to migrate to niches. To test this possibility, Tet MOLM-13 or Tet-CD47 MOLM-13 cells were directly injected into the femoral cavity of immunodeficient mice. Tet-CD47 MOLM-13 cells were able to engraft all bones and other hematopoietic tissues of recipient mice, whereas Tet MOLM-13 cells had minimal, if any, engraftment only at the site of injection (FIG. 13e). Mice transplanted in this manner with Tet-CD47 MOLM-13 cells died at approximately 50-60 days post-transplant (n=4), whereas mice that received Tet MOLM-13 (n=5) cells remained alive for at least 75 days without signs of disease at which point they were euthanized for analysis. These results suggest a function other than or in addition to migration or homing for CD47 in MOLM-13 engraftment.

Figure 14B:
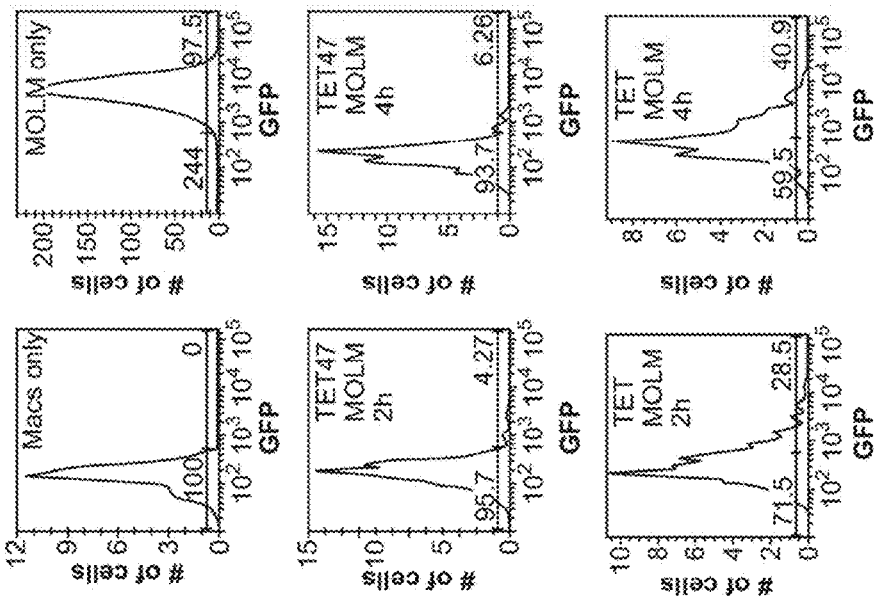
Figure 14A:
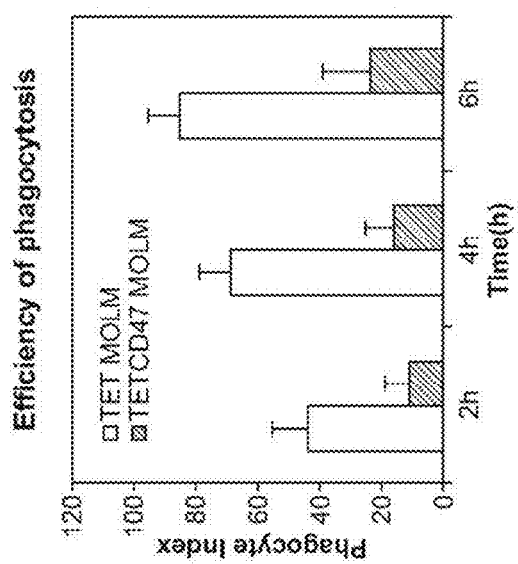
Figure 14C:
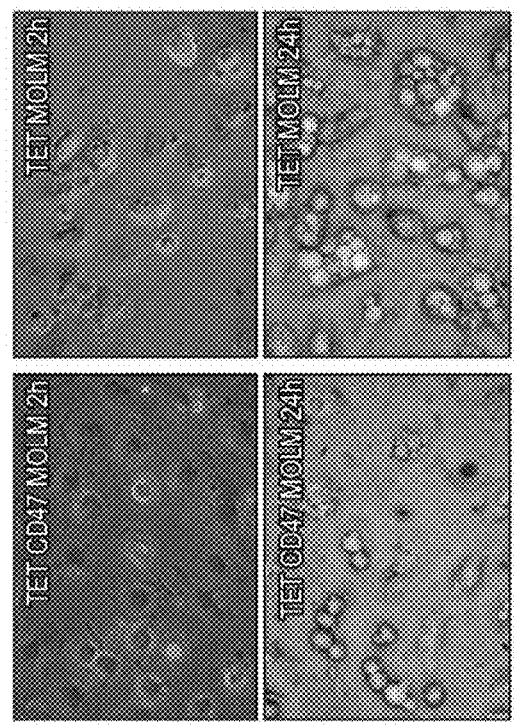

Complete lack of CD47 has been shown to result in phagocytosis of transplanted murine erythrocytes and leukocytes, via lack of interaction with SIRPα on macrophages. Thus, we tested whether over-expression of CD47 could prevent phagocytosis of live, unopsonized MOLM-13 cells. We incubated Tet or Tet-CD47 MOLM-13 cells with bone marrow derived macrophages (BMDM) for 2-24 hours and assessed phagocytosis by counting the number of ingested GFP+ cells under a microscope or by evaluating the frequency of GFP+ macrophages using a flow cytometer. Expression of CD47 dramatically lowered macrophage clearance of these cells at all time points tested, whereas Tet-MOLM-13 were quickly phagocytosed in a manner that increased over time (FIGS. 14a-c). We also injected MOLM-13 cells into mice and analyzed hematopoietic organs 2 hours later for evidence of macrophage phagocytosis. Macrophages in bone marrow, spleen, and liver all had higher GFP+ fraction when injected with Tet MOLM-13 cells as compared to CD47 expressing cells. This indicates that CD47 over-expression can compensate for pro-phagocytic signals already present on leukemic cells, allowing them to survive when they would otherwise be cleared by macrophages.

Recent report indicates that lack of CD47 reactivity across species might mediate xenorejections of transplanted cells. Furthermore, a recent study has demonstrated that human CD47 is unable to interact with SIRPα from C57Bl/6 mice, but is able to react with receptor from non-obese diabetic (NOD) mice, which are more permissive for human cell engraftment than C57Bl/6 mice. Furthermore, we have also observed that HL-60 cells, a human promyelocytic cell line with higher levels of human CD47 expression than MOLM-13, are able to engraft mice and cause leukaemia. Jurkat cells, a human T-lymphocyte cell line, are very high for human CD47 and are phagocytosed by murine macrophages in vitro at a much lower rate than MOLM-13. Thus, our data indicate that the ability of cells to engraft mice in vivo or evade phagocytosis in vitro by mouse macrophages correlates with the level of human CD47 expression.

Figure 15A:
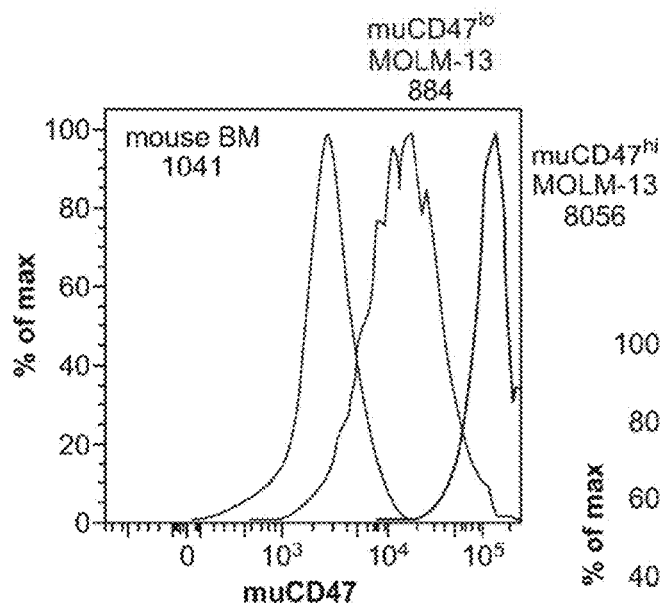
Figure 15B:
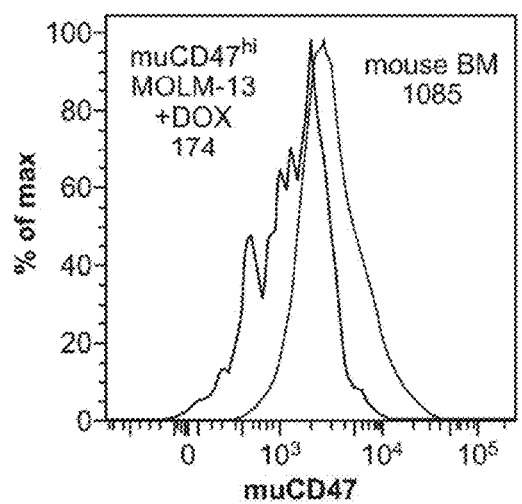
Figure 15C:
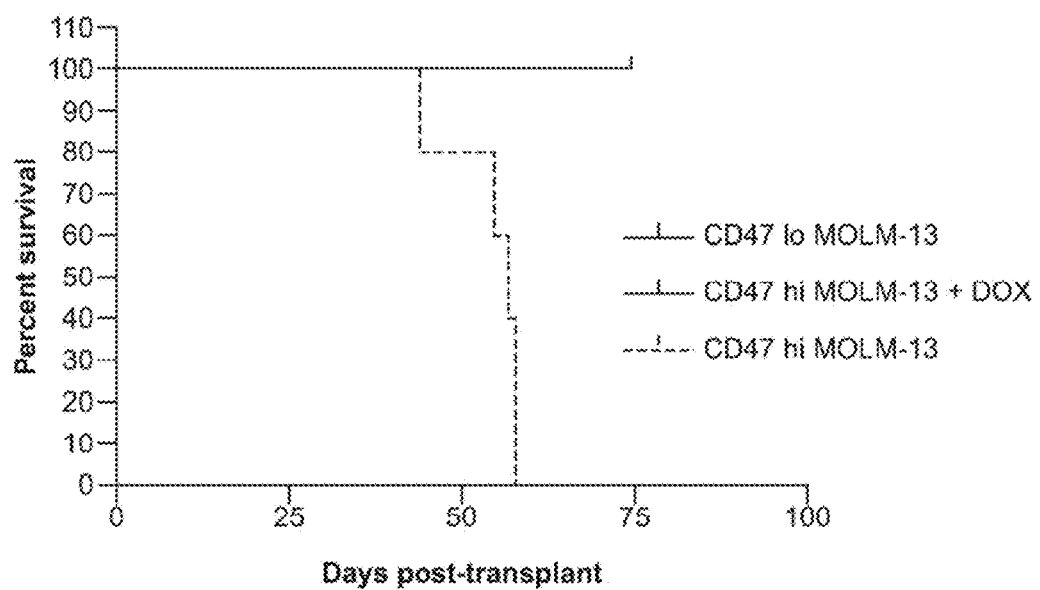

To model the tumorigenic effect of having high versus low CD47 expression, we sorted clones of murine CD47 expressing MOLM-13 cells into high and low expressers. When adjusted for cell size, CD47 density on the CD47$^{lo}$ MOLM-13 cells was approximately equal to mouse bone marrow cells, whereas CD47$^{hi}$ MOLM-13 cells had approximately 9 fold higher expression, an increase commensurate with the change seen in CD47 expression on primary leukemic cells compared to their normal counterparts (FIG. 15a). When high or low expressing cells were transplanted into recipients, only mice transplanted with high expressing cells succumbed to disease by 75 days of age (FIG. 15c). Furthermore, organomegaly was more pronounced in mice transplanted with high expressing cells (FIG. 15d). Mice receiving CD47$^{lo}$ MOLM-13 cells still had notable liver masses. However, the masses were invariably 1-2 large nodes that were well-encapsulated and physically segregated from the liver parenchyma, in marked contrast to tumor masses from CD47hi MOLM-13 cells which consisted of hundreds of small masses scattered throughout the parenchyma. Thus, these large tumor masses consist of cells which have found macrophage free-niches to grow in separate from the main organ body. As expected, the infiltration of MOLM-13 cells in bone marrow and spleen of recipient mice was much higher for mice transplanted with CD47$^{hi}$ MOLM-13 cells as well (FIG. 15e). We also examined the level of CD47 expression in two mice that received CD47$^{lo}$ MOLM-13 cells but had significant marrow engraftment. In both cases, the persisting cells after 75 days had much higher levels of CD47 than the original line (FIG. 15f), indicating that a strong selection pressure exists in vivo for high levels of CD47 expression on leukemic cells. In total, these data indicate that CD47 expression level is a significant factor in tumorigenic potential, and that in a heterogeneous population of leukemic cells, strong selection exists for those clones with high CD47 expression.

Figure 15G:
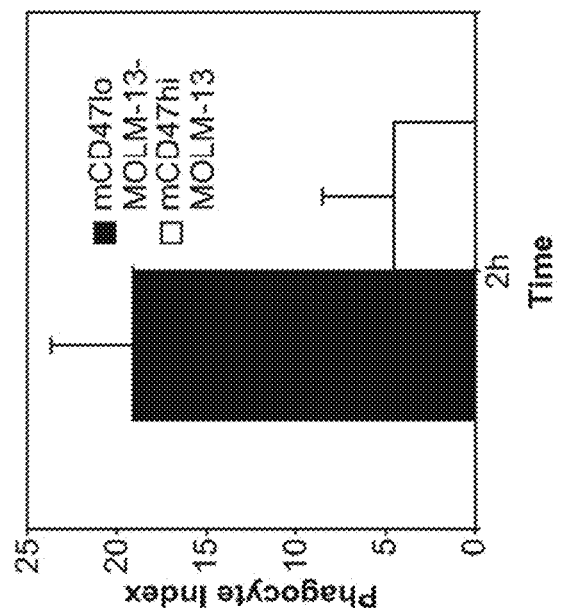
Figure 15F:
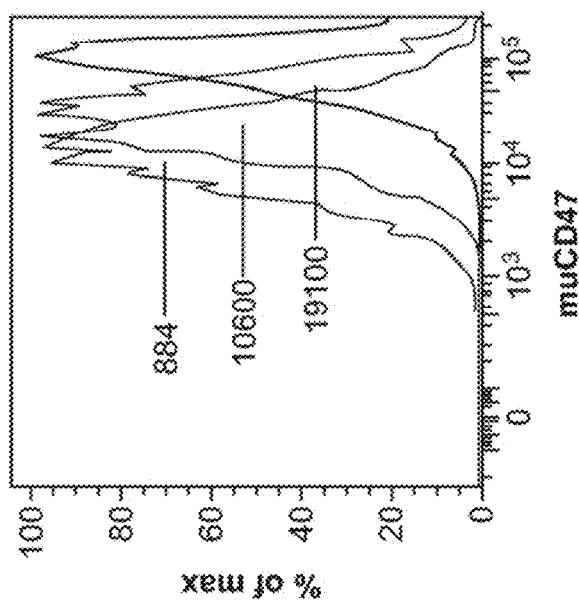
Figure 15H:
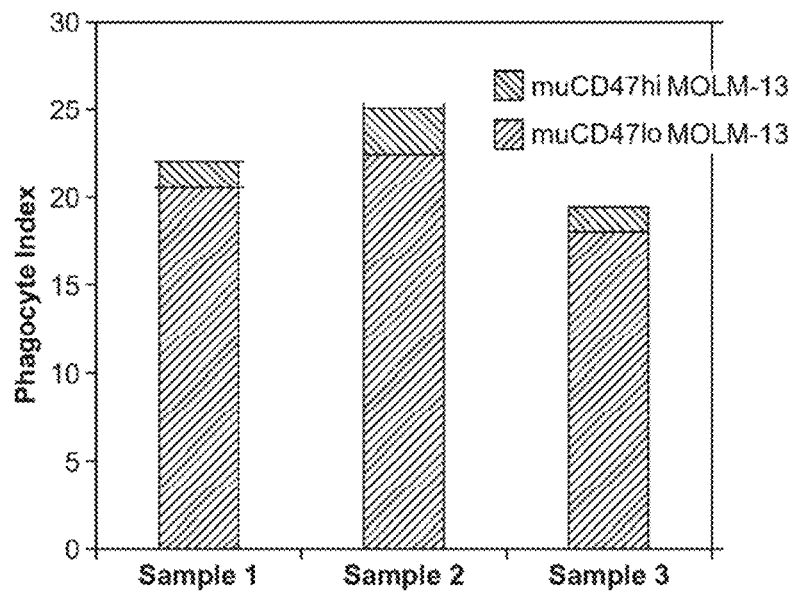
Figure 15I:
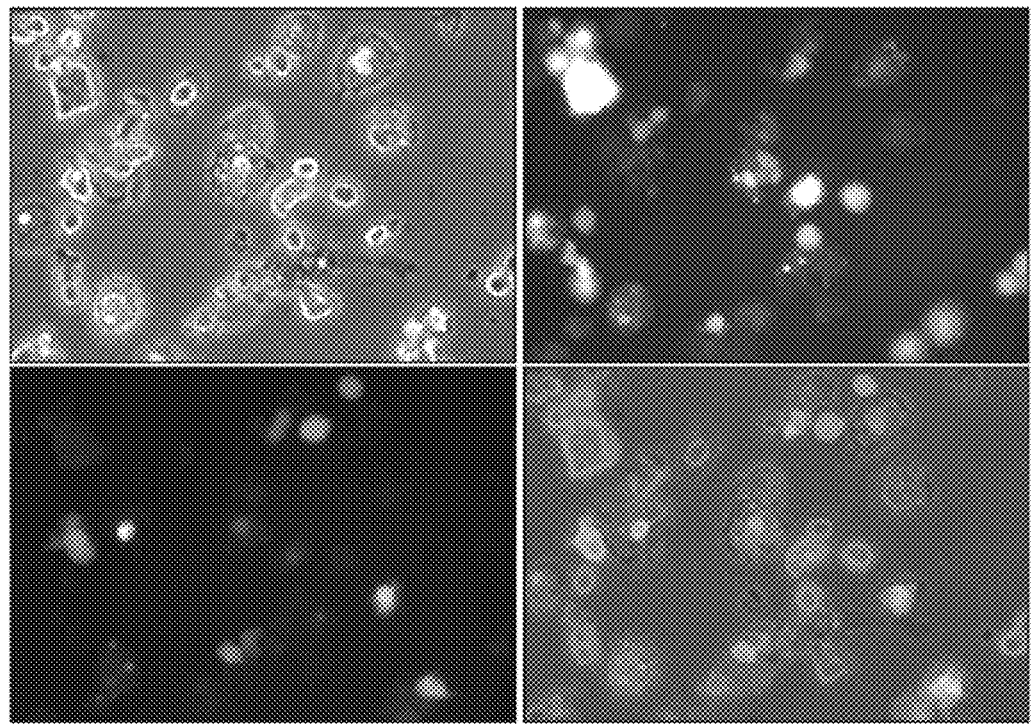

We then asked if higher CD47 expression level would provide added protection against macrophage phagocytosis. We performed an in vitro phagocytosis assay with CD47$^{hi}$ and CD47$^{lo}$ MOLM-13 red fluorescent protein (RFP) expressing cells. After incubation with macrophages, far greater numbers of CD47$^{lo}$ cells were phagocytosed as compared to CD47$^{hi}$ cells (FIG. 15g). If phagocytic indices are compared for control MOLM-13 cells, bulk (un-sorted) CD47 MOLM-13 cells, CD47$^{lo}$, and CD47$^{hi}$ MOLM-13 cells, then a direct correlation between CD47 expression level and ability to evade phagocytosis can be seen (FIG. 14a, FIG. 15f). Furthermore, when CD47$^{lo}$ RFP MOLM-13 cells and CD47$^{hi}$ GFP MOLM-13 cells were co-incubated with macrophages in the same wells, the low expressing cells were far more likely to be phagocytosed (FIG. 15h, 15i). Thus, in a mixed population of cells with varying levels of CD47 expression, the low expressing cells are more likely to be cleared by phagocytic clearance over time.

We also titrated CD47 expression using another method. Since CD47 is expressed in MOLM-13 cells using a Tet-OFF system, we utilized the Tet-inducible promoter element to control expression of CD47 in MOLM-13 cells. Beginning two weeks after transplantation with CD47$^{hi}$ MOLM-13 cells, a cohort of mice was given doxycycline and followed for up to 75 days post-transplant. During this time course, none of the mice given doxycycline succumbed to disease or had large infiltration of MOLM-13 cells in hematopoietic organs (FIGS. 15b-d). At the doses of doxycycline used in this experiment, muCD47 expression in MOLM-13 cells was reduced to levels below that of normal mouse bone marrow, but notably not completely absent (FIG. 15b). Thus, a sustained high level of CD47 expression is required for robust MOLM-13 survival in hematopoietic organs.

Many examples of tumor clearance by T, B, and NK cells have been described in the literature, indicating that a healthy immune system is essential for regulating nascent tumor growth. However, to date, few examples have been produced indicating that macrophage-mediated phagocytosis can check tumor development. Collectively, our studies reveal that ectopic expression of CD47 can enable otherwise immunogenic tumor cells to grow rapidly in a T, B, and NK-cell deficient host. Furthermore, this is likely to reflect a mechanism used by human myeloid leukemias to evade the host immune system since CD47 is consistently upregulated in murine and human myeloid leukemias, including all forms of chronic and acute myeloid leukaemia tested thus far. Thus, it appears likely that tumor cells are capable of being recognized as a target by activated macrophages and cleared through phagocytosis. By upregulating CD47, cancers are able to escape this form of innate immune tumor surveillance.

This form of immune evasion is particularly important since these cancers often occupy sites of high macrophage infiltration. CD47 was first cloned as an ovarian tumor cell marker, indicating that it may play a role in preventing phagocytosis of other tissue cancers as well. Furthermore, solid tumors often metastasize to macrophage rich tissues such as liver, lung, bone marrow, and lymph nodes, indicating that they must be able to escape macrophage-mediated killing in those tissues. Finding methods to disrupt CD47-SIRPα interaction may thus prove broadly useful in developing novel therapies for cancer. Preventing CD47-SIRPα interaction is doubly effective since antigens from phagocytosed tumor cells may be presented by macrophages to activate an adaptive immune response, leading to further tumor destruction. Methods Mice. hMRP8bcrabl, hMRP8bcl2, and Fas$^{lpr/lpr}$ transgenic mice were created as previously described and crossed to obtain double transgenics. hMRP8bcl2 homozygotes were obtained by crossing heterozygote mice to each other. C57Bl/6 Ka mice from our colony were used as a source of wild-type cells. For transplant experiments, cells were transplanted into C57Bl/6 RAG2$^{-/-}$ common gamma chain (Gc)$^{-/-}$ mice given a radiation dose of 4 Gy using gamma rays from a cesium irradiator (Phillips). Primary mouse leukemias were transplanted into CD45.2 C57Bl6/Ka mice given a radiation dose of 9.5 Gy. Mice were euthanized when moribund.

Mouse tissues. Long bones were flushed with PBS supplemented with 2% fetal calf serum staining media (SM) Spleens and livers were dissociated using frosted glass slides in SM, then passed through a nylon mesh. All samples were treated with ACK lysis buffer to lyse erythrocytes prior to further analysis.

Quantitative RT-PCR Analysis. Bone marrow was obtained from leukemic hMRP8bcr/abl×hMRP8bcl2 mice or hMRP8bcl2 control mice. Cells were c-Kit enriched using c-Kit microbeads and an autoMACS column (Miltenyi). RNA was extracted using Trizol reagent (Invitrogen) and reverse transcription performed using SuperScriptII reverse polymerase (Invitrogen). cDNA corresponding to approximately 1000 cells was used per PCR reaction. Quantitative PCR was performed with a SYBR green kit on an ABI Prism 7000 PCR (Applied Biosystems) machine at 50° C. for 2 minutes, followed by 95° C. for 10 minutes and then 40 cycles of 95° C. for 15 minutes followed by 60° C. for 1 minute. Beta-actin and 18S RNA were used as controls for cDNA quantity and results of CD47 expression were normalized. Sequences for 18S RNA forward and reverse primers were TTGACGGAAGGGCACCACCAG and GCACCACCACCCACGGAATCG, respectively, for beta-actin were TTCCTTCTTGGGTATGGAAT and GAGCAATGATCTTGATCCTC, and for CD47 were AGGCCAAGTCCAGAAGCATTC and AATCATTCTGCTGCTCGTTGC.

Human Bone Marrow and Peripheral Blood Samples. Normal bone marrow samples were obtained with informed consent from 20-25 year old paid donors who were hepatitis A, B, C and HIV negative by serology (All Cells). Blood and marrow cells were donated by patients with chronic myelomonocytic leukemia (CMML), chronic myeloid leukemia (CML), and acute myelogenous leukemia (AML) and were obtained with informed consent, from previously untreated patients.

Cell lines. MOLM-13 cells were obtained from DSMZ. HL-60 and Jurkat cells were obtained from ATCC. Cells were maintained in Iscove's modified Dulbecco's media (IMDM) plus 10% fetal bovine serum (FBS) (Hyclone). To fractionate MOLM-13 cells into those with high and low CD47 expression, Tet-CD47 MOLM-13 cells were stained with anti-mouse CD47 Alexa-680 antibody (mIAP301). The highest and lowest 5% of mouse CD47 expressing cells was sorted on a BD FACSAria and re-grown in IMDM+10% FCS for 2 weeks. The cells were sorted for three more rounds of selection following the same protocol to obtain the high and low expressing cells used in this study. To obtain red fluorescent protein (RFP) constructs, the mCherry RFP DNA was cloned into Lentilox 3.7 (pLL3.7) empty vector. Lentivirus obtained from this construct was then used to infect cell lines.

Cell staining and flow cytometry. Staining for mouse stem and progenitor cells was performed using the following monoclonal antibodies: Mac-1, Gr-1, CD3, CD4, CD8, B220, and Ter119 conjugated to Cy5-PE (eBioscience) were used in the lineage cocktail, c-Kit PE-Cy7 (eBioscience), Sca-1 Alexa680 (e13-161-7, produced in our lab), CD34 FITC(eBioscience), CD16/32(FcGRII/III) APC (Pharmingen), and CD135(Flk-2) PE (eBioscience) were used as previously described to stain mouse stem and progenitor subsets. Mouse CD47 antibody (clone mIAP301) was assessed using biotinylated antibody produced in our lab. Cells were then stained with streptavidin conjugated Quantum Dot 605 (Chemicon). Samples were analyzed using a FACSAria (Beckton Dickinson).

For human samples, mononuclear fractions were extracted following Ficoll density centrifugation according to standard methods and analyzed fresh or subsequent to rapid thawing of samples previously frozen in 90% FCS and 10% DMSO in liquid nitrogen. In some cases, CD34+ cells were enriched from mononuclear fractions with the aid of immunomagnetic beads (CD34+ Progenitor Isolation Kit, Miltenyi Biotec, Bergisch-Gladbach, Germany). Prior to FACS analysis and sorting, myeloid progenitors were stained with lineage marker specific phycoerythrin (PE)-Cy5-conjugated antibodies including CD2 RPA-2.10; CD11b, ICRF44; CD20, 2H7; CD56, B159; GPA, GA-R2 (Becton Dickinson-PharMingen, San Diego), CD3,S4.1; CD4, S3.5; CD7, CD7-6B7; CD8, 3B5; CD10, 5-1B4, CD14, TUK4; CD19, SJ25-C1 (Caltag, South San Francisco, Calif.) and APC-conjugated anti-CD34, HPCA-2 (Becton Dickinson-PharMingen), biotinylated anti-CD38, HIT2 (Caltag) in addition to PE-conjugated anti-IL-3Rα, 9F5 (Becton Dickinson-ParMingen) and FITC-conjugated anti-CD45RA, MEM56 (Caltag) followed by staining with Streptavidin—Texas Red to visualize CD38-BIO stained cells.

Following staining, cells were analyzed using a modified FACS Vantage (Becton Dickinson Immunocytometry Systems, Mountain View, Calif.) equipped with a 599 nm dye laser and a 488 nm argon laser or a FACSAria. Hematopoietic stem cells (HSC) were identified as CD34+ CD38+ CD90+ and lineage negative. Anti-human CD47 FITC (clone B6H12, Pharmingen) was used to assess CD47 expression in all human samples. Fold change for CD47 expression was determined by dividing the average mean fluorescence intensity of CD47 for all the samples of CML-BC, CML-CP, or AML by the average mean fluorescence intensity of normal cells for a given cell population. Common myeloid progenitors (CMP) were identified based on CD34+ CD38+ IL-3Rα+ CD45RA− lin− staining and their progeny including granulocyte/macrophage progenitors (GMP) were CD34+CD38+IL-3Rα+ CD45RA+ Lin− while megakaryocyte/erythrocyte progenitors (MEP) were identified based on CD34+ CD38+ IL-3Rα− CD45RA− Lin− staining.

To determine the density of mouse or human CD47, cells were stained with saturating amounts of anti-CD47 antibody and analyzed on a FACSAria. Since forward scatter is directly proportional to cell diameter, and density is equal to expression level per unit of surface area we used FloJo software to calculate geometric mean fluorescent intensity of the CD47 channel and divided by the geometric mean of the forward scatter value squared ($FSC^2$) to obtain an approximation for density of CD47 expression on the membrane.

Engraftment of MOLM-13 cells was assessed by using anti-human CD45 PE-Cy7 (Pharmingen), anti-mouse CD45.2 APC (clone AL1-4A2), and anti-mouse CD47 Alexa-680 (mIAP301). All samples were resuspended in propidium iodide containing buffer before analysis to exclude dead cells. FACS data was analyzed using FloJo software (Treestar).

Lentiviral preparation and transduction. pRRL. sin-18. PPT.Tet07.IRES.GFP.pre, CMV, VSV, and tet trans-activator (tTA) plasmids were obtained from Luigi Naldini. The full length murine cDNA for CD47 form 2 was provided by Eric Brown (UCSF). The CD47 cDNA construct was ligated into the BamHI/Nhel site of Tet-MCS-IRES-GFP. Plasmid DNA was transfected into 293T cells using standard protocols. The supernatant was harvested and concentrated using a Beckman LM-8 centrifuge (Beckman). Cells were transduced with Tet or Tet-CD47-MCS-IRES-GFP and tTA *lentivirus* for 48 hours. GFP+ cells were sorted to purity and grown for several generations to ensure stability of the transgenes.

Injections. Cells were injected intravenously into the retro-orbital sinuses of recipient mice or via the tail vein as noted. For intra-femoral injections, cells were injected into the femoral cavity of anesthetized mice in a volume of 20 μl using a 27-gauge needle. An isofluorane gas chamber was used to anesthetize mice when necessary.

MOLM-13 cell engraftment. Animals were euthanized when moribund and bone marrow, spleen, and liver harvested. Peripheral blood was obtained by tail bleed of the animals 1 hour prior to euthanization. Engraftment of MOLM-13 cells in marrow, spleen, and peripheral blood was determined as described above. Tumor burden in the liver was determined by calculating the area of each visible tumor nodule using the formula ((length in mm+width in mm)/2)*π. Area of each nodule was then added together per liver.

Doxycycline administration. Doxycycline hydrochloride (Sigma) was added to drinking water at a final concentration of 1 mg/mL. Drinking water was replaced every 4 days and protected from light. In addition, mice received a 10 μg bolus of doxycycline by i.p. injection once a week.

Bone marrow derived macrophages (BMDM). Femurs and tibias were harvested from 057B1/6 Ka mice and the marrow was flushed and placed into a sterile suspension of PBS. The bone marrow suspension was grown in IMDM plus 10% FBS with 10 ng/mL of recombinant murine macrophage colony stimulating factor (MCSF, Peprotech) for 7-10 days.

In vitro phagocytosis assays. BMDM were harvested by incubation in trypsin/EDTA (Gibco) for 5 minutes and gentle scraping. Macrophages were plated at $5 \times 10^4$ cells per well in a 24-well tissue culture plate (Falcon). After 24 hours, media was replaced with serum-free IMDM. After an additional 2 hours, $2.5 \times 10^5$ Tet or Tet-CD47 MOLM-13 cells were added to the macrophage containing wells and incubated at 37 C° for the indicated times. After co-incubation, wells were washed thoroughly with IMDM 3 times and examined under an Eclipse T5100 (Nikon) using an enhanced green fluorescent protein (GFP) or Texas Red filter set (Nikon). The number of GFP+ or RFP+ cells within macrophages was counted and phagocytic index was calculated using the formula: phagocytic index=number of ingested cells/(number of macrophages/100). At least 200 macrophages were counted per well. For flow cytometry analysis of phagocytosis macrophages were harvested after incubation with MOLM-13 cells using trypsin/EDTA and gentle scraping. Cells were stained with anti-Mac-1 PE antibody and analyzed on a BD FACSAria. Fluorescent and brightfield images were taken separately using an Eclipse T5100 (Nikon), a super high pressure mercury lamp (Nikon), an endow green fluorescent protein (eGFP) bandpass filter (Nikon) a Texas Red bandpass filter (Nikon), and a RT Slider (Spot Diagnostics) camera. Images were merged with Photoshop software (Adobe).

For in vivo assays, marrow from leg long bones, spleen, and liver were harvested 2 hours after injecting target cells into $RAG2^{-/-}, Gc^{-/-}$ mice. They were prepared into single cell suspensions in PBS plus 2% FCS. Cells were labeled with anti-human CD45 Cy7-PE and anti-mouse F4/80 biotin (eBiosciences). Secondary stain was performed with Streptavidin-APC (eBiosciences). Cells that were human CD45−, F4/80+ were considered to be macrophages, and GFP+ cells in this fraction was assessed.

Example 3

Hematopoietic Stem and Progenitor Cells Upregulate CD47 to Facilitate Mobilization and Homing to Hematopoietic Tissues We show here that hematopoietic stem cells (HSCs) from CD47 deficient ($IAP^{-/-}$) mice fail to engraft wild-type recipients. As expected, these cells are rapidly cleared by host macrophages, whereas $IAP^{+/+}$ HSCs are not. When stem and progenitor cells are forced to divide and enter circulation using cyclophosphamide/G-CSF or lipopolysaccharide, CD47 is rapidly up-regulated on these cells. We propose that higher levels of CD47 in stem cells during stress hematopoiesis and mobilization provides added protection against phagocytosis by activated macrophages of the reticuloendothelial system. In support of this hypothesis, we show that $IAP^{+/-}$ cells transplanted into wild-type recipients lose engraftment over time, whereas wild-type donor cells do not. We conclude that phagocytosis is a significant physiological mechanism that clears hematopoietic progenitors over time, and that CD47 over-expression is required to prevent phagocytic clearance.

HSCs have the ability to migrate to ectopic niches in fetal and adult life via the blood stream. Furthermore, HSCs can be prodded into the circulation using a combination of cytotoxic agents and cytokines that first expand HSC numbers in situ. Once in the blood stream, HSCs must navigate the vascular beds of the spleen and liver. Macrophages at these sites function to remove damaged cells and foreign particles from the blood stream. Furthermore, during inflammatory states, macrophages become more phagocytically active. Hence, additional protection against phagocytosis might be required for newly arriving stem cells at these sites.

We determined if CD47 expression on bone marrow stem and progenitor cells had a role in regulation of normal hematopoiesis. CD47 expression has been shown to be essential for preventing phagocytosis of red blood cells, T-cells, and whole bone marrow cells in a transplant setting. Thus, we asked if lack of CD47 would prevent HSCs from engrafting after being delivered intravenously. To test this, we employed the CD47 knockout mouse ($IAP^{-/-}$). These mice develop normally and do not display any gross abnormalities. They do, however, die very quickly after intraperitoneal bacterial challenge because neutrophils fail to migrate to the gut quickly. In addition, cells from these mice fail to transplant into wild-type recipients, but they will engraft in IAP−/− recipients.

Figure 18A:
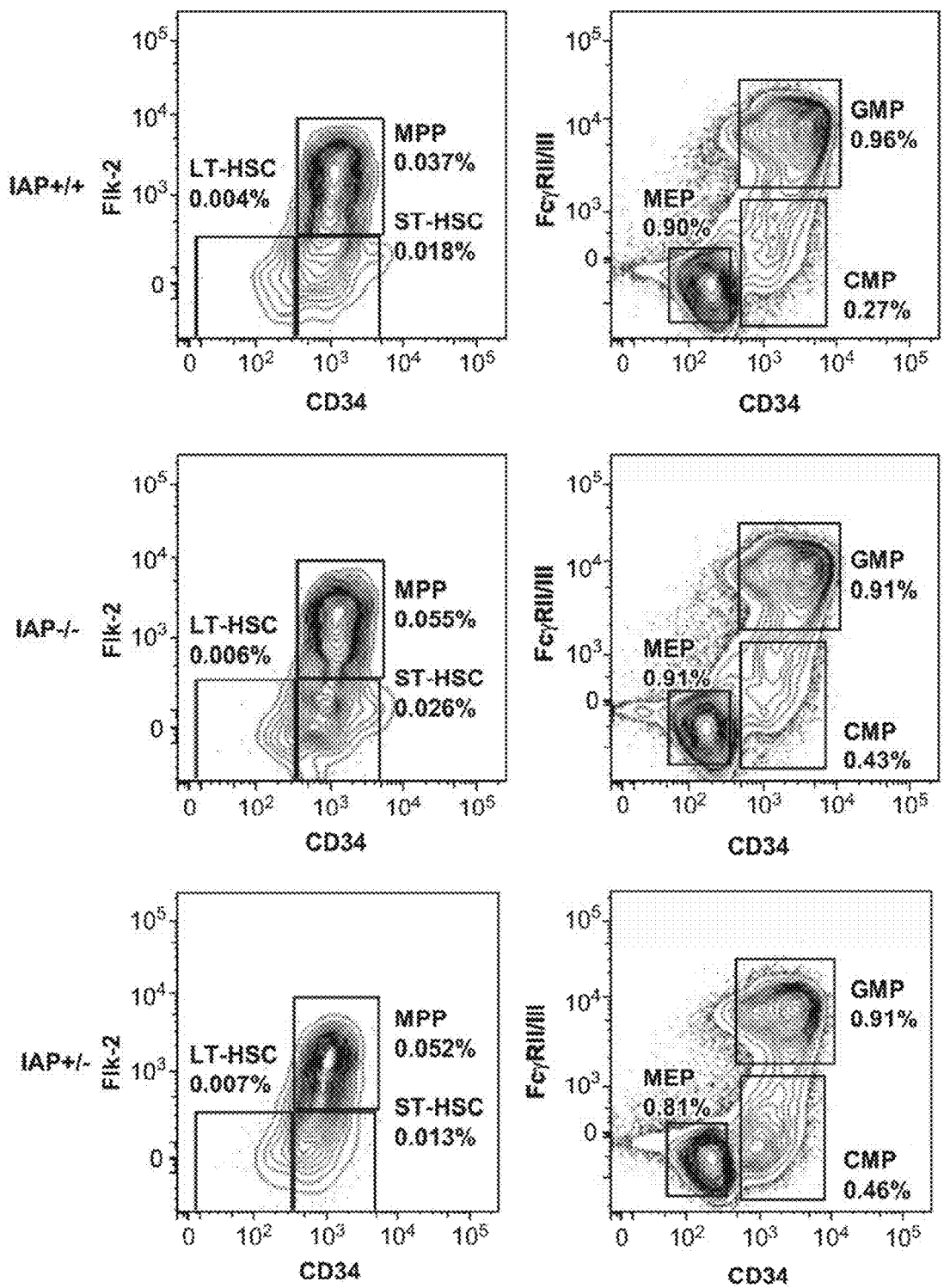
Figure 18B:
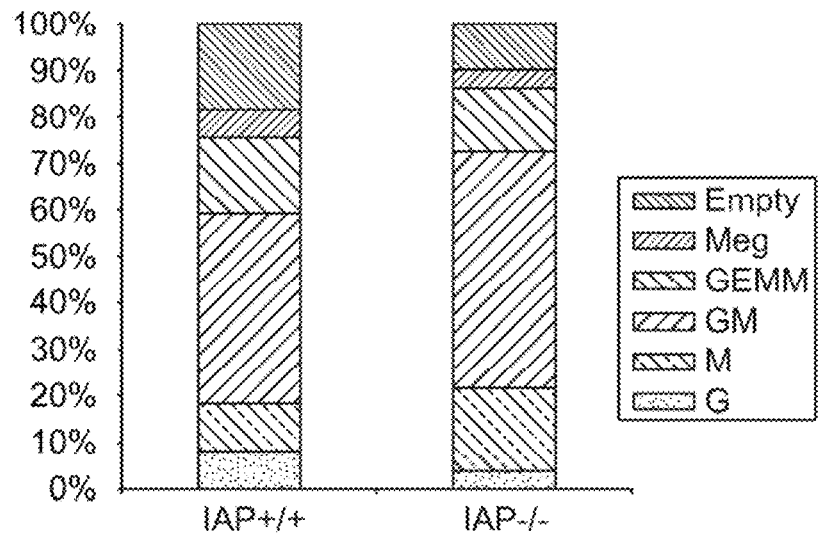

We first examined stem and progenitor frequencies in $IAP^{+/-}$ and $IAP^{-/-}$ mice. When examining for cells in the stem and myeloid progenitor compartment, there was no difference between these mice and wild-type mice (FIG. 18a). We then tested stem cells from these mice for their ability to form colonies in an in vitro assay. We sorted highly purified Flk2− CD34− KLS stem cells from these mice and plated them onto methylcellulose in the presence of a standard cytokine cocktail. We examined colony formation at day 7 and found that there was no major difference between wild-type and IAP−/− stem cells in the number and type of colonies formed (FIG. 18b).

Figure 18C:
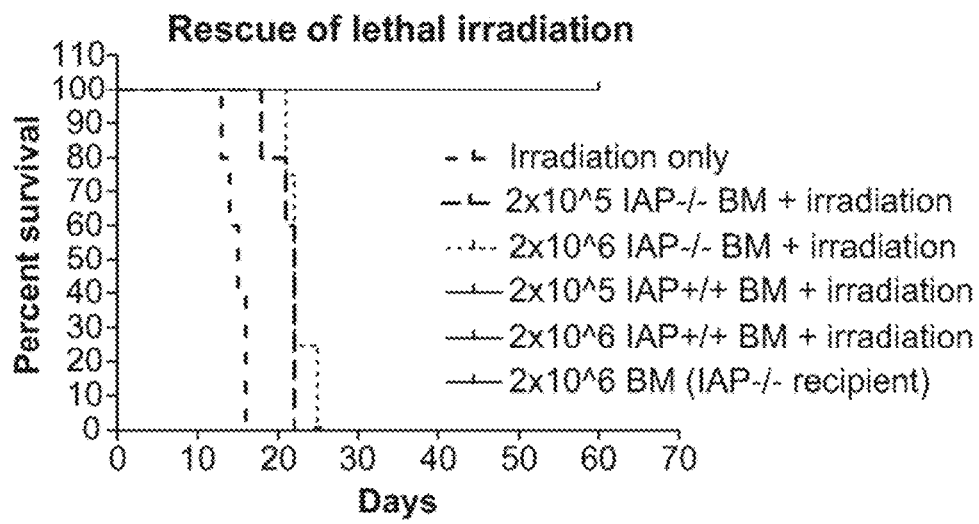

We then asked if bone marrow cells from $IAP^{-/-}$ mice could rescue recipient mice from the effects of lethal irradiation. Typically, a dose of $2 \times 10^5$ bone marrow cells will rescue 100% of wild-type recipient mice in this assay. We found that $IAP^{-/-}$ bone marrow could not rescue these recipients (FIG. 18c). However, administration of these cells did prolong lifespan; normally, mice die between day 12 and 15 after irradiation, but mice that received $IAP^{-/-}$ bone marrow lived about 7 to 10 days longer (FIG. 18c). We do not yet know the reason for the prolongation of lifespan in this case, although we have observed that multipotent progenitors and megakaryocyte erythrocyte progenitors can prolong survival after lethal irradiation, and that contribution from these cells following transplant of whole bone marrow may have contributed to the elongation of survival time.

Figure 18D:
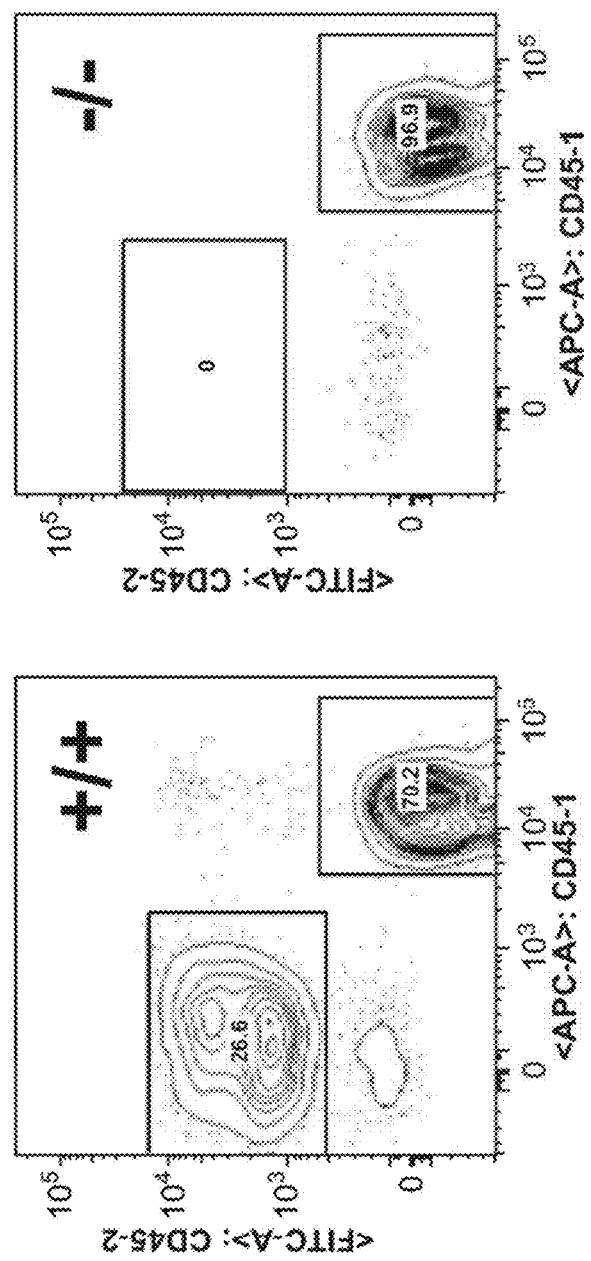
Figure 18E:
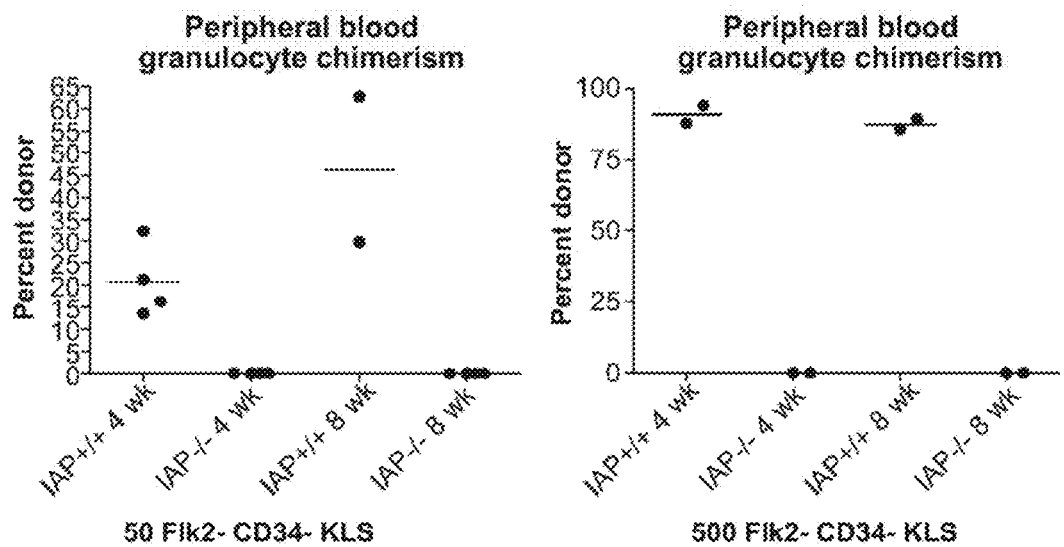
Figure 18F:
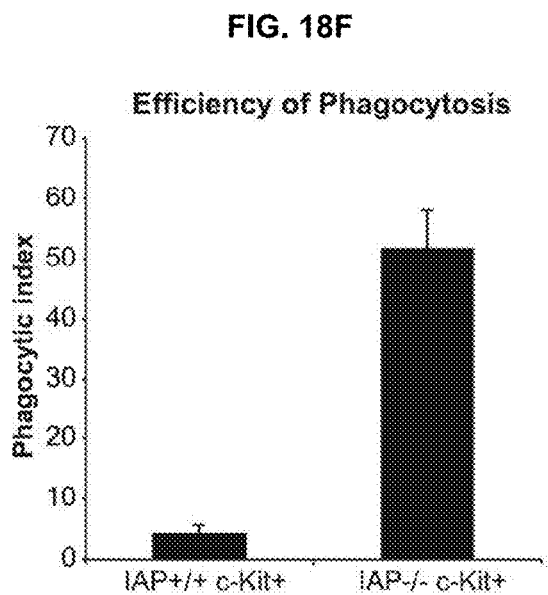
Figure 18G:
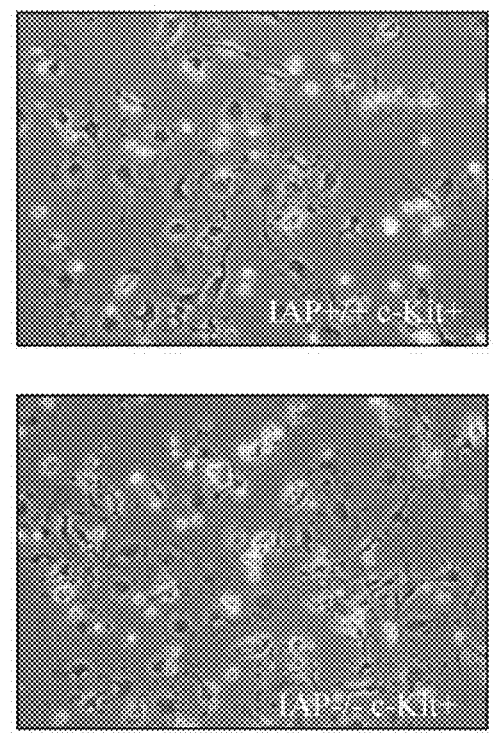

Next, we sorted Flk-2− CD34− KLS stem cells from wild-type and $IAP^{-/-}$ cells and transplanted them into wild-type recipients along with $2 \times 10^5$ competitor cells. None of the mice which received $IAP^{-/-}$ HSCs, at either a dose of 50 or 500 had any engraftment of donor cells, indicating that CD47 was indeed required for the ability of these cells to transplant (FIG. 18d-e). We speculated that this was due to phagocytosis of the cells which lacked CD47, as has been shown for erythrocytes and T-cells. To test this, we enriched c-Kit$^+$ cells from the bone marrow of wild-type and $IAP^{-/-}$ mice and co-incubated them with bone marrow derived macrophages. $IAP^{-/-}$ stem and progenitor cells were readily phagocytosed in this assay, whereas wild-type cells were only minimally phagocytosed (FIG. 18f-g). Interestingly, when incubated with $IAP^{-/-}$ macrophages, there was significantly less phagocytosis of $IAP^{-/-}$ cells, confirming that macrophages from these mice are indeed abnormal in their phagocytic capacity.

Since mobilization of stem and progenitor cells involves several steps in which they come into contact with macrophages (egress from the marrow sinusoids, entry into the marrow and liver sinusoids, and in the splenic marginal zone), we asked if CD47 is up-regulated in the marrow of mice which have been induced to undergo mobilization. The most commonly used protocol involves administering the drug cyclophosphamide (Cy), which kills dividing (mainly myeloid progenitor) cells, followed by treatment with granulocyte colony stimulating factor (G-CSF). This involves administering cyclophosphamide on the first day, and then giving G-CSF every day thereafter. By convention, the first day after cyclophosphamide administration is called day 0. The peak numbers of stem cells in the bone marrow is achieved on day 2; from days 3-4 they egress from the bone marrow into the periphery, and their numbers in the spleen and liver reach a peak at day 5; myeloerythroid progenitors are also mobilized. There is a characteristic rise in the frequency of stem cells and myeloid progenitors during the mobilization response.

Thus, we administered this mobilization protocol to wild-type mice and sacrificed mice on days 2 through 5. We found that there was a notable increase of CD47 on c-Kit$^+$ bone marrow cells on day 2 (FIG. 19a). We found that there was approximately a four-fold increase in the level of CD47 on stem and progenitor cells on day 2 of mobilization (FIG. 19b). The increase was seen at all levels of the myeloid progenitor hierarchy, as LT-HSCs as well as GMPs displayed this increase in CD47 expression (FIG. 19b). By day 5, when egress from the marrow has largely halted, the levels of CD47 had returned to nearly normal levels. In FIG. 19c, the mean fluorescence intensity of CD47 expression on GMPs is shown on days 0 to 5 of mobilization. CD47 levels are actually subnormal following myeloablation on day 0, but they quickly rise to a peak on day 2. The expression quickly lowers thereafter and the levels by day 5 are equivalent to steady state.

Endotoxins are also thought to contribute to bone marrow mobilization. This may represent a physiological response to infection, where normal marrow output of immune cells needs to be increased to clear the offending pathogens. Lipopolysaccharide (LPS) is a cell wall component of gram-negative bacteria. It binds to the lipid binding protein (LBP) in the serum, which can then form a complex with CD1411 and toll-like receptor 4 (TLR-4) 12 on monocytes, macrophages, and dendritic cells. This results in activation of macrophages and results in a pro-inflammatory response. LPS administration has also been shown to increase the phagocytic capacity of macrophages. This may be due to the fact that LBP-LPS complexes act as opsonins.

Figure 19D:
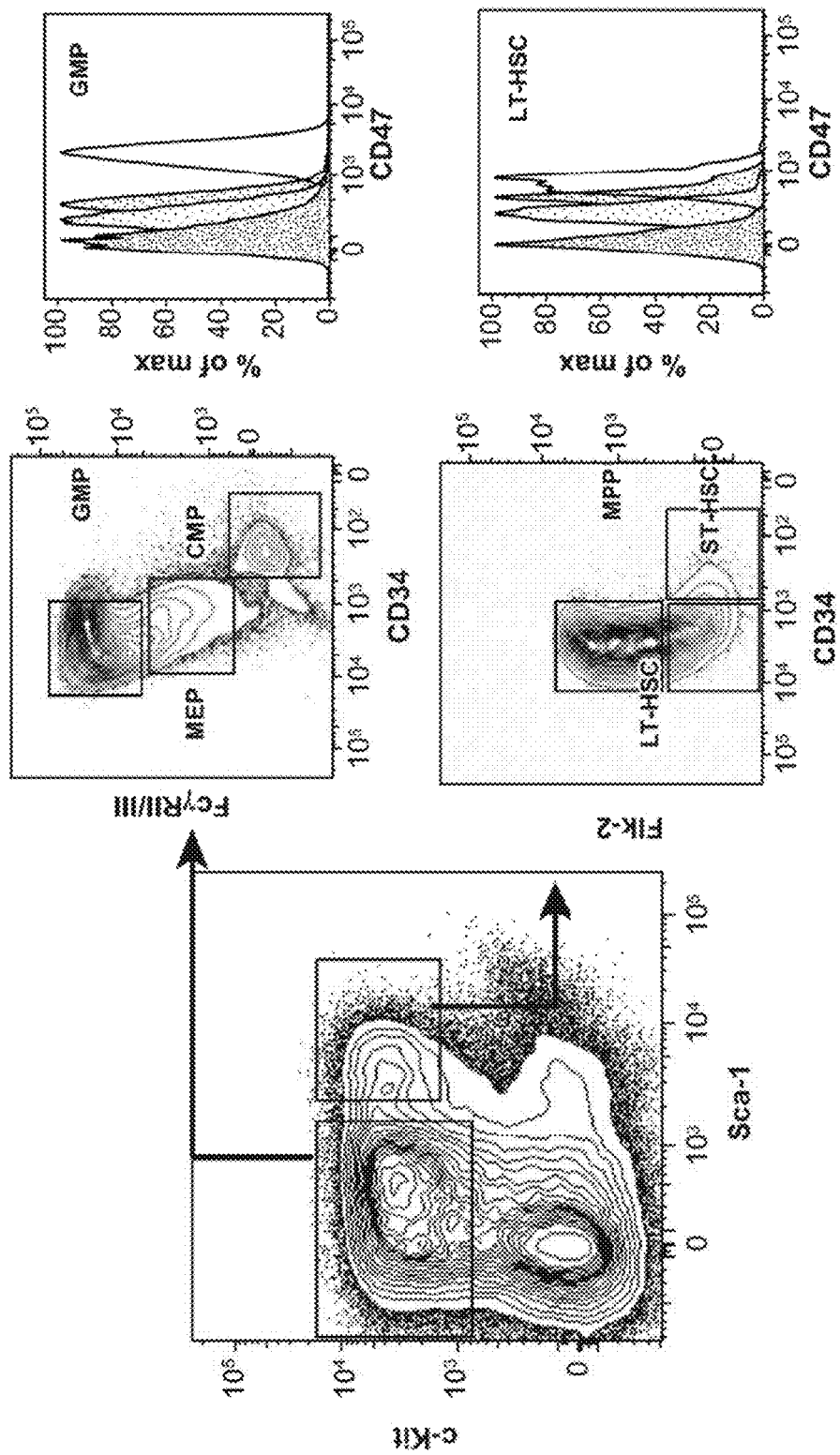

We tested if LPS administration in mice would affect CD47 expression in stem and progenitor cells. Mirroring the pattern seen in Cy/G induced mobilization, LPS caused expansion of stem and progenitor cells by 2 days post treatment, followed by migration to the spleen and liver (FIG. 19d). On day 2 after LPS administration, stem and progenitor cells in the marrow had up-regulated CD47 to a similar degree as in Cy/G mobilization. By day 5, when the inflammatory response has resolved, the levels of the protein had dropped to steady-state levels (FIG. 19d).

Since CD47 was consistently up-regulated in the mobilization response, we decided to test the ability of stem and progenitor cells to mobilize following Cy/G. The CD47 knockout mouse has defects in migration of neutrophils to sites of inflammation8 and of dendritic cells to secondary lymphoid organs. The exact role of CD47 in migration of these cells is unknown, but it may relate to poor integrin association in the circulation (CD47 binds to several integrins) or lack of interaction with SIRPα on endothelial cells. Hence we reasoned that if CD47 was involved in the migration capacity of these cells in the mobilization response, then IAP−/− mice would display reduced numbers of cells in the peripheral organs after Cy/G.

To test this hypothesis we administered Cy/G to both wild-type and knockout mice and sacrificed mice on days 2-5. For each mouse, we analyzed the number of stem and progenitor cells in marrow, spleen, and liver. We decided to use the crude KLS population as a surrogate for HSCs because numbers of CD34− cells drops considerably in proliferative states, making accurate calculation of LT-HSC numbers difficult. Since GMP are the most expanded of all the populations in mobilization, we decided to analyze their numbers as well. To calculate absolute progenitor count, the total cellularity of marrow, spleen, and liver was estimated by counting the mononuclear cell number in the whole organ by hemocytometer. For bone marrow, leg long bones were assumed to represent 15% of the total marrow. This number was then multiplied by the frequency of the cell population to determine an absolute count.

Figure 19E:
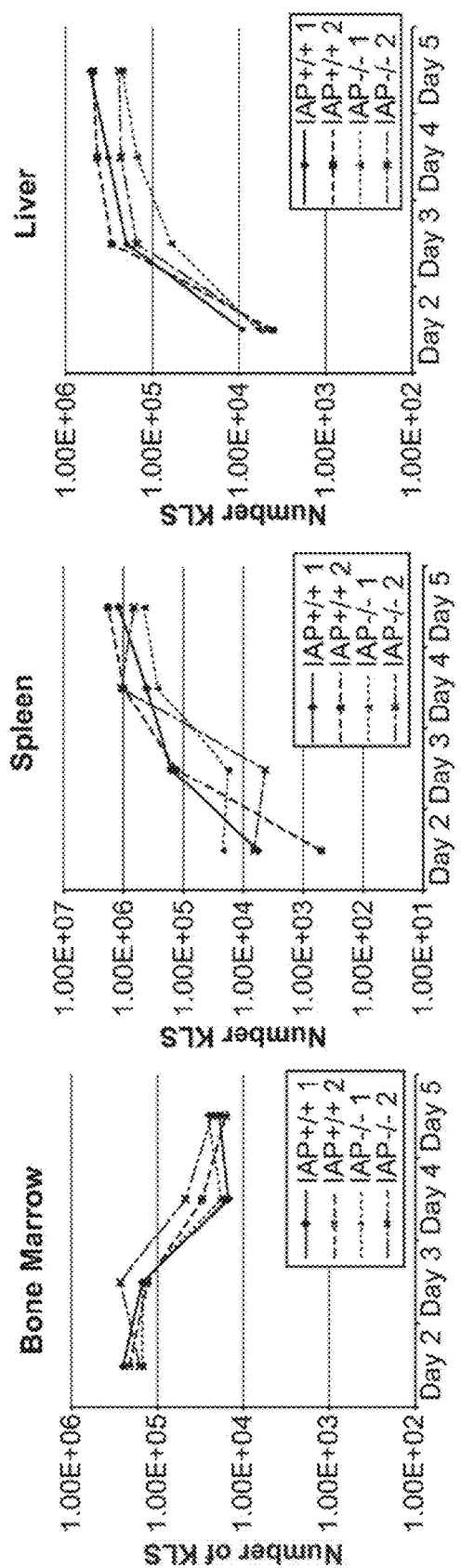

We found that there was little difference in mobilization of KLS or GMP between wild-type and $IAP^{-/-}$ mice (FIG. 19e). There was a modest decrease in the ability of $IAP^{-/-}$ mice to move progenitors to the spleen by day 3, but by days 4 and 5 they had restored normal numbers of cells to the periphery. The marrow and liver compartments looked similar to wild-type mice. Hence, $IAP^{-/-}$ mice do not have a significant mobilization defect.

Heterozygote $IAP^{+/-}$ erythrocytes have roughly the half the amount of CD47 as wild-type erythrocytes and platelets. There is also a dose dependent increase in the amount of phagocytosis that occurs in immunoglobulin opsonized $IAP^{+/-}$ erythrocytes and platelets relative to wild-type. Our observation that CD47 levels increase in states of stress and mobilization led us to hypothesize that cells that were genetically hemizygous for CD47 might be more prone to phagocytosis and clearance by macrophages over time. Hence, we asked if $IAP^{+/-}$ stem cells would be disadvantaged relative to wild-type stem cells in long-term contribution to hematopoiesis.

We first analyzed the levels of CD47 expressed on $IAP^{+/+}$, $IAP^{+/-}$, and $IAP^{-/-}$ stem cells.

FACS analysis of CD34− KLS stem cells revealed that the MFI of CD47 on heterozygote HSCs was indeed at roughly half the level of wild-type stem cells (FIG. 20a). We then transplanted these cells and examined their ability to engraft and produce hematopoietic cells in a recipient. We gave congenic wild-type recipient mice 475 Gy, a sublethal dose of irradiation. We then transplanted one cohort of recipients with 2×10⁶ wild-type whole bone marrow cells, and another with the same dose of $IAP^{+/-}$ bone marrow cells. Such a dose would be expected to contain roughly 50-100 HSCs. Since granulocyte chimerism in the peripheral blood is a good surrogate marker of stem cell fitness, we analyzed cells from the blood of these recipients at periodic intervals. When wild-type marrow was transplanted into wild-type recipients, granulocyte chimerism was maintained for up to 40 weeks. However, when $IAP^{+/-}$ cells were transplanted, 3 out of 5 mice lost donor chimerism over time, despite having a successful engraftment initially (FIG. 20b).

We have observed that CD47 is up-regulated on the surface of hematopoietic cells in the progression of leukemia. We have also found an analogous increase in the level of CD47 expression when mice were stimulated to mobilize stem and progenitor cells to the periphery using Cy/G, or when they were challenged with LPS. But why is CD47 upregulated in these states? Various studies have described a dose-dependent effect for CD47 in the prevention of phagocytosis. $IAP^{+/-}$ erythrocytes and platelets, which have half the level of CD47 as wild-type cells, are phagocytosed more readily than their normal counterparts. Evidence also indicates that the level of CD47 expression on cells correlates well with the ability of the cell to engage the SIRPα inhibitory receptor on macrophages. Recently Danska et al reported that the ability of NOD-SCID mice to support transplantation of human hematopoietic cells correlated with a mutation in the SIRPalpha receptor in these mice. Here we show that stem and progenitor cells that express higher levels of CD47 are less likely to be cleared by phagocytosis.

These studies point to a role for CD47 up-regulation in protecting hematopoietic stem cells during states when they are more prone to being phagocytosed by macrophages, such as post-myeloablation and during mobilization. Macrophages have the function of removing aged or damaged cells that they encounter; it seems that they can eliminate damaged stem cells as well. Thus, healthy recovering stem cells might up-regulate CD47 during a mobilization response to prevent clearance, whereas damaged stem cells fail to do so and are cleared. We speculate that this is a mechanism by which the hematopoietic system self-regulates itself to ensure that only healthy, undamaged cells are permitted to survive and proliferate and utilize resources during high stress states. The mobilization of HSC and progenitors into the bloodstream and thence to hematopoietic sites following LPS induced inflammation is very interesting; HSC migrate from blood to marrow using integrin α4β1 (Wagers and Weissman, Stem Cells 24(4):1087-94, 2006) and the chemokine receptor CXCR4 (Wright D E et al., J Exp Med 195(9): 1145-54, 2002). We have shown previously that integrin α4β1 binds to VCAM1 on hematopoietic stroma (Mikaye K et al. J Exp Med 173(3): 599-607, 1991); VCAM1 is also the vascular addressin on vessels that inflammatory T cells use to recognize and enter local sites of cell death and inflammation. In addition to expressing the integrin associated protein CD47, itinerant HSC express functional integrin α4β1, leading to the speculation that migrating hematopoietic stem and progenitors in states of inflammation may not only re-seed marrow hematopoiesis, but also participate in local inflammation as well.

Materials and Methods

Mice. 057B1/6 CD45.1 and 057B1/6 CD45.2 (wild-type) mice were maintained in our colony. IAP−/− mice were obtained from Eric Brown (University of California, San Francisco). These were bred on C57B16/J background and crossed with our wild-type colony.

Screening. IAP+/− were crossed to each other to generate IAP−/− and IAP+/— offspring. Mice were screened by PCR of tail DNA. The following primers were used: 3′ Neo-GCATCGCATTGTCTGAGTAGGTGTCATTCTATTC; 5′IAP-TCACCTTGTTGTTCCTGTACTAC AAGCA; 3′ IAP-TGTCACTTCGCAAGTGTAGTTCC.

Cell staining and sorting. Staining for mouse stem and progenitor cells was performed using the following monoclonal antibodies: Mac-1, Gr-1, CD3, CD4, CD8, B220, and Ter119 conjugated to Cy5-PE (eBioscience) were used in the lineage cocktail, c-Kit PE-Cy7 (eBioscience), Sca-1 Alexa680 (e13-161-7, produced in our lab), CD34 FITC (eBioscience), CD16/32(FcGRII/III) APC (Pharmingen), and CD135(Flk-2) PE (eBioscience) were used as previously described to stain mouse stem and progenitor subsets 21 22. Mouse CD47 antibody (clone mIAP301) was assessed using biotinylated antibody produced in our lab. Cells were then stained with streptavidin conjugated Quantum Dot 605 (Chemicon). Samples were analyzed using a FACSAria (Beckton Dickinson).

CD34– Flk2– KLS stem cells were double-sorted using a BD FACSAria. Peripheral blood cells were obtained from tail vein bleed and red cells were eliminated by Dextran T500 (Sigma) precipitation and ACK lysis. Cells were stained with anti-CD45.1 APC, anti-CD45.2 FITC, anti-Ter119 PE (Pharmingen), anti-B220 Cy5-PE (eBiosciences), anti-CD3 Cascade Blue, and anti-Mac-1 Cy7-PE (eBiosciences). Granulocytes were Ter119– B220– CD3– Mac-1+ SSC hi. Cells were analyzed using a BD FACSAria.

All samples were resuspended in propidium iodide containing buffer before analysis to exclude dead cells. FACS data was analyzed using FloJo software (Treestar).

In vitro colony forming assay. LT-HSC were directly clone sorted into a 96-well plate containing methycellulose media (Methocult 3100) that was prepared as described. The media was also supplemented with recombinant mouse stem cell factor (SCF), interleukin (IL)-3, IL-11, granulocyte-macrophage colony stimulating factor (GM-CSF), thrombopoietin (Tpo) and erythropoietin (Epo). Colonies were scored for CFU-G, CFU-M, CFU-GM, CFU-GEMM, and Meg.

Cell transfers. For whole bone marrow transfers, IAP+/+, IAP+/–, or IAP–/– cells were freshly isolated from leg long bones. Cells were counted using a hemacytometer and resuspended in PBS+2% FCS at 100 uL. For some experiments, CD45.1 cells from C57Bl/6 Ka CD45.1 mice were used as donors into CD45.2 wild-type mice.

For sorted cells, cells were sorted into PBS buffer at the correct dose (i.e. 50 or 500 cells per tube) and resuspended in 100 uL of PBS+2% FCS. For competition experiments, $2\times10^5$ freshly isolated whole bone marrow cells from C57Bl/6 CD45.1 were added to the 100 uL stem cell suspension.

C57Bl/6 Ka CD45.1 or C57Bl/6 J CD45.2 recipient mice were irradiated using a cesium source at the doses indicated. Sub-lethal dose was 4.75 Gray and lethal dose was a split dose of 9.5 Gray. Cells were transferred using a 27-gauge syringe into the retro-orbital sinuses of mice anesthetized with isofluorane.

Mobilization assay. Mice were mobilized with cyclophosphamide (Sigma) (200 mg/kg) and G-CSF (Neupogen) (250 µg/kg) as previously described. Bacterial LPS from *E. coli* 055:B5 (Sigma) was administered at a dose of 40 mg/kg into the peritoneal cavity.

For analysis of mobilized organs, whole spleen, whole liver, and leg long bones were prepared in a single cell suspension. Cell density was determined using a hemacytometer to determine overall cellularity of hematopoietic cells in these organs.

Enrichment of c-Kit+ cells. Whole mouse marrow was stained with CD117 microbeads (Miltenyi). c-Kit+ cells were selected on an AutoMACS Midi column (Miltenyi) using a magnetic separator.

In vitro phagocytosis assay. BMDM were prepared as previously described. c-Kit enriched bone marrow cells were stained with CFSE (Invitrogen) prior to the assay. $2.5\times10^5$ c-Kit enriched cells were plated with $5\times10^4$ macrophages. Macrophages and c-Kit cells were obtained from either IAP+/+ or IAP–/– mice. Cells were incubated for 2 hours and phagocytic index was determined. Photographs were taken as described previously.

Example 4

CD47 is an Independent Prognostic Factor and Therapeutic Antibody Target on Human Acute Myeloid Leukemia Cells Acute myelogenous leukemia (AML) is organized as a cellular hierarchy initiated and maintained by a subset of self-renewing leukemia stem cells (LSC). We hypothesized that increased CD47 expression on AML LSC contributes to pathogenesis by inhibiting their phagocytosis through the interaction of CD47 with an inhibitory receptor on phagocytes. We found that CD47 was more highly expressed on AML LSC than their normal counterparts, and that increased CD47 expression predicted worse overall survival in 3 independent cohorts of adult AML patients. Furthermore, blocking monoclonal antibodies against CD47 preferentially enabled phagocytosis of AML LSC by macrophages in vitro, and inhibited their engraftment in vivo. Finally, treatment of human AML-engrafted mice with anti-CD47 antibody eliminated AML in vivo. In summary, increased CD47 expression is an independent poor prognostic factor that can be targeted on human AML stem cells with monoclonal antibodies capable of stimulating phagocytosis of LSC.

Results

CD47 is More Highly Expressed on AML LSC than Their Normal Counterparts and is Associated with the FLT3-ITD Mutation. In our investigation of several mouse models of myeloid leukemia, we identified increased expression of CD47 on mouse leukemia cells compared to normal bone marrow. This prompted investigation of CD47 expression on human AML LSC and their normal counterparts. Using flow cytometry, CD47 was more highly expressed on multiple specimens of AML LSC than normal bone marrow HSC and MPP (FIG. 6). This increased expression extended to the bulk leukemia cells, which expressed CD47 similarly to the LSC-enriched fraction.

Examination of a subset of these samples indicated that CD47 surface expression correlated with CD47 mRNA expression. To investigate CD47 expression across morphologic, cytogenetic, and molecular subgroups of AML, gene expression data from a previously described cohort of 285 adult patients were analyzed (Valk et al., 2004 N Engl J Med 350, 1617-1628). No significant difference in CD47 expression among FAB (French-American-British) subtypes was found. In most cytogenetic subgroups, CD47 was expressed at similar levels, except for cases harboring t(8;21)(q22;q22), a favorable risk group which had a statistically significant lower CD47 expression. In molecularly characterized AML subgroups, no significant association was found between CD47 expression and mutations in the tyrosine kinase domain of FLT3 (FLT3-TKD), over-expression of EVI1, or mutations in CEBPA, NRAS, or KRAS. However, higher CD47 expression was strongly correlated with the presence of FLT3-ITD (p<0.001), which is observed in nearly one third of AML with normal karyotypes and is associated with worse overall survival. This finding was separately confirmed in two independent datasets of 214 and 137 AML patients (Table 1).

TABLE 1

Clinical and Molecular Characteristic of AML Samples from the Validation Cohort and Comparison Between Low CD47 and High CD47 Expression Groups

| Clinical Feature* | Overall n = 137 | Low CD47 n = 95 | High CD47 n = 37 | P† |
|---|---|---|---|---|
| Age, yrs | | | | 0.26 |
| Median | 46 | 47 | 46 | |
| Range | 10-60 | 24-60 | 16-60 | |
| WBC, ×10⁹/L | | | | <0.01 |
| Median | 24 | 17 | 35 | |
| Range | 1-238 | 1-178 | 1-238 | |
| Centrally reviewed FAB Classification, no. (%) | | | | 0.29 |
| M0 | 11 (8) | 9 (9) | 2 (5) | |
| M1 | 28 (20) | 16 (17) | 2 (32) | |
| M2 | 36 (26) | 22 (23) | 11 (30) | |
| M4 | 33 (24) | 25 (26) | 8 (22) | |
| M5 | 19 (14) | 16 (17) | 3 (8) | |
| M6 | 2 (1) | 2 (1) | 0 (0) | |
| Unclassified | 6 (4) | 4 (4) | 0 (0) | |
| FLT3-ITD, no. (%) | | | | <0.05 |
| Negative | 84 (61) | 63 (66) | 17 (46) | |
| Positive | 53 (39) | 32 (34) | 20 (54) | |
| FLT3-TKD, no. (%) | | | | 0.24 |
| Negative | 109 (87) | 78 (89) | 27 (79) | |
| Positive | 17 (13) | 10 (11) | 7 (21) | |
| NPMI, no. (%) | | | | 0.10 |
| Wild-Type | 55 (45) | 41 (49) | 10 (30) | |
| Mutated | 66 (55) | 43 (51) | 23 (70) | |
| CEBPA, no. (%) | | | | 1 |
| Wild-Type | 100 (86) | 70 (86) | 27 (87) | |
| Mutated | 16 (14) | 11 (14) | 4 (13) | |
| MLL-PTD, no. (%) | | | | 1 |
| Negative | 121 (93) | 83 (92) | 34 (94) | |
| Positive | 9 (7) | 7 (8) | 2 (6) | |
| Event-free survival | | | | 0.004 |
| Median, mos. | 14 | 17.1 | 6.3 | |
| Disease-free at 3 yrs. % (95% CI) | 36 (27-44) | 41 (31-52) | 22 (8-36) | |
| Overall survival | | | | 0.002 |
| Median, mos. | 18.5 | 22.1 | 9.1 | |
| Alive at 3 yrs, % (95% CI) | 39 (31-48) | 44 (33-55) | 26 (12-41) | |
| Complete remission rate, no. (%) | | | | |
| CR after 1st Induction, no. (%) | 60 (46%) | 46 (48%) | 14 (35%) | 0.33 |
| CR after 2nd Induction, no. (%) | 84 (74%) | 64 (75%) | 20 (69%) | 0.63 |
| Randomization to 2ndary consolidative therapy | | | | |
| Allogeneic-HSCT, no. (%) | 29 (22%) | 25 (26%) | 4 (11%) | 0.09 |

TABLE 1-continued

Clinical and Molecular Characteristic of AML Samples from the Validation Cohort and Comparison Between Low CD47 and High CD47 Expression Groups

| Clinical Feature* | Overall n = 137 | Low CD47 n = 95 | High CD47 n = 37 | P† |
|---|---|---|---|---|
| Autologous-HSCT, no. (%) | 23 (17%) | 17 (18%) | 6 (16%) | 0.98 |

* Tabulated clinical and molecular characteristics at diagnosis. WBC indicates white blood cell count; FAB, French-American-British; FLT3-ITD, internal tandem duplication of the FLT3 gene (for 10 cases with missing FLT3-ITD status, the predicted FLT3-ITD status based on gene expression was substituted using method of Bullinger et al, 2008); FLT3-TKD, tyrosine kinase domain mutation of the FLT3 gene; NPMI, mutation of the NPMI gene; MLL-PTD, partial tandem duplication of the MLL gene; and CEBRA, mutation of the CEBPA gene. CR, complete remission. CR was assessed both after first and second induction regimens, which comprised ICE (idarubicin, etoposide, cytarabine) or A-HAM (all-trans retinoic acid and hige-dose cytarabine plus mitoxantrone). Autologous-HSCT: antologous transplantation; Allogenetic-HSCT, allogenetic transplantation.
† P value, compares difference in molecular and clinical characteristics at diagosis between patients with low and high CD47 mRNA expression values. CD47 expression was dichotomized based on an optimal cut point for overall survival stratification that we identified on an independent microarray dataset published (Valk et al, 2004) as described in supplemental methods.

Identification and Separation of Normal and Leukemic Progenitors From the Same Patient Based On Differential CD47 Expression. In the LSC-enriched Lin−CD34+CD38− fraction of specimen SU008, a rare population of CD47lo-expressing cells was detected, in addition to the majority $CD47^{hi}$-expressing cells (FIG. 21A). These populations were isolated by fluorescence-activated cell sorting (FACS) to >98% purity and either transplanted into newborn NOG mice or plated into complete methylcellulose. The $CD47^{hi}$ cells failed to engraft in vivo or form any colonies in vitro, as can be observed with some AML specimens.

However, the $CD47^{lo}$ cells engrafted with normal myelo-lymphoid hematopoiesis in vivo and formed numerous morphologically normal myeloid colonies in vitro (FIG. 21B,C). This specimen harbored the FLT3-ITD mutation, which was detected in the bulk leukemia cells (FIG. 21D). The purified $CD47^{hi}$ cells contained the FLT3-ITD mutation, and therefore, were part of the leukemic clone, while the $CD47^{lo}$ cells did not. Human cells isolated from mice engrafted with the $CD47^{lo}$ cells contained only wild type FLT3, indicating that the $CD47^{lo}$ cells contained normal hematopoietic progenitors.

Increased CD47 Expression in Human AML is Associated with Poor Clinical Outcomes. We hypothesized that increased CD47 expression on human AML contributes to pathogenesis. From this hypothesis, we predicted that AML with higher expression of CD47 would be associated with worse clinical outcomes. Consistent with this hypothesis, analysis of a previously described group of 285 adult AML patients with diverse cytogenetic and molecular abnormalities (Valk et al., 2004) revealed that a dichotomous stratification of patients into low CD47 and high CD47 expression groups was associated with a significantly increased risk of death in the high expressing group (p=0.03). The association of overall survival with this dichotomous stratification of CD47 expression was validated in a second test cohort of 242 adult patients (Metzeler et al., 2008 Blood) with normal karyotypes (NK-AML) (p=0.01).

Applying this stratification to a distinct validation cohort of 137 adult patients with normal karyotypes (Bullinger et al., 2008 Blood 111, 4490-4495), we confirmed the prognostic value of CD47 expression for both overall and event-free survival (FIG. 22). Analysis of clinical characteristics of the low and high CD47 expression groups in this cross-validation cohort also identified statistically significant differences in white blood cell (WBC) count and FLT3-ITD status, and no differences in rates of complete remission and type of consolidative therapy including allogeneic transplantation (Table 1). Kaplan-Meier analysis demonstrated that high CD47 expression at diagnosis was significantly associated with worse event-free and overall survival (FIG. 22 A,B). Patients in the low CD47 expression group had a median event-free survival of 17.1 months compared to 6.8 months in the high CD47 expression group, corresponding to a hazard ratio of 1.94 (95% confidence interval 1.30 to 3.77, p=0.004). For overall survival, patients in the low CD47 expression group had a median of 22.1 months compared to 9.1 months in the high CD47 expression group, corresponding to a hazard ratio of 2.02 (95% confidence interval 1.37 to 4.03, p=0.002). When CD47 expression was considered as a continuous variable, increased expression was also associated with a worse event-free (p=0.02) and overall survival (p=0.02).

Despite the association with FLT3-ITD (Table 1), increased CD47 expression at diagnosis was significantly associated with worse event-free and overall survival in the subgroup of 74 patients without FLT3-ITD, when considered either as a binary classification (FIG. 22C,D) or as a continuous variable (p=0.02 for both event-free and overall survival). In multivariable analysis considering age, FLT3-ITD status, and CD47 expression as a continuous variable, increased CD47 expression remained associated with worse event-free survival with a hazard ratio of 1.33 (95% confidence interval 1.03 to 1.73, p=0.03) and overall survival with a hazard ratio of 1.31 (95% confidence interval 1.00 to 1.71, p=0.05) (Table 2).

TABLE 2

| Outcome Measure/Variables Considered | HR | 95% CI | P |
|---|---|---|---|
| Event-free survival | | | |
| CD47 expression, continuous, per 2-fold increase | 1.33 | 1.03-1.73 | 0.03 |
| FLT3-ITD, positive vs. negative | 2.21 | 1.39-3.53 | <0.001 |
| Age, per year | 1.03 | 1.00-1.05 | 0.03 |
| Overall survival | | | |
| CD47 expression, continuous, per 2-fold increase | 1.31 | 1.00-1.71 | 0.05 |
| FLT3-ITD, positive vs. negative | 2.29 | 1.42-3.68 | <0.001 |
| Age, per year | 1.03 | 1.01-1.06 | 0.01 |

Monoclonal Antibodies Directed Against Human CD47 Preferentially Enable Phagocytosis of AML LSC by Human Macrophages. We hypothesized that increased CD47 expression on human AML contributes to pathogenesis by inhibiting phagocytosis of leukemia cells, leading us to predict that disruption of the CD47-SIRPα interaction with a monoclonal antibody directed against CD47 will preferentially enable the phagocytosis of AML LSC. Several anti-human CD47 monoclonal antibodies have been generated including some capable of blocking the CD47-SIRPα interaction (B6H12.2 and BRIC126) and others unable to do so (2D3) (Subramanian et al., 2006 Blood 107, 2548-2556). The ability of these antibodies to enable phagocytosis of AML LSC, or normal human bone marrow CD34+ cells, by human macrophages in vitro was tested. Incubation of AML LSC with human macrophages in the presence of IgG1 isotype control antibody or mouse anti-human CD45 IgG1 monoclonal antibody did not result in significant phagocytosis as determined by either immunofluorescence microscopy (FIG. 8A) or flow cytometry. However, addition of the blocking anti-CD47 antibodies B6H12.2 and BRIC126, but not the non-blocking 2D3, enabled phagocytosis of AML LSC (FIG. 8A,C). No phagocytosis of normal CD34+ cells was observed with any of the antibodies (FIG. 8C).

Monoclonal Antibodies Directed Against Human CD47 Enable Phagocytosis of AML LSC by Mouse Macrophages. The CD47-SIRPα interaction has been implicated as a critical regulator of xenotransplantation rejection in several cross species transplants; however, there are conflicting reports of the ability of CD47 from one species to bind and stimulate SIRPα of a different species. In order to directly assess the effect of inhibiting the interaction of human CD47 with mouse SIRPα, the in vitro phagocytosis assays described above were conducted with mouse macrophages. Incubation of AML LSC with mouse macrophages in the presence of IgG1 isotype control antibody or mouse anti-human CD45 IgG1 monoclonal antibody did not result in significant phagocytosis as determined by either immunofluorescence microscopy (FIG. 8B) or flow cytometry. However, addition of the blocking anti-CD47 antibodies B6H12.2 and BRIC126, but not the non-blocking 2D3, enabled phagocytosis of AML LSC (FIG. 8B,C).

A Monoclonal Antibody Directed Against Human CD47 Inhibits AML LSC Engraftment and Eliminates AML in Vivo. The ability of the blocking anti-CD47 antibody B6H12.2 to target AML LSC in vivo was tested. First, a pre-coating strategy was utilized in which AML LSC were purified by FACS and incubated with IgG1 isotype control, anti-human CD45, or anti-human CD47 antibody. An aliquot of the cells was analyzed for coating by staining with a secondary antibody demonstrating that both anti-CD45 and anti-CD47 antibody bound the cells (FIG. 10A). The remaining cells were transplanted into newborn NOG mice that were analyzed for leukemic engraftment 13 weeks later (FIG. 10B). In all but one mouse, the isotype control and anti-CD45 antibody coated cells exhibited long-term leukemic engraftment. However, most mice transplanted with cells coated with anti-CD47 antibody had no detectable leukemia engraftment.

Next, a treatment strategy was utilized in which mice were first engrafted with human AML LSC and then administered daily intraperitoneal injections of 100 micrograms of either mouse IgG or anti-CD47 antibody for 14 days, with leukemic engraftment determined pre- and post-treatment. Analysis of the peripheral blood showed near complete elimination of circulating leukemia in mice treated with anti-CD47 antibody, often after a single dose, with no response in control mice (FIG. 23A,B). Similarly, there was a significant reduction in leukemic engraftment in the bone marrow of mice treated with anti-CD47 antibody, while leukemic involvement increased in control IgG-treated mice (FIG. 23 C,D). Histologic analysis of the bone marrow identified monomorphic leukemic blasts in control IgG-treated mice (FIG. 23E, panels 1,2) and cleared hypocellular areas in anti-CD47 antibody-treated mice (FIG. 23E, panels 4,5). In the bone marrow of some anti-CD47 antibody-treated mice that contained residual leukemia, macrophages were detected containing phagocytosed pyknotic cells, capturing the elimination of human leukemia (FIG. 23E, panels 3,6).

We report here the identification of higher expression of CD47 on AML LSC compared to their normal counterparts and hypothesize that increased expression of CD47 on human AML contributes to pathogenesis by inhibiting phagocytosis of these cells through the interaction of CD47 with SIRPα. Consistent with this hypothesis, we demonstrate that increased expression of CD47 in human AML is associated with decreased overall survival. We also demonstrate that disruption of the CD47-SIRPα interaction with monoclonal antibodies directed against CD47 preferentially enables phagocytosis of AML LSC by macrophages in vitro, inhibits the engraftment of AML LSC, and eliminates AML in vivo. Together, these results establish the rationale for considering the use of an anti-CD47 monoclonal antibody as a novel therapy for human AML.

The pathogenic influence of CD47 appears mechanistically distinct from the two main complementing classes of mutations in a model proposed for AML pathogenesis. According to this model, class I mutations, which primarily impact proliferation and apoptosis (for example, FLT3 and NRAS), and class II mutations, which primarily impair hematopoietic cell differentiation (for example, CEBPA, MLL, and NPM1), cooperate in leukemogenesis. As demonstrated here, CD47 contributes to pathogenesis via a distinct mechanism, conferring a survival advantage to LSC and progeny blasts through evasion of phagocytosis by the innate immune system. While strategies for the evasion of immune responses have been described for many human tumors, we believe that increased CD47 expression represents the first such immune evasion mechanism with prognostic and therapeutic implications for human AML.

Higher CD47 Expression is a Marker of Leukemia Stem Cells and Prognostic for Overall Survival in AML. AML LSC are enriched in the Lin−CD34+CD38− fraction, which in normal bone marrow contains HSC and MPP. The identification of cell surface molecules that can distinguish between leukemic and normal stem cells is essential for flow cytometry-based assessment of minimal residual disease (MRD) and for the development of prospective separation strategies for use in cellular therapies. Several candidate molecules have recently been identified, including CD123, CD96, CLL-1, and now CD47. CD123 was the first molecule demonstrated to be more highly expressed on AML LSC compared to normal HSC-enriched populations. We previously identified AML LSC-specific expression of CD96 compared to normal HSC, and demonstrated that only CD96+, and not CD96−, leukemia cells were able to engraft in vivo.

CLL-1 was identified as an AML LSC-specific surface molecule expressed on most AML samples and not normal HSC; importantly, the presence of Lin−CD34+CD38−CLL-1+ cells in the marrow of several patients in hematologic remission was predictive of relapse. Here we demonstrate that not only is CD47 more highly expressed on AML LSC compared to normal HSC and MPP, but that this differential expression can be used to separate normal HSC/MPP from LSC. This is the first demonstration of the prospective separation of normal from leukemic stem cells in the same patient sample, and offers the possibility of LSC-depleted autologous HSC transplantation therapies.

We initially identified higher expression of CD47 on AML LSC, but noted that expression in bulk blasts was the same. Because of this, we decided to utilize published gene expression data on bulk AML to investigate the relationship between CD47 expression and clinical outcomes. Consistent with our hypothesis, we found that increased CD47 expression was independently predictive of a worse clinical outcome in AML patients with a normal karyotype, including the subset without the FLT3-ITD mutation, which is the largest subgroup of AML patients. As this analysis was dependent on the relative expression of CD47 mRNA, a quantitative PCR assay for AML prognosis may be based on the level of CD47 expression. Such an assay could be utilized in risk adapted therapeutic decision making, particularly in the large subgroup of AML patients with normal karyotypes who lack the FLT3-ITD mutation.

Targeting of CD47 on AML LSC with Therapeutic Monoclonal Antibodies Cell surface molecules preferentially expressed on AML LSC compared to their normal counterparts are candidates for targeting with therapeutic monoclonal antibodies. Thus far, several molecules have been targeted on AML including CD33, CD44, CD123, and now CD47. CD33 is the target of the monoclonal antibody conjugate gemtuzumab ozogamicin (Mylotarg), which is approved for the treatment of relapsed AML in older patients. Targeting of CD44 with a monoclonal antibody was shown to markedly reduce AML engraftment in mice, with evidence that it acts specifically on LSC to induce differentiation. A monoclonal antibody directed against CD123 was recently reported to have efficacy in reducing AML LSC function in vivo. Here we report that a monoclonal antibody directed against CD47 is able to stimulate phagocytosis of AML LSC in vitro and inhibit engraftment in vivo.

Several lines of evidence suggest that targeting of CD47 with a monoclonal antibody likely acts by disrupting the CD47-SIRPα interaction, thereby preventing a phagocytic inhibitory signal. First, two blocking anti-CD47 antibodies enabled AML LSC phagocytosis, while one non-blocking antibody did not, even though all three bind the cells similarly. Second, in the case of the B6H12.2 antibody used for most of our experiments, the isotype-matched anti-CD45 antibody, which also binds LSC, failed to produce the same effects. In fact, the B6H12.2 antibody is mouse isotype IgG1, which is less effective at engaging mouse Fc receptors than antibodies of isotype IgG2a or IgG2b.

For human clinical therapies, blocking CD47 on AML LSC with humanized monoclonal antibodies promotes LSC phagocytosis through a similar mechanism, as indicated by the human macrophage-mediated in vitro phagocytosis (FIG. 8A,C). Higher CD47 expression is detected on AML LSC; however, CD47 is expressed on normal tissues, including bone marrow HSC. We identified a preferential effect of anti-CD47 antibodies in enabling the phagocytosis of AML LSC compared to normal bone marrow CD34+ cells by human macrophages in vitro. In fact, no increased phagocytosis of normal CD34+ cells compared to isotype control was detected, demonstrating that blocking CD47 with monoclonal antibodies is a viable therapeutic strategy for human AML.

The experimental evidence presented here provides the rationale for anti-CD47 monoclonal antibodies as monotherapy for AML. However, such antibodies may be equally, if not more effective as part of a combination strategy. The combination of an anti-CD47 antibody, able to block a strong inhibitory signal for phagocytosis, with a second antibody able to bind a LSC-specific molecule (for example CD96) and engage Fc receptors on phagocytes, thereby delivering a strong positive signal for phagocytosis, may result in a synergistic stimulus for phagocytosis and specific elimination of AML LSC. Furthermore, combinations of monoclonal antibodies to AML LSC that include blocking anti-CD47 and human IgG1 antibodies directed against two other cell surface antigens will be more likely to eliminate leukemia cells with pre-existing epitope variants or antigen loss that are likely to recur in patients treated with a single antibody.

Experimental Procedures

Human Samples. Normal human bone marrow mononuclear cells were purchased from AllCells Inc. (Emeryville, Calif.). Human acute myeloid leukemia samples (FIG. 1A) were obtained from patients at the Stanford University Medical Center with informed consent, according to an IRB-approved protocol (Stanford IRB #76935 and 6453). Human CD34− positive cells were enriched with magnetic beads (Miltenyi Biotech).

Flow Cytometry Analysis and Cell Sorting. A panel of antibodies was used for analysis and sorting of AML LSC (Lin−CD34+CD38−CD90−, where lineage included CD3, CD19, and CD20), HSC (Lin−CD34+CD38−CD90+), and MPP (Lin−CD34+CD38−CD90−CD45RA−) as previously described (Majeti et al., 2007). Analysis of CD47 expression was performed with an anti-human CD47 PE antibody (clone B6H12, BD Biosciences, San Jose Calif.).

Genomic DNA Preparation and Analysis of FLT3-ITD by PCR. Genomic DNA was isolated from cell pellets using the Gentra Puregene Kit according to the manufacturer's protocol (Gentra Systems, Minneapolis, Minn.). FLT3-ITD status was screened by PCR using primers that generated a wild-type product of 329 bp and ITD products of variable larger sizes.

Anti-Human CD47 Antibodies. Monoclonal mouse anti-human CD47 antibodies included: BRIC126, IgG2b (Abcam, Cambridge, Mass.), 2D3, IgG1 (Ebiosciences. San Diego, Calif.), and B6H12.2, IgG1. The B6H12.2 hybridoma was obtained from the American Type Culture Collection (Rockville, Md.). Antibody was either purified from hybridoma supernatant using protein G affinity chromatography according to standard procedures or obtained from BioXCell (Lebanon, N.H.).

Methylcellulose Colony Assay. Methylcellulose colony formation was assayed by plating sorted cells into a 6-well plate, each well containing 1 ml of complete methylcellulose (Methocult GF+ H4435, Stem Cell Technologies). Plates were incubated for 14 days at 37° C., then scored based on morphology.

In Vitro Phagocytosis Assays. Human AML LSC or normal bone marrow CD34+ cells were CFSE-labeled and incubated with either mouse or human macrophages in the presence of 7 µg/ml IgG1 isotype control, anti-CD45 IgG1, or anti-CD47 (clones B6H12.2, BRIC126, or 2D3) antibody for 2 hours. Cells were then analyzed by fluorescence microscopy to determine the phagocytic index (number of cells ingested per 100 macrophages). In some cases, cells were then harvested and stained with either a mouse or human macrophage marker and phagocytosed cells were identified by flow cytometry as macrophage+CFSE+. Statistical analysis using Student's t-test was performed with GraphPad Prism (San Diego, Calif.).

In Vivo Pre-Coating Engraftment Assay. LSC isolated from AML specimens were incubated with 28 ug/mL of IgG1 isotype control, anti-CD45 IgG1, or anti-CD47 IgG1 (B6H12.2) antibody at 4° C. for 30 minutes. A small aliquot of cells was then stained with donkey anti-mouse PE secondary antibody (Ebioscience) and analyzed by flow cytometry to assess coating. Approximately $10^5$ coated LSC were then transplanted into each irradiated newborn NOD.Cg-Prkdcscidll2rgtm1Wjl/SzJ (NOG) mouse. Mice were sacrificed 13 weeks post-transplantation and bone marrow was analyzed for human leukemia engraftment (hCD45+ hCD33+) by flow cytometry (Majeti et al., 2007 Cell Stem Cell 1, 635-645). The presence of human leukemia was confirmed by Wright-Giemsa staining of hCD45+ cells and FLT3-ITD PCR. Statistical analysis using Student's t-test was performed with GraphPad Prism (San Diego, Calif.).

In Vivo Antibody Treatment of AML Engrafted Mice. 1–25×$10^5$ FACS-purified LSC were transplanted into NOG pups. Eight to twelve weeks later, human AML engraftment (hCD45+CD33+ cells) was assessed in the peripheral blood and bone marrow by tail bleed and aspiration of the femur, respectively. Engrafted mice were then treated with daily intraperitoneal injections of 100 micrograms of anti-CD47 antibody or IgG control for 14 days. On day 15 mice were sacrificed and the peripheral blood and bone marrow were analyzed for AML.

AML Patients, Microarray Gene Expression Data, and Statistical Analysis. Gene expression and clinical data were analyzed for three previously described cohorts of adult AML patients: (1) a training dataset of 285 patients with diverse cytogenetic and molecular abnormalities described by Valk et al., (2) a test dataset of 242 patients with normal karyotypes described by Metzeler et al., and (3) a validation dataset of 137 patients with normal karyotypes described by Bullinger et al. The clinical end points analyzed included overall and event-free survival, with events defined as the interval between study enrollment and removal from the study owing to a lack of complete remission, relapse, or death from any cause, with data censored for patients who did not have an event at the last follow-up visit.

FLT3-ITD PCR. All reactions were performed in a volume of 50 µl containing 5 µl of 10× PCR buffer (50 mM KCL/10 nM Tris/2 mM MgCl2/0.01% gelatin), 1 µl of 10 mM dNTPs, 2 units of Taq polymerase (Invitrogen), 1 ul of 10 µM forward primer 11F (5'-GCAATTTAGGTAT-GAAAGCCAGC-3') and reverse primer 12R (5'-CTTTCA-GCATTTTGACGGCAACC-3'), and 10-50 ng of genomic DNA. PCR conditions for amplification of the FLT3 gene were 40 cycles of denaturation (30 sec at 95° C.) annealing (30 sec at 62° C.), and extension (30 sec at 72° C.).

Preparation of Mouse and Human Macrophages. BALB/c mouse bone marrow mononuclear cells were harvested and grown in IMDM containing 10% FBS supplemented with 10 ng/mL recombinant murine macrophage colony stimulating factor (M-CSF, Peprotech, Rocky Hill, N.J.) for 7-10 days to allow terminal differentiation of monocytes to macrophages. Human peripheral blood mononuclear cells were prepared from discarded normal blood from the Stanford University Medical Center. Monocytes were isolated by adhering mononuclear cells to culture plates for one hour at 37° C., after which non-adherent cells were removed by washing. The remaining cells were >95% CD14 and CD11b positive. Adherent cells were then incubated in IMDM plus 10% human serum (Valley Biomedical, Winchester, Va.) for 7-10 days to allow terminal differentiation of monocytes to macrophages.

In vitro phagocytosis assay. BMDM or peripheral blood macrophages were harvested by incubation in trypsin/EDTA (Gibco/lnvitrogen) for 5 minutes followed by gentle scraping. 5×$10^4$ macrophages were plated in each well of a 24-well tissue culture plate in 10% IMDM containing 10% FBS. After 24 hours, media was replaced with serum-free IMDM and cells were cultured an additional 2 hours. LSC were fluorescently labeled with CFSE according to the manufacturer's protocol (Invitrogen). 2×$10^4$ CFSE-labeled LSC were added to the macrophage-containing wells along with 7 µg/mL of IgG1 isotype (Ebiosciences), anti-CD45 (clone HI30, Ebiosciences), or anti-CD47 antibody, and incubated for 2 hours. Wells were then washed 3 times with IMDM and examined under an Eclipse T5100 immunofluorescent microscope (Nikon) using an enhanced green fluorescent protein filter able to detected CFSE fluorescence. The number of CFSE positive cells within macrophages was counted and the phagocytic index was determined as the number of ingested cells per 100 macrophages. At least 200 macrophages were counted per well. Flourescent and brightfield images were taken separately and merged with Image Pro Plus (Media Cybernetics, Bethesda, Md.). In FIG. 22A,B, the three left images are presented at 200× magnification, with the anti-CD47 right image at 400× magnification. For flow cytometry analysis of phagocytosis, the cells were then harvested from each well using trypsin/EDTA. Cell suspensions were then stained with a mouse macrophage antibody anti-mouse F4/80-PECy7 (Ebiosciences) or anti-human CD14-PECy7 (Ebiosciences) and analyzed on a FACSAria. Phagocytosed LSC were defined as either CFSE+F4/80+ or CFSE+CD14+ cells when incubated with murine or human macrophages, respectively.

Microarray Gene Expression Data. Panel A of Supplemental FIG. 22 describes the main microarray datasets analyzed herein, including the training, test, and validation cohorts. Training Set: Gene expression data, cytogenetics data, and molecular data for the 285 and 465 patients with AML profiled with Affymetrix HG-U133A and HG-U133 Plus 2.0 microarrays by Valk et al. and Jongen-Lavrencic et al. respectively, were obtained from the Gene Expression Omnibus using the corresponding accession numbers (GSE1159 and GSE6891). Outcome data were only available for the former dataset, and the corresponding clinical information were kindly provided by the authors. This cohort is presented as the "training" dataset. The latter dataset was used to confirm univariate associations with karyotype and molecular mutations described in the former. However, these two datasets overlapped in that 247 of the 285 patients in the first study were included in the second, and were accordingly excluded in validation of the association of FLT3-ITD with CD47 expression in the 2nd dataset. Using NetAffx4, RefSeq5, and the UCSC Genome Browser6, we identified 211075_s_at and 213857_s_at as Affymetrix probe sets on the U133 Plus 2.0 microarray mapping exclusively to constitutively transcribed exons of CD47. The geometric mean of the base-2 logarithms of these two probe sets was employed in estimating the mRNA expression level for CD47, and corresponding statistical measures for associations with FAB classification, karyotype, and molecular mutations. Because the data provided by Valk et al. as GSE1159 were Affymetrix intensity measurements, we converted these intensities to normalized base-2 logarithms of ratios to allow comparison to the corresponding measurements from cDNA microarrays using a conventional scheme. Specifically, we first (1) normalized raw data using CEL files from all 291 microarrays within this dataset using gcRMA8, then (2) generated ratios by dividing the intensity measurement for each gene on a given array by the average intensity of the gene across all arrays, (3) log-transformed (base 2) the resulting ratios, and (4) median centered the expression data across arrays then across genes. For the assessment of the prognostic value of CD47, we employed the probe set 213857_s_at from the Affymetrix HG-U133A and HG-U133 Plus 2.0 microarrays, given its similar expression distribution (Supplemental FIG. 3B), and considering its position within the mRNA transcript as compared with cDNA clones on the Stanford cDNA microarrays as annotated within the NetAffx resource.

Test Set: Gene expression and clinical data for the 242 adult patients with NKAML profiled with Affymetrix HG-U133A and HG-U133 Plus 2.0 microarrays by Metzeler et al. were obtained from the Gene Expression Omnibus using the corresponding accession numbers (GSE12417). Since raw data were not available for this dataset, for purposes of assessing the prognostic value of CD47, we employed the normalized datasets provided by the authors (base 2 logarithms) and assessed expression of CD47 using the probe set 213857_s_at on the corresponding microarrays.

Validation Set: Gene expression data for the 137 patients with normal karyotype AML profiled with cDNA microarrays by Bullinger et al. were obtained from the Stanford Microarray Database10. The corresponding clinical information including outcome data and FLT3 mutation status were kindly provided by the authors. Using the original annotations of microarray features as well as SOURCE11, RefSeq5, and the UCSC Genome Browser6, we identified IMAGE:811819 as a sequence verified cDNA clone mapping to the constitutively transcribed 3' terminal exon of CD47 on the corresponding cDNA microarrays.

Details of Treatment: AML patients described by Valk et al. (training set), were treated according to several protocols of the Dutch-Belgian Hematology-Oncology Cooperative group. The majority (90%) of the NK-AML patients described by Metzeler et al. (test set) were treated per protocol AMLCG-1999 of the German AML Cooperative Group, with all patients receiving intensive double-induction and consolidation chemotherapy. All 137 NK-AML patients described by Bullinger et al. (validation set) received standard-of-care intensified treatment regimens (protocol AML HD98A), which included 2 courses of induction therapy with idarubicin, cytarabine, and etoposide, one consolidation cycle of high-dose cytarabine and mitoxantrone (HAM), followed by random assignment to a late consolidation cycle of HAM versus autologous hematopoietic cell transplantation in case no HLA identical family donor was available for allogeneic hematopoietic cell transplantation.

Statistical Analysis. We used two tailed t-tests and analysis of variance for the estimation of significant differences in CD47 expression level across subgroups of AML based on morphologic, cytogenetic, and molecular categorizations. Associations between the high and low CD47 groups and baseline clinical, demographic, and molecular features were analyzed using Fisher's exact and Mann-Whitney rank sum tests for categorical and continuous variables, respectively. Two-sided p-values of less than 0.05 were considered to indicate statistical significance.

The prognostic value of CD47 expression was measured through comparison of the event-free and overall survival of patients with estimation of survival curves by the Kaplan-Meier product limit method and the log-rank test. Within this analysis, we first derived a binary classification of AML patients into High CD47 and Low CD47 expression groups by comparing the expression of CD47 (as measured by 213857_s_at within GSE1159) relative to an optimal threshold. This threshold was determined using X-Tile16, a method which we employed to maximize the chi-square statistic between the two groups for the expected versus observed number of deaths. This stratification segregates the 261 AML patients with available outcome data into two unequally sized groups, with 72% of patients with lowest expression considered CD47 low, and 28% with highest expression considered CD47 high. These two groups have different overall survival with a hazard ratio of 1.42 for the CD47 high group, and a corresponding uncorrected p-value of 0.033, which requires cross-validation to avoid the risk of overfitting.

Accordingly, we assessed the validity and robustness of risk stratification using CD47 expression by applying this optimal threshold to an independent test cohort of 242 NK-AML patients described by Metzeler et al. Notably, despite the presence of other variables potentially confounding associations with survival (including more advanced age, and differing therapies), derivation of an optimal cutpoint using the 242 NK-AML patients within the test dataset yielded a similar stratification, with 74% of patients with lowest expression considered CD47 low, and 26% with highest expression considered CD47 high.

Next, we assessed the validity of this stratification in a cross-validation cohort of 137 uniformly treated NK-AML patients described by Bullinger et al. Within this validation dataset, we could similarly define two groups of similar size (i.e., 72% and 28% with lowest and highest CD47 levels, respectively), and these two groups had significantly different outcomes when assessed for overall survival (FIG. 22B, p=0.002, hazard ratio 2.02, 95% CI 1.37 to 4.03), and event-free survival (FIG. 22A, p=0.004, hazard ratio 1.94, 95% CI 1.30 to 3.77). Of the 137 patients, 5 did not have reliable measurements for CD47 when using the data selection and normalization criteria described by the authors.

To determine the robustness of this association, we also examined the predictive value of CD47 expression when the validation cohort was divided into low and high CD47 expression groups based on expression relative to the median, or as a continuous variable. As above, higher CD47 expression was associated with worse event-free and overall survival. Of the 137 patients studied, a subset of 123 patients had available survival data, CD47 expression data, and FLT3-ITD status reported. Within this cohort, we assessed the relationship of CD47 expression level as a continuous variable with outcome using univariate Cox proportional-hazards analysis, with event-free survival or overall survival as the dependent variable. We used multivariate Cox-proportional hazards analysis with event-free survival or overall survival as the dependent variable and FLT3-ITD status, age, and continuous expression level of CD47 as directly assessed independent variables.

Associations of CD47 with other covariates (eg, NPM1, CEBPA) were limited by sample size and missing data for covariates. The Wald test was used to assess the significance of each covariate in multivariate analyses. Univariate and multivariate proportional-hazards analyses were done using the coxph function in the R statistical package.

Example 5

CD47 is a Prognostic Factor and Therapeutic Antibody Target on Solid Tumor Cancer Stem Cells We have found that increased CD47 expression is associated with worse clinical outcomes in diffuse large B-cell lymphoma (DLBCL) and ovarian carcinoma (FIG. 24). Additionally, we have now found that anti-CD47 antibodies enable the phagocytosis of cancer stem cells from bladder cancer, ovarian carcinoma, and medulloblastoma in vitro with human macrophages (FIG. 25).

Example 6

Therapeutic Antibody Targeting of CD47 Eliminates Human Acute Lymphoblastic Leukemia Although standard multi-agent chemotherapy cures a significant number of patients with standard-risk pediatric ALL, these same therapies are significantly less effective in both the high-risk pediatric population and in all adults with ALL. Thus, additional therapies are necessary to more effectively treat these patient subsets. As an alternative to chemotherapy, monoclonal antibodies have recently emerged as an attractive therapeutic modality due to the ability to selectively target leukemia cells, thereby minimizing systemic toxicity. Indeed, several monoclonal antibodies are currently in clinical trials for the treatment of ALL.

CD47 is identified herein as a therapeutic antibody target in acute myeloid leukemia (AML). It is investigated whether a blocking monoclonal antibody against CD47 could eliminate primary human ALL in vitro and in vivo, in order to determine the use of an anti-CD47 antibody as a therapy in standard and high-risk ALL.

Materials And Methods

Human Samples. Normal human bone marrow cells were purchased from AllCells Inc. (Emeryville, Calif., USA). Human ALL samples were obtained from patients at the Stanford University Medical Center, with informed consent, according to an IRB-approved protocol.

Flow Cytometry Analysis. The following antibodies were used for analysis of ALL and NBM cells: CD3 APC-Cy7 and CD19 APC (BD Biosciences, San Jose, Calif., USA). Analysis of CD47 expression was performed with an anti-human CD47 FITC antibody (clone B6H12.2, BD Biosciences). For human engraftment analysis in mice, the following antibodies were used: mouse Ter119 PeCy5, mouse CD45.1 PeCy7, human CD45 PB, human CD19 APC, and human CD3 APC-Cy7 (Ebiosciences, San Diego, Calif., USA).

ALL microarray gene expression data and statistical analysis. We used previously described methods for the univariate and multivariate statistical analyses of CD47 gene expression data and its relationship to clinical and pathological variables. Briefly, gene expression and clinical data were analyzed for three previously described cohorts of ALL patients: 1) a dataset of 360 pediatric ALL patients with B- and T-ALL subtypes, diverse risk profiles and corresponding therapies including a subset (n=205) with available data on disease free survival. Microarray and clinical data were obtained from St. Jude Children's Research Hospital; 2) a dataset of 207 pediatric B-precursor ALL patients with high-risk features uniformly treated through the Children's Oncoloy Group Clinical Trial P9906 obtained from NCBI through the Gene Expression Omnibus (GSE11877); and 3) 254 pediatric ALL patients registered to Pediatric Oncology Group trials stratified for the presence of recurrent cytogenetic abnormalities and remission versus failure within each cytogenetic group with data obtained from the National Cancer Institute caArray. Affymetrix probeset summaries were derived from the corresponding microarray raw CEL data files using a Custom Chip Definition File derived from NCBI Reference Sequences (version 12), and then normalized using MAS 5.0 using BioConductor. For survival analyses, NM_198793_at was selected as the probeset to represent CD47 mRNA based on it demonstrating highest expression among the 3 probesets for CD47 on the microarrays, and based on its exonic structure capturing the CD47 splice variant expressed in hematopoietic tissues.

We assessed the relationship of CD47 mRNA expression and outcomes as continuous variables using univariate Cox proportional-hazards analysis, with disease free or overall survival as the dependent variable. Using the coxph function in the R statistical package, the Wald test was used to assess the significance of each covariate, represented by the base-2 logarithms of CD47 mRNA expression. For dichotomous stratification of CD47 expression, we used maximally selected chi-square statistics as implemented within X-tile to define an optimal threshold. To guard against erroneous overestimation of p-values through multiple hypothesis testing, we corrected the log-rank Kaplan-Meier p-values using the Miller-Siegmund method well as sub-sampling (n=1000) based internal cross-validation.

Therapeutic antibodies. Anti-human CD47 antibodies (B6H12.2, BRIC126, 2D3), anti-SIRPα antibody, IgG control, and anti-CD45 antibodies were used as described in the previous examples. The anti-CD47 antibody clone BRIC126 was obtained from AbD Serotec (Raleigh, N.C., USA).

Generation of mouse and human macrophages. Isolation of mouse and human macrophages were performed as previously described. Briefly, femurs and tibias from wild-type Balb/C mice were harvested into a single cell suspension and incubated for 7-10 days in IMDM 10% fetal calf serum with 10 ng/ml murine M-CSF (Peprotech, Rocky Hill, N.J., USA) at 37° C. Cells were then washed and adherent cells trypsinized and plated for in vitro phagocytosis assays. For human macrophages, mononuclear cells were isolated from human peripheral blood by ficoll density gradient centrifugation and plated onto 10 cm petri dishes at 37° C. for one hour. Non-adherent cells were then washed off and the remaining adherent cells were incubated for 7-10 days in IMDM with 10% human AB serum. Cells were then trypsinized and plated for in vitro phagocytosis assays.

In vitro phagocytosis assays. Phagocytosis assays were performed as described in the previous examples. Briefly, bulk ALL cells were CFSE-labeled and incubated with either mouse or human macrophages in the presence of 10 μg/ml of the indicated antibodies at a target:effector cell ratio of 4:1 ($2\times10^5$:$5\times10^4$). Incubation occurred at 37° C. for 2 hours and then analyzed by fluorescent microscopy for phagocytosis using the phagocytic index: number of cells ingested per 100 macrophages.

Ex vivo antibody coating of ALL cells. Human ALL cells were incubated with 30 μg/ml of either IgG1 isotype control, anti-CD45, or anti-CD47 antibody for 30 minutes at 4° C. Cells were washed and then $1\times4\times10^6$ cells were transplanted into sublethally-irradiated NOD.Cg-Prkdc$_{scid/l}$2rg$_{tm1wjl}$/SzJ (NSG) adults or pups and analyzed for ALL engraftment in the peripheral blood and bone marrow 6-10 weeks later. Antibody coating of ALL cells was confirmed by flow cytometry with a secondary antibody prior to transplantation into mice. Sublethal irradiation was 230rads and 100rads for NSG adults and pups, respectively.

In vivo treatment of human ALL engrafted mice. $1-4\times10^6$ bulk human ALL cells were transplanted intravenously via the retro-orbital sinus into sublethally-irradiated (230 rads) adult NSG mice. Alternatively, ALL cells were transplanted into the facial vein of 2-4 day old sublethally-irradiated (100 rads) NSG pups. Six to ten weeks later peripheral blood and bone marrow ALL engraftment (B-ALL: hCD45+CD19+; T-ALL: hCD45+CD3+) was assessed by tail bleed and aspiration of the femur, respectively. Engrafted mice were treated for 14 days with daily 100 μg intraperitoneal injections of either IgG control or anti-CD47 antibody (clone B6H12.2). On day 15, mice were sacrificed and analyzed for ALL engraftment in the peripheral blood, bone marrow, spleen, and liver.

Bone marrow tissue section preparation and staining. Mouse tibias from antibody-treated NSG mice were harvested and preserved in formalin. Hematoxylin and eosin staining and immunohistochemistry of human CD45+ cells were performed by Comparative Biosciences Inc. (Sunnyvale, Calif., USA).

Results

CD47 Expression is Increased on a Subset of Human ALL Cells Compared to Normal Bone Marrow. To determine whether CD47 may be involved in the pathogenesis of ALL, we first investigated CD47 cell surface expression on primary human ALL and normal bone marrow cells by flow cytometry. We surveyed 17 diverse patients with ALL that included both precursor B and T lineage subtypes. Compared to normal mononuclear bone marrow cells, CD47 was more highly expressed on human ALL samples, approximately 2-fold when considering all samples, with similar expression between B and T subtypes. However, assessing CD47 mRNA expression in a large cohort of ALL patients, we found that T-ALL patients expressed significantly higher levels compared to B-ALL patients.

CD47 Expression is an Independent Prognostic Predictor in Mixed and High-Risk ALL. Since CD47 expression was increased on ALL samples, and given the observed heterogeneity in CD47 expression across ALL subtypes, we investigated whether the level of CD47 expression correlated with clinical prognosis. First, CD47 expression was investigated as a prognostic predictor in pediatric ALL patients with mixed risk and treatment utilizing gene expression data from a previously described patient cohort. 360 patients were stratified into high and low CD47-expressing groups based on an optimal cutpoint and clinical outcomes were determined. Among the subset of this cohort with available outcome data (n=205), patients expressing higher levels of CD47 had worse outcomes, whether CD47 expression was tested as a continuous variable (p=0.03; HR 1.78 per 2-fold change in CD47 expression; 95% CI 1.05-3.03), or as a dichotomous variable relative to an internally validated optimal threshold (uncorrected p=0.0005, corrected p=0.01; HR 3.05; 95% CI 1.49-6.26) (FIG. 26A).

Second, to investigate the prognostic power of CD47 expression in high-risk ALL patients, clinical outcome in a uniformly treated previously described cohort of 207 high-risk pediatric ALL patients was investigated. For this cohort, high-risk was defined by age>10 years, presenting WBC count>50,000/μl, hypodiploidy, BCR-ABL positive disease, and central nervous system or testicular involvement. In these high-risk ALL patients, higher CD47 expression correlated with a worse overall survival when CD47 expression was again considered as either a continuous variable (p=0.0009, HR 3.59 per 2-fold change in CD47 expression; 95% CI 1.70 to 7.61), or as a dichotomous one relative to an internally validated optimal threshold (uncorrected p=0.001, corrected p=0.01; HR 2.80; 95% CI 1.21 to 6.50) (FIG. 26B). In multivariate analysis, CD47 expression remained a significant prognostic factor when age at diagnosis, gender, WBC count, CNS involvement, and minimal residual disease were considered as covariates (FIG. 26C).

Lastly, we utilized a third independent gene expression dataset to investigate whether CD47 expression could predict disease relapse. Indeed, CD47 expression was higher in patients failing to achieve a complete remission (CR) compared to those that did achieve a CR (FIG. 26D). Taken together, these separate observations among distinct and diverse cohorts establish that higher expression of CD47 is an independent predictor of adverse outcomes in pediatric patients with standard- and high-risk ALL, including induction failure, relapse, and death.

Blocking Monoclonal Antibodies Against CD47 Enable Phagocytosis of ALL Cells. Next, we investigated whether ALL cells could be eliminated by macrophage phagocytosis enabled through blockade of the CD47-SIRPα interaction with a blocking anti-CD47 antibody. First, we incubated human macrophages with fluorescently-labeled ALL cells in the presence of an IgG1 isotype control, anti-CD45 isotype-matched, or anti-CD47 antibody and measured phagocytosis by immunofluorescence microscopy. Two different blocking anti-CD47 antibodies (B6H12.2 and BRIC126) enabled phagocytosis of ALL cells compared to IgG1 isotype and anti-CD45 control antibodies as measured by significant increases in the phagocytic index. In addition, anti-CD47 antibodies enabled phagocytosis of all ALL subtypes profiled, including those with cytogenetically high-risk (Ph+ ALL and MLL+ALL). Since several studies report that CD47-SIRPα signaling may be species-specific, the ability of anti-CD47 antibody-coated human cells to be phagocytosed by mouse macrophages was determined before proceeding with in vivo antibody treatment experiments in mouse xenotransplants. Similar to human macrophages, two blocking anti-CD47 antibodies (B6H12.2 and BRIC126) enabled phagocytosis of ALL cells by mouse macrophage effectors compared to IgG1 isotype and anti-CD45 antibody controls. Furthermore, no phagocytosis was observed with a non-blocking anti-CD47 antibody (2D3). Lastly, blockade of SIRPα with an anti-mouse SIRPα antibody also resulted in increased phagocytosis, thus supporting the mechanism of increased phagocytosis resulting from disruption of the CD47-SIRPα interaction.

Ex Vivo Coating of ALL Cells with an Anti-CD47 Antibody Inhibits Leukemic Engraftment. The ability of a blocking anti-CD47 antibody to eliminate ALL in vivo was investigated by two independent methods. First, the ability of anti-CD47 antibody to inhibit ALL engraftment was determined using an antibody pre-coating assay. ALL cells were coated ex vivo with either IgG1 isotype control, anti-CD45, or anti-CD47 antibody (B6H12.2), transplanted into sublethally-irradiated immunodeficient NOD/SCID/Il2γr null (NSG) mice, and measured for ALL engraftment in the peripheral blood and bone marrow 6-10 weeks later. Prior to transplantation, coating of ALL cells with antibody was verified by flow cytometry (FIG. 27A). Antibody pre-coating experiments were performed with both primary B- and T-ALL samples to include the two major disease subtypes. Anti-CD47 antibody significantly inhibited leukemic engraftment of both B- and T-ALL cells in the peripheral blood (FIG. 27B) and bone marrow (FIG. 27C) compared to IgG1 isotype or anti-CD45 antibody controls. Pre-coating with the anti-CD47 antibody nearly completely eliminated ALL engraftment in vivo.

Anti-CD47 Antibody Eliminates ALL Engraftment in the Peripheral Blood and Bone Marrow.

Figure 28B:
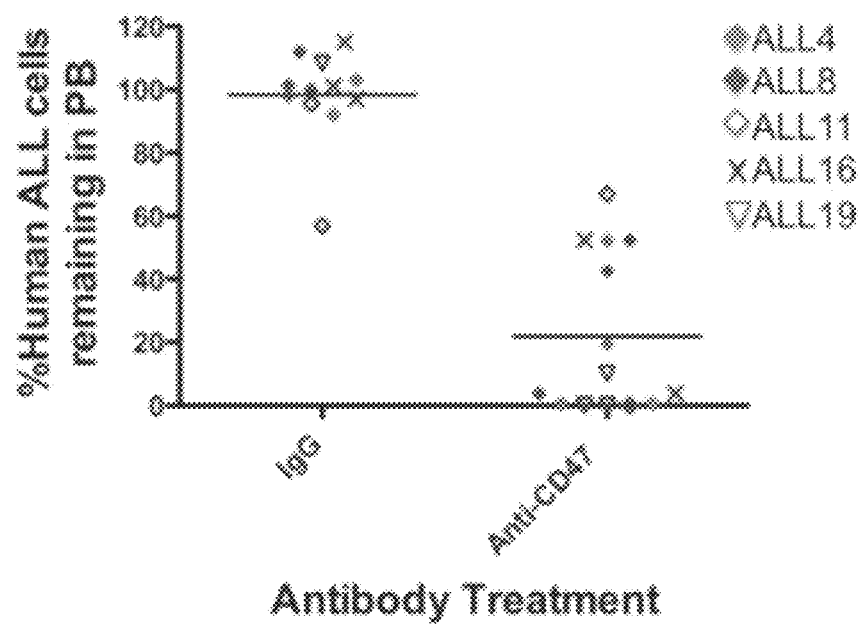
Figure 28C:
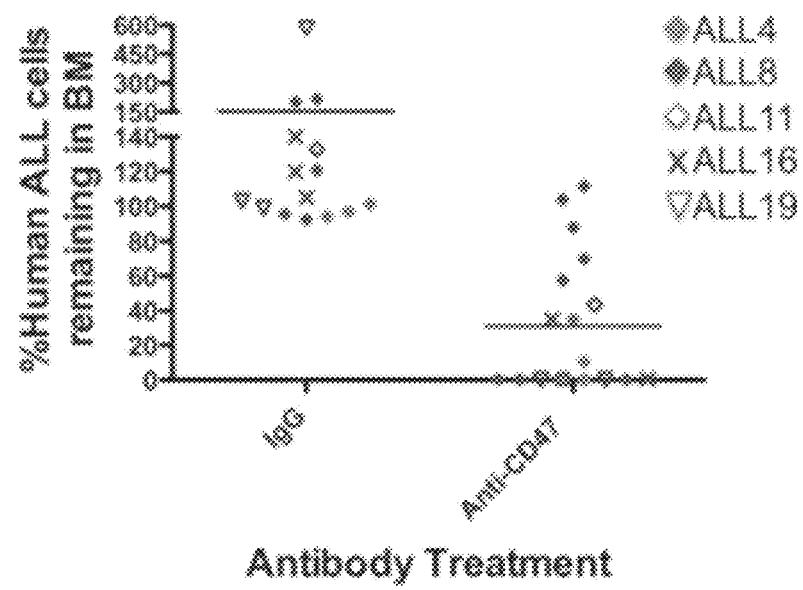
Figure 28D:
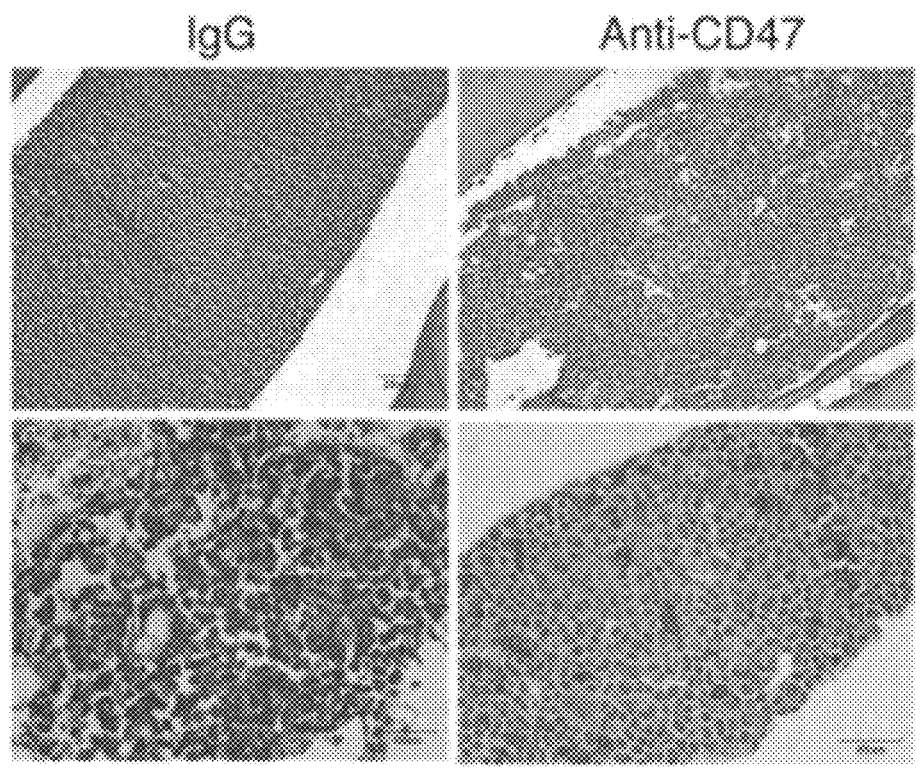

In the second method of investigating the in vivo efficacy of an anti-CD47 antibody against human ALL, mice were first stably engrafted with ALL cells and then treated with antibody. 1–4×10⁶ B- or T-ALL cells were transplanted into sublethally-irradiated NSG newborn pups or adults. Six to ten weeks later, ALL engraftment was measured in the peripheral blood and bone marrow by flow cytometry. Those mice that had significant levels of ALL engraftment were then selected for in vivo antibody therapy (FIG. 28A), as determined by greater than 10% human chimerism in the peripheral blood and/or bone marrow with engraftment ranging from 10-97%. ALL engrafted mice were treated with daily intraperitoneal injections of 100 μg IgG control or anti-CD47 antibody (B6H12.2) for 14 days. This dosing regimen was selected based on our prior study demonstrating elimination of AML in mouse xenotransplants. Tumor burden was then measured post-treatment in the peripheral blood and bone marrow by flow cytometry. Compared to IgG control, anti-CD47 antibody therapy reduced the level of circulating leukemia, and in most cases eliminated ALL from the peripheral blood (FIG. 28 A,B). This effect was observed for mice transplanted with both B- and T-ALL cells. Similarly, anti-CD47 antibody reduced or eliminated ALL engraftment in the bone marrow, while ALL disease burden increased with IgG control treatment (FIG. 28C). Bone marrow histology of antibody-treated mice revealed infiltration of monomorphic leukemic blasts in control IgG-treated mice (FIG. 28D). Anti-CD47 antibody-treated bone marrow demonstrated normal mouse hematopoietic cells with cleared hypocellular areas. Immunohistochemistry of mouse marrows confirmed near complete invasion of human CD45-positive leukemic blasts in IgG-treated marrow compared to few human CD45-positive leukemia cells observed in anti-CD47 antibody-treated marrow (FIG. 28D).

Anti-CD47 Antibody Eliminates ALL Engraftment in the Spleen and Liver. Hepatomegaly and splenomegaly can cause clinical complications and are a common finding in ALL, being observed in up to 69% of patients at diagnosis. To determine whether anti-CD47 antibody could potentially treat hepatosplenomegaly in ALL, we investigated the ability of anti-CD47 antibody to eliminate ALL engrafted in the spleen and liver. Of the ALL samples utilized for in vivo treatment studies, we identified three B-ALL patient samples (ALL8, ALL21, and ALL22) that gave rise to disease in the spleen and/or liver, with associated splenomegaly, when transplanted into NSG mice. These mice were treated for 14 days with the identical regimen of either IgG or anti-CD47 antibody as in FIG. 28 with spleen weights and ALL chimerism in the spleen and liver measured post-treatment. Control IgG-treated B-ALL-engrafted mice exhibited significant splenomegaly compared to untransplanted NSG mice (FIG. 29A,B). In contrast, anti-CD47 antibody treatment reduced ALL-induced splenomegaly to spleen sizes similar to untransplanted NSG mice (FIGS. 29A,B). To determine whether this effect was due to direct elimination of ALL cells in the spleen, the spleens of B-ALL-engrafted mice treated with IgG control or anti-CD47 antibody were analyzed for ALL disease burden. Compared to IgG-treated mice, anti-CD47 antibody significantly eliminated B-ALL engraftment in the spleen (FIG. 29C). Similarly, anti-CD47 antibody significantly eliminated ALL in the liver compared to the extensive leukemic infiltration observed with control IgG treatment (FIG. 29D). These results indicate that anti-CD47 antibody is highly effective in eliminating ALL in the spleen and liver, in addition to the peripheral blood and bone marrow.

We report here that CD47 is expressed at high levels on a large subset of human ALL subtypes, that cell surface CD47 is a monoclonal antibody target for eliminating ALL blasts by enhancing innate immune system recognition of leukemic blasts by macrophage-mediated phagocytosis, and that CD47 itself is an independent prognostic variable in ALL that can predict disease free survival, overall survival, and relapse in both mixed and high-risk ALL patients. Together, these data show that ALL pathogenesis relies on mechanisms to evade innate immune recognition and that modulation of the innate immune recognition of tumor cells is a viable treatment modality.

Within the last few years, several cell surface proteins have been identified as candidate targets, and some monoclonal antibodies have proceeded into early and late phase clinical trials. Most therapeutic antibodies in clinical development have been focused on B-ALL. One such candidate is CD20, as its expression is observed in approximately 40 to 50% of B-ALL cases. Rituximab, an anti-CD20 antibody, initially approved for treatment of B cell lymphoma, has demonstrated a significant survival advantage when added to standard chemotherapy in some ALL clinical trials, particularly the Burkitt's subtype. Although effective in adult CD20+ B-ALL, there is a paucity of clinical data on the efficacy of rituximab in pediatric ALL. In contrast to CD20, CD22 is expressed in a larger percentage of B-ALL cases and is present on greater than 90% of B-ALL patients. Epratuzumab, a humanized monoclonal anti-CD22 antibody, is currently being investigated in clinical trials. Although early clinical studies with epratuzumab as a single agent in relapsed ALL showed limited effect, anti-CD22 antibody-immunotoxin conjugates may improve the efficacy of epratuzumab, since CD22 is reported to be rapidly internalized upon antibody binding. Several immunoconjugates directed against CD22 are currently being explored in Phase I trials. In addition, antibodies and immunotoxins to other antigens including CD19 are currently being explored.

Although several therapeutic antibodies are in clinical development for B-ALL, there are relatively few antibody therapies for treatment of T-ALL. The most prominent antibody for T-ALL, alemtuzumab, is targeted at CD52, as it is expressed on greater than 95% of normal lymphocytes and at higher levels in T compared to B lymphoblasts. Although pre-clinical data suggest potential efficacy of alemtuzumab, early phase clinical trials do not report a significant benefit as a single agent or in combination with chemotherapy for the treatment of relapsed T-ALL.

In contrast to the targeted therapies developed for B-ALL and T-ALL, our data strongly suggest that an anti-CD47 antibody can be effective in eliminating both B- and T-ALL and thus could increase the number of therapeutic options for both. Because anti-CD47 antibody treatment may eliminate ALL blasts with limited toxicity and is equally effective in targeting low, standard, and high-risk ALL, these results provide a strong rationale for development of an anti-CD47 antibody for the treatment of ALL patients.

Example 7

Expression of CD47 on Solid Tumor Cells and Manipulation of Phagocytosis of the Same Several anti-human CD47 monoclonal antibodies have been generated, including some capable of blocking the CD47-SIRPα interaction (B6H12 and Bric126) and others unable to do so (2D3). We tested the ability of these antibodies to enable phagocytosis of ovarian, bladder, and colon cancer cells by macrophages in vitro, and to alter the survival of animals engrafted with these cancer cells in vivo. In contrast to cells treated with an IgG1 isotype control or non-blocking anti-CD47 antibody (2D3), tumor cells treated with blocking anti-CD47 antibodies B6H12 or Bric126 were efficiently phagocytosed by mouse and human macrophages. Colon cancer stem cells (Linneg, EpCAM+, CD44+, CD166+) were isolated by Fluorescence Activated Cell Sorting (FACS) from patient tumor samples.

The cell samples tested were as follows:

Ovarian. Patient ovarian cancer (OC) cells were engrafted into the peritoneal cavity of NSG mice. Prior transduction of these cells with a *lentivirus* designed to express GFP and luciferase enabled the use of bioluminescent imaging to monitor tumor growth. After confirming engraftment of the OC cells, mice were treated daily with an intraperitoneal injection of 400 μg anti-CD47 (clone Bric126) or control mouse IgG. Tumor growth was then evaluated biweekly with bioluminescent imaging.

The fold change in total flux (photons/sec) is shown for each mouse after each individual mouse was normalized to its respective pretreatment value. IgG treated mice (n=9) are represented by red circles. Anti-CD47 treated mice (n=10) are represented by blue triangles. The horizontal line represents the mean bioluminescent signal (plus standard error) of each treatment group. The fold difference between the two treatment groups is shown at each time point.

Pancreatic. Pancreatic cancer (PANC1) cells were transduced with a *lentivirus* designed to express GFP and Luciferase. Successfully transduced (GFP+) cells were isolated by FACS. 500,000 transduced PANC1 cells were directly injected into the pancreas of NSG mice. After seven days, engraftment of PANC1 cells was quantified by bioluminescent imaging. Mice were then treated daily with 500 ug control IgG (n=5) or anti-CD47, clone B6H12 (n=5). Tumor growth was monitored and quantified weekly by bioluminescent imaging. Each symbol represents an individual mouse.

Breast. $10^6$ cells from a patient breast cancer xenograft were engrafted into the mammary fat pad of NSG mice. Daily intraperitoneal injections of either 400 ug control IgG or anti-CD47 (B6H12) were initiated 2 weeks after cells were injected. Antibody treatment was stopped after 8 weeks. Tumor formation occurred in all control IgG treated mice. Importantly, the anti-CD47 treated mice were evaluated 3 months after stopping antibody treatment, and still no tumor formation was detected in any of the mice, indicating that the anti-CD47 antibody successfully targeted and eliminated the breast CSCs. Representative images of the mammary fat pads of 3 mice from each treatment group Colon. Patient colon cancer cells were engrafted subcutaneously on the back of of NSG mice. Prior transduction of all injected cells with a *lentivirus* designed to express GFP and luciferase enabled the use of bioluminescent imaging to monitor tumor growth. After confirming engraftment of the colon cancer cells, mice were treated daily with an intraperitoneal injection of 500 μg anti-CD47 (clone B6H12), anti CD44 (Hermes-3), control mouse IgG, or a combination of anti-CD44 and anti-CD47 antibodies. Tumor growth was then evaluated weekly with bioluminescent imaging.

Bladder Metastasis. Tumor cells from a patient bladder cancer sample which reliably forms metastases to they lymph nodes and lungs were injected subcutaneously onto the back of NSG mice. Treatment with anti-CD47 (400 μg/day), anti-CD44 (150 μg, MWF), or Herceptin (200 μg/week) antibodies was initiated upon detection of a palpable tumor mass. The number of metastases was determined by gross examination of excised lymph nodes at the conclusion of the experiment. The number of micrometastases was determined by a trained pathologist on sections cut from lungs preserved in 10% buffered formalin phosphate.

Expression of CD47 on various cancer cells is shown in FIG. 30. As shown in FIG. 31, antibodies targeted to human CD47 enable the phagocytosis of OC cells. A: CFSE-labeled primary human bladder cancer cells were incubated with human macrophages in the presence of the indicated antibodies and assessed for the presence of tumor cells within macrophages. B-C: Phagocytosis of patient ovarian cancer cells (B) or colon cancer stem cells (C) resulting from indicated antibody treatment was quantified. Each dot color represents a different primary tumor sample. The phagocytic index was determined as the number of OC cells present within 100 macrophages.

As shown in FIG. 32, antibodies targeted to CD47 inhibit the growth of patient tumors. A-D: Tumor cells from ovarian (A), pancreatic (B), breast (C), or colon (D) tumors were engrafted into immunodeficient mice. These mice were then treated with control IgG or anti-CD47 antibodies and tumor growth was assessed directly or by bioluminescence. In all cases, anti-CD47 antibody treatment substantially inhibited tumor growth. E-F: Tumor cells from patient bladder were injected subcutaneously into immunodeficient mice and treated with the indicated antibodies. Anti-CD47 antibody treatment significantly inhibited metastasis to the lymph nodes (E) and formation of micrometastases in the lungs (F). The total number of metastases detected in each treatment group is indicated.

Example 8

Expression of CD47 in Brain Tumor

Acquisition of Brain Tumor Samples: Freshly resected brain tumor samples were obtained from the department of Neurosurgery under IRB approved protocols. Samples are minced using a sterile scalpel and washed in HBSS to remove debris. Minced tissue is then incubated in collagenase IV (img/ml) for 60-90 minutes at 37° C. with constant agitation. Dissociated cells are then passed sequentially through a 100, 70 and 40 μm cell strainer and washed in HBSS. Dead cells are removed by density centrifugation in 0.9M sucrose and then treated with ACK-RBC lysis buffer (invitrogen) to remove red blood cells. Cells are then collected by centrifugation and resuspended in FACS buffer.

FACS Staining: Single cell suspension were stained with CD133/1-APC and CD133/2-APC (Miltenyi) and CD47-PE (BD biosciences) and analyzed on ARIA-II (BD Biosciences).

Results:

In 10 gliomas analyzed, 10/10 tumors were $CD47^+$ with varying degree of CD47 expression.

An average of 66% of the cells were $CD47^+$, where as only 4/10 tumors were $CD133^+$. In the $CD133^+$ tumors all $CD133^+$ cells also expressed CD47.

This data suggests that anti-CD47 therapy can be a viable avenue of investigation in human glioblastoma. This also suggests that at least in $CD133^+$ tumors targeting CD47 would also target the cancer stem cell population.

|  | % of the viable, CD45− cells: | | |
| --- | --- | --- | --- |
| Tumor Date | CD133+ | CD47+ | CD47+133+ (%) |
| Nov. 15, 2006 | 45% | 95% | 53% |
| Jun. 29, 2007 | 0% | 97.1% | 0 |
| Oct. 1, 2007 | 0% | 46% | 0 |
| Feb. 12, 2008 | 0% | 20% | 0 |
| Mar. 27, 2008 | 0% | 31% | 0 |
| Apr. 10, 2008 | 7.6% | 68% | 8.5% |
| Apr. 28, 2008 | 9.1% | 74% | 8.8% |
| Jun. 2, 2008 | 4.5% | 92% | 8.5% |
| Jul. 15, 2008 | 0.0% | 37% | 0.0% |
| Oct. 9, 2008 | 0.0% | 95% | 0.0% |

An analysis of survival vs. gene expression data for cd47 and CD133/Prom1 shows that patients with glioblastoma whose tumors express low CD47 have better survival (p=0.0239).

What is claimed is:

1. A method of treating a human subject for a solid tumor, the method comprising:
    administering to a human subject in need thereof an antibody that disrupts the binding of CD47 with SIRPα, at a dose that achieves a depletion in solid tumor cells by increasing phagocytosis of tumor cells.

2. The method of claim 1, wherein the antibody that disrupts the binding of CD47 with SIRPα specifically binds to CD47.

3. The method of claim 1, wherein the antibody is a humanized or chimeric monoclonal antibody.

4. The method of claim 1, wherein the solid tumor is a carcinoma.

5. The method of claim 4, wherein said carcinoma is an ovarian carcinoma or a bladder carcinoma.

6. The method of claim 1, wherein the solid tumor is a lymphoma.

7. The method of claim 1, wherein the solid tumor is a sarcoma.

8. The method of claim 7, wherein the solid tumor is a melanoma, a glioblastoma or a medulloblastoma.

9. The method of claim 8, wherein the solid tumor is a glioblastoma.

10. The method of claim 8, wherein the solid tumor is a medulloblastoma.

* * * * *